United States Patent
Horvath et al.

(10) Patent No.: US 7,482,462 B2
(45) Date of Patent: Jan. 27, 2009

(54) ACYLSULFONAMIDES AS INHIBITORS OF STEROID SULFATASE

(76) Inventors: Amarylla Horvath, Schönbrunnerstr., 293/2/2 Vienna (AT) 1120; Philipp Lehr, Technikerstrasse, 30/18 Moedling (AT) 2340; Peter Nussbaumer, Kaiserin Elisabeth-Strasse, 5/9 Maria Enzersdorf (AT) 2344; Erwin Paul Schreiner, Anton Baumgartner Strasse, 125/4/02 Vienna (AT) 1230

( * ) Notice: Subject to any disclaimer, the term of this patent is extended or adjusted under 35 U.S.C. 154(b) by 671 days.

(21) Appl. No.: 10/490,464

(22) PCT Filed: Oct. 4, 2002

(86) PCT No.: PCT/EP02/11140

§ 371 (c)(1),
(2), (4) Date: Oct. 1, 2004

(87) PCT Pub. No.: WO03/031397

PCT Pub. Date: Apr. 17, 2003

(65) Prior Publication Data

US 2005/0059712 A1    Mar. 17, 2005

(30) Foreign Application Priority Data

| Oct. 5, 2001 | (GB) | ................. | 0124027.4 |
| Oct. 5, 2001 | (GB) | ................. | 0124028.2 |
| Oct. 16, 2001 | (GB) | ................. | 0124839.2 |
| Nov. 12, 2001 | (GB) | ................. | 0127173.3 |
| Nov. 12, 2001 | (GB) | ................. | 0127174.1 |
| Nov. 14, 2001 | (GB) | ................. | 0127343.2 |
| May 20, 2002 | (GB) | ................. | 0211524.4 |

(51) Int. Cl.
*C07D 211/26* (2006.01)
*C07D 211/70* (2006.01)

(52) U.S. Cl. .................................. 546/229; 546/336

(58) Field of Classification Search ................ 546/229, 546/336

See application file for complete search history.

(56) References Cited

U.S. PATENT DOCUMENTS

| 3,534,049 | A | 10/1970 | Bell ........................... 260/293 |
| 3,637,845 | A | 1/1972 | Moore et al. ................. 260/556 |
| 3,707,559 | A | 12/1972 | Mazur ......................... 260/558 |
| 4,034,091 | A | 7/1977 | Powell ........................ 424/246 |
| 4,244,950 | A | 1/1981 | De Ridder et al. .......... 424/248 |
| 4,282,212 | A | 8/1981 | Berger et al. ................ 424/200 |
| 4,880,804 | A | 11/1989 | Carini et al. ................ 514/234 |
| 5,053,072 | A | 10/1991 | Ort et al. ........................ 71/92 |
| 5,057,144 | A | 10/1991 | Daum et al. .................... 71/92 |
| 5,085,684 | A | 2/1992 | Muller et al. ................... 71/92 |
| 5,204,354 | A | 4/1993 | Chakravarty et al. ........ 514/259 |
| 5,252,540 | A | 10/1993 | Heistracher et al. ......... 504/280 |
| 5,256,632 | A | 10/1993 | Wolf et al. ................... 504/252 |
| 5,300,480 | A | 4/1994 | Haas et al. ................... 504/273 |
| 5,324,710 | A | 6/1994 | Ort et al. ..................... 504/239 |
| 5,389,487 | A | 2/1995 | Kawakami et al. .......... 430/120 |
| 5,411,980 | A | 5/1995 | Ashton et al. ................ 514/384 |
| 5,521,206 | A | 5/1996 | Muller et al. ................ 514/400 |
| 5,565,429 | A | 10/1996 | Vincent et al. ................. 514/18 |
| 5,684,015 | A | 11/1997 | Mederski et al. ............ 514/303 |
| 6,013,662 | A | 1/2000 | Bourzat et al. .............. 504/273 |
| 6,160,125 | A | 12/2000 | Prasad et al. ................ 548/263 |
| 6,180,567 | B1 | 1/2001 | Muller et al. ................ 504/273 |
| 6,383,988 | B1 | 5/2002 | Muller et al. ................ 514/410 |
| 2003/0191323 | A1 | 10/2003 | Ikawa et al. ................. 548/530 |
| 2003/0211942 | A1 | 11/2003 | Feucht et al. ................ 504/130 |
| 2004/0122063 | A1 | 6/2004 | Yoshino et al. .............. 514/357 |

FOREIGN PATENT DOCUMENTS

| CH | 402 844 | 11/1965 |
| EP | 0 048 433 | 3/1982 |
| EP | 0 089 089 | 9/1983 |
| EP | 0089089 | * 9/1983 |
| EP | 0 373 951 | 6/1990 |
| EP | 0 400 835 | 12/1990 |
| EP | 0 400 974 | 12/1990 |
| EP | 0 412 594 | 2/1991 |
| EP | 0 638 553 | 2/1995 |
| EP | 0 738 725 | 10/1996 |
| EP | 0 757 986 | 2/1997 |
| EP | 1 008 592 | 6/2000 |
| EP | 1 097 706 | 5/2001 |
| EP | 1 097 719 | 5/2001 |

(Continued)

OTHER PUBLICATIONS

Hohenloche-Oerlingen et al. Monatsh. Chem. 1970, 101(2), 623-6.*

(Continued)

*Primary Examiner*—D. Margaret Seaman
*Assistant Examiner*—Nizal S Chandrakumar
(74) *Attorney, Agent, or Firm*—Novartis HG; John B. Alexander

(57) ABSTRACT

A compound of formula

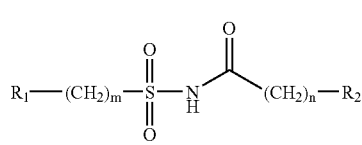

wherein $R_1$ is haloalkyl, alkenyl, phenyl, thienyl, pyridine, benzthiazolyl, chromanyl (1,2-dihydrobenzopyranyl) or ($C_{6-18}$)aryl, and $R_1$ or $R_2$ independently of each other are substituted ($C_{4-8}$)cycloalkyl, a substituted bridged cycloalkyl system, substituted piperidine, substituted tetrahydropyridine, or a substituted bridged heterocyclic system, useful as a pharmaceutical.

4 Claims, No Drawings

FOREIGN PATENT DOCUMENTS

| | | |
|---|---|---|
| EP | 1 113 009 | 7/2001 |
| EP | 1 236 468 | 9/2002 |
| GB | 1263404 | 2/1972 |
| GB | 1454737 | 11/1976 |
| GB | 1570536 | 7/1980 |
| GB | 1576120 | 10/1980 |
| GB | 1576300 | 10/1980 |
| GB | 2263637 * | 8/1993 |
| JP | 8208632 | 8/1996 |
| JP | 2001097946 | 4/2001 |
| WO | 88/03922 | 6/1988 |
| WO | 92/01677 | 2/1992 |
| WO | 93/17008 | 9/1993 |
| WO | 94/26702 | 11/1994 |
| WO | 95/09151 | 4/1995 |
| WO | 96/08187 | 3/1996 |
| WO | 96/09818 | 4/1996 |
| WO | 96/15099 | 5/1996 |
| WO | 96/33170 | 10/1996 |
| WO | 96/38471 | 12/1996 |
| WO | 97/05868 | 2/1997 |
| WO | 97/38986 | 10/1997 |
| WO | 97/41852 | 11/1997 |
| WO | 97/43260 | 11/1997 |
| WO | 98/41515 | 9/1998 |
| WO | 98/54207 | 12/1998 |
| WO | 99/20623 | 4/1999 |
| WO | 99/47508 | 9/1999 |
| WO | 99/55661 | 11/1999 |
| WO | 99/64442 | 12/1999 |
| WO | 00/19825 | 4/2000 |
| WO | 00/24710 | 5/2000 |
| WO | 00/59880 | 10/2000 |
| WO | 00/64888 | 11/2000 |
| WO | 00/71509 | 11/2000 |
| WO | 01/07036 | 2/2001 |
| WO | 01/23349 | 4/2001 |
| WO | 01/35936 | 5/2001 |
| WO | 01/57037 | 8/2001 |

OTHER PUBLICATIONS

* Poirier et al., "Steroid Sulfatase Inhibitors", Expert Opinion on Therapeutic Patents, vol. 9, No. 8, pp. 1083-1099 (1999).

* Purohit et al., "Recent Advances in the Development or Steroid Sulphatase Inhibitors", J. of Steroid Biochemistry and Molecular Biology, vol. 69, pp. 227-238 (1999).

Hohenlohe-Oehringen et al., "Arylsulfonylureido- and Arylsulfonylamido Derivatives of Hydroxy and Oxocycloalkanes as potential Antidiabetics. X. N-sulfonylated and N-acylated Camphor-3-Carboxamides", Monatsh. Chem., vol. 101, pp. 623-626 (1970)—CAPLUS Abstract No. 1970:132987.

Ramón et al., "Nonreductive Enantioselective Ring Opening of N-(Methylsulfonyl)dicarboximides with Diisopropoxytitanium α, α, ά, ά—Tetraaryl-1,3-dioxolane-4,5-dimethanolate", Helvetica Chemica Acta, vol. 79, pp. 875-894 (1996).

Dowell et al., "Novel Inhibitors of Prolyl 4-Hydroxylase", J. Med. Chem., vol. 35, pp. 800-804 (1992).

Deprez et al., "Balanced $AT_1$ and $AT_2$ Angiotensin II Antagonists. I. New Orally Active 5-Carboxyl Imidazolyl Biphenyl Sulfonylureas", Bioorg. Med., Chem. Lett., vol. 5, No. 22, pp. 2605-2610 (1995).

Aktaev et al., "N-Sulfonylamides of Polyfluorocarboxylic Acids", Zh. Organic Khim., vol. 10, No. 3, pp. 470-473 (1974).

Hendrickson et al., "The Direct Introduction of the Diazo Function in Organic Synthesis", J. Organic Chemical, vol. 33, No. 9, pp. 3610-3618 (1968).

Ishizuka et al., "An Efficient Method for the Preparation of Enantiomerically Pure N- Acylarylsulfonamides Having an Asymmetric Center at the α-Position: Condensation of Acid Chlorides and . . . ", Synthesis, vol. 6, pp. 784-788 (2000).

Cloudsdale et al., "Herbicidal Sulfonylamides", ACS Symp. Ser., 584 (Synthesis and Chemistry of Agrochemicals IV), pp. 37-45 (1995).

* cited by examiner

ACYLSULFONAMIDES AS INHIBITORS OF STEROID SULFATASE

The present invention relates to acylsulfonamides, e.g. useful in the treatment of disorders mediated by the action of steroid sulfatase.

In one aspect the present invention provides a compound of formula

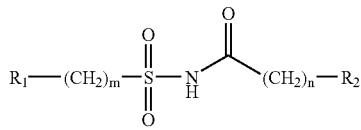

I wherein $R_1$ is $(C_{1-6})$haloalkyl, unsubstituted $(C_{2-6})$alkenyl, $(C_{2-6})$alkenyl substituted by phenyl, unsubstituted or by 1 to 5 substitutents substituted thienyl, pyridine, benzthiazolyl, chromanyl (i.e. 1,2-dihydrobenzopyranyl) or $(C_{6-18})$aryl, wherein the substituents are selected from the group consisting of halogen, nitro, di($C_{1-4}$)alkylamino, cyano, $(C_{1-6})$alkyl, $(C_{1-4})$haloalkyl, unsubstituted phenylcarbonylamino $(C_{1-4})$alkyl, $(C_{1-4})$alkoxy, $(C_{1-4})$haloalkoxy, aminocarbonyl, di($C_{1-4}$)alkylaminocarbonyl, $(C_{1-4})$alkylcarbonyl, $(C_{1-4})$alkoxycarbonyl, unsubstituted phenyl, carboxyl, and phenyl-substituted phenylcarbonylamino($C_{1-4}$)alkyl or substituted phenyl, wherein the phenyl-substitutents are selected from the group consisting of halogen, nitro, di($C_{1-4}$)alkylamino, cyano, $(C_{1-6})$ alkyl, $(C_{1-4})$haloalkyl, $(C_{1-4})$alkoxy, $(C_{1-4})$haloalkoxy, aminocarbonyl, di($C_{1-4}$)alkylaminocarbonyl, $(C_{1-4})$alkylcarbonyl, $(C_{1-4})$alkoxycarbonyl and carboxyl, or $R_1$ is a group of formula

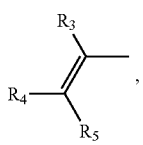

II or of formula

III or of formula

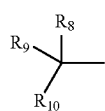

IV $R_2$ is a group of formula

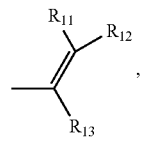

V or of formula

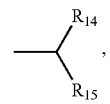

VI or of formula

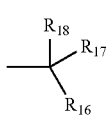

VII $R_3$ and $R_{13}$ independently of each other are hydrogen, hydroxy, halogen, cyano, $(C_{1-4})$alkyl, $(C_{1-4})$alkoxy, phenyl or phenoxy, at least one of $R_4$ and $R_5$ together with the carbon atom to which they are attached, $R_{11}$ and $R_{12}$ together with the carbon atom to which they are attached, independently of each other are a substituted bridged cycloalkyl system,
$(C_{4-8})$cycloalkyl,
piperidine, tetrahydropyridine, or
bridged heterocyclic system, wherein the substitutents are selected from the group consisting of $(C_{1-6})$alkoxycarbonylamino,
$(C_{1-6})$alkoxycarbonyl(($C_{1-4}$)alkyl)amino,
$(C_{1-6})$alkoxycarbonyl(($C_{2-4}$)alkenyl)amino,
$(C_{3-8})$cycloalkylcarbonylamino,
$(C_{3-8})$cycloalkylcarbonyl(($C_{1-4}$)alkyl)amino,
$(C_{3-8})$cycloalkylcarbonyl(($C_{2-4}$)alkenyl)amino,
$(C_{1-6})$alkoxycarbonyloxy,
phenyl($C_{1-4}$)alkylcarbonyloxy, wherein phenyl is unsubstituted or substituted and wherein the substituents are as defined above for substituted phenyl,
phenylsulphonyl, wherein phenyl is unsubstituted or substituted and wherein the substituents are defined as above for substituted phenyl, ($C_{4-8}$)alkyl, e.g. ($C_{5-8}$)alkyl,
($C_{1-4}$)hydroxyalkyl,
($C_{1-4}$)hydroxyalkyl substituted by phenyl, wherein phenyl is unsubstituted or substituted and wherein the substituents are as defined above for substituted phenyl,
($C_{1-6}$)alkoxycarbonyl($C_{1-4}$)alkyl,
($C_{3-8}$)cycloalkoxycarbonyl($C_{1-4}$)alkyl,
($C_{1-6}$)alkoxycarbonylamino($C_{1-4}$)alkyl,
($C_{3-8}$)cycloalkylcarbonylamino($C_{1-4}$)alkyl,
phenyl or substituted phenyl, wherein the substituents are as defined above for substituted phenyl,
heterocyclyl having 5- or 6-ring members and 1 to 4 heteroatoms selected from N, O, S, e.g. oxadiazolyl,
($C_{3-8}$)cycloalkoxycarbonyl,
($C_{3-8}$)cycloalkyl($C_{1-4}$)alkylcarbonyl, wherein cycloalkyl is unsubstituted or substituted by hydroxy,
phenylcarbonyl, wherein phenyl is unsubstituted or substituted and wherein the substituents are defined as above for substituted phenyl,
($C_{3-8}$)cycloalkylaminocarbonyl,
($C_{3-8}$)cycloalkyl(($C_{1-4}$)alkyl)aminocarbonyl,
($C_{3-8}$)cycloalkyl(($C_{2-4}$)alkenyl)aminocarbonyl, and
($C_{1-8}$)alkoxycarbonyl, $R_3$, $R_8$, $R_{13}$ and $R_{18}$ independently of each other are hydrogen, hydroxy, halogen, cyano, ($C_{1-4}$)alkyl, ($C_{1-4}$)alkoxy, phenyl or phenoxy, Either
$R_8$ or $R_{18}$, respectively, independently of each other are hydrogen, hydroxy, halogen, cyano, ($C_{1-4}$)alkyl, ($C_{1-4}$)alkoxy, phenyl or phenoxy, and at lest one of
$R_9$ and $R_{10}$ together with the carbon atom to which they are attached,
$R_{16}$ and $R_{17}$ together with the carbon atom to which they are attached, independently of each other have the meaning of $R_4$ and $R_5$ together with the carbon atom to which they are attached, as defined above, Or
at least one of
$R_9$ and $R_{10}$ together with the carbon atom to which they are attached,
$R_{16}$ and $R_{17}$ together with the carbon atom to which they are attached, are ($C_{3-8}$)cycloalkyl, and
$R_8$ or $R_{18}$, respectively, independently of each other are a substituted
bridged cycloalkyl system, ($C_{4-8}$)cycloalkyl, substituted piperidine, tetrahydropyridine, or a bridged heterocyclic system, wherein the substitutents are as defined above for the corresponding groups,
$R_6$ and $R_{15}$ independently of each other are ($C_{1-6}$)haloalkyl, unsubstituted or substituted ($C_{6-18}$)aryl, wherein the aryl-substitutents are as defined above, or a substituted
bridged cycloalkyl system, ($C_{4-8}$)cycloalkyl, piperidine, tetrahydropyridine, or bridged heterocyclic system,
wherein the substitutents are as defined above for the corresponding groups, or
$R_6$ and $R_{15}$ independently of each other are amino substituted by a substituted
bridged cycloalkyl system, ($C_{4-8}$)cycloalkyl, piperidine, tetrahydropyridine, or bridged heterocyclic system,
wherein the substitutents are as defined above for the corresponding group, $R_7$ and $R_{14}$ independently of each other are a substituted
bridged cycloalkyl system, ($C_{4-8}$)cycloalkyl, piperidine, tetrahydropyridine, or bridged heterocyclic system, wherein the substitutents are as defined above for the corresponding groups, or $R_7$ and $R_{14}$ independently of each other are amino substituted by a substituted
bridged cycloalkyl system, ($C_{4-8}$)cycloalkyl, piperidine, tetrahydropyridine, or bridged heterocyclic system, wherein the substitutents are as defined above for the corresponding group,
m is 0, 1, 2, 3 or 4, such as 0 or 1,
n is 0, 1, 2, 3 or 4, such as 0 or 1, and
If
m and/or n are other than 0, Then
$R_1$, if m is other than 0, and $R_2$, if n is other than 0, independently of each other have the meaning as defined above and additionally may be substituted piperazine, wherein the substitutents are as defined above for substituted piperidine above; and
a substituted bridged cycloalkyl system is substituted as defined above for a substituted bridged cycloalkyl system, and additionally may be substituted by oxo and/or ($C_{1-4}$)alkyl; and If
$R_1$ is a substituted
bridged cycloalkyl ring system, ($C_{4-8}$)cycloalkyl, piperidine, tetrahydropyridine, or a bridged heterocyclyl ring system, wherein the substituents are as defined above for the corresponding groups, or if $R_1$ is additionally piperazine, if m is other than 0, Then
$R_2$ has the meaning as defined above and additionally may be ($C_{1-6}$)haloalkyl, unsubstituted ($C_{2-6}$)alkenyl, ($C_{2-6}$)alkenyl substituted by phenyl, unsubstituted or by 1 to 5 substitutents substituted
thienyl, pyridine, benzthiazolyl, chromanyl (i.e. 1,2-dihydrobenzopyranyl) or ($C_{6-18}$)aryl, wherein the substituents are as defined above for the corresponding groups, and If
m Is 0, n is 0 and $R_2$ is substituted ($C_{4-8}$)cycloalkyl or a substituted bridged cycloalkyl, ring system, wherein the substituents are as defined above, Then
$R_1$ is other than ($C_{1-6}$)haloalkyl.
In a compound of formula I at least one substituent selected from the group consisting of a substituted bridged cycloalkyl ring system, substituted ($C_{4-8}$)cycloalkyl, substituted piperidine, substituted tetrahydropyridine, substituted piperazine, or a substituted bridged heterocyclyl ring system, wherein the substituents are as defined above for the corresponding groups, is present. In a compound of formula I m is preferably 0 or 1, and n is preferably 0 or 1.
If not otherwise specified herein
cycloalkyl includes e.g. non-bridged ($C_{3-8}$)cycloalkyl, such as ($C_{4-8}$)cycloalkyl,
heterocyclyl includes heterocyclyl having 5 to 6 ring members and 1 to 4 heteroatoms selected from N, S or O, optionally anellated with another ring (system), such as piperidine, tetrahydropyridine, pyridine, piperazine, thienyl, pyridine, benzthiazolyl, chromanyl, oxadiazolyl,
aryl includes $(C_{6-18})$aryl, e.g. $(C_{6-12})$aryl, such as naphthyl, phenyl.

A substituent attached to cyclohexyl, a piperidine, tetrahydropyridine or piperazine ring in a compound of formula I may be in any position with respect to the sulfonamide group, or with respect to a group —$(CH_2)_m$— or —$(CH_2)_n$—, also attached to said ring, e.g. in 2, 3 or 4 position; and is preferably in 3 or in 4 position.

A bridged cycloalkyl system includes bridged $(C_{5-12})$cycloalkyl, such as $(C_{6-8})$cycloalkyl, wherein the bridge optionally comprises a heteroatom, such as N, e.g. including cycloalkyl annelleted with another ring system, e.g. anellated with a $(C_{5-12})$cycloalkyl, such as decalin and/or phenyl, e.g. including decalin bridged by alkyl, e.g. methyl, such as adamantyl,
cyclohexyl or cycloheptyl, bridged by $(C_{1-4})$alkyl, e.g. bridged by a —$CH_2$— $CH_2$— group,
cycloheptyl or cyclooctyl bridged by an amine group,
cyclohexyl or cycloheptyl bridged by an alkyl chain, e.g. $(C_{2-4})$alkyl chain interrupted by a hetero atom, such as nitrogen, e.g. a —$CH_2$—NH—$CH_2$— group,
cycloheptyl bridged by an alkyl chain, e.g. $(C_{2-4})$alkyl chain, which is interrupted by a hetero atom, such as nitrogen, e.g. a —$CH_2$—NH—$CH_2$— group and which bridged cycloheptyl is further annelleted with phenyl.

A bridged substituted bridged heterocyclic system includes a bridged piperidine, e.g. bridged by $(C_{1-4})$alkylene, such as ethylene.

Naphthyl includes e.g. naph-1-yl, naphth-2-yl, e.g. unsubstituted or substituted by di$(C_{1-4})$alkylamino. Thiophenyl, includes e.g. thiophen-2-yl and thiophen-3-yl, e.g. substituted by 1 to 3 halogen. Benzthiazolyl, e.g. includes benzthiazol-2-yl, e.g. substituted by $(C_{1-4})$alkoxy. Chromanyl, e.g. includes chroman-6-yl, e.g, substituted by $(C_{1-4})$alkyl. Pyridine includes pyridine substituted by halogen and is bound to the (optionally $(CH_2)_{m\ or\ n}$)carbonyl or (optionally $(CH_2)_{m\ or\ n}$)sulfonyl group in a compound of formula I via a carbon atom.

In another aspect the present invention provides a compound of formula I, wherein at least one of
$R_4$ and $R_5$ together with the carbon atom to which they are attached,
$R_9$ and $R_{10}$ together with the carbon atom to which they are attached,
$R_{11}$ and $R_{12}$ together with the carbon atom to which they are attached,
$R_{16}$ and $R_{17}$ together with the carbon atom to which they are attached,
$R_6$,
$R_7$,
$R_{14}$, or
$R_{15}$ is a substituted bridged cycloalkyl system, and the other substitutents are as defined above, such as a compound of formula $I_{P3}$, $I_{P4}$, $I_{P5}$, $I_{P11}$, or $I_{P12}$ as defined below.

In another aspect the present invention provides a compound of formula I, wherein at least one of
$R_4$ and $R_5$ together with the carbon atom to which they are attached,
$R_9$ and $R_{10}$ together with the carbon atom to which they are attached,
$R_{11}$ and $R_{12}$ together with the carbon atom to which they are attached, or
$R_{16}$ and $R_{17}$ together with the carbon atom to which they are attached,
$R_6$,
$R_7$,
$R_{14}$, or
$R_{15}$ is substituted $(C_{4-8})$cycloalkyl, and the other subsbtutents are as defined above, such as a compound of formula $I_{P2}$, $I_{P6}$, $I_{P7}$ or $I_{P10}$ as defined below.

In another aspect the present invention provides a compound of formula I, wherein at least one of
$R_4$ and $R_5$ together with the carbon atom to which they are attached,
$R_9$ and $R_{10}$ together with the carbon atom to which they are attached,
$R_{11}$ and $R_{12}$ together with the carbon atom to which they are attached, or
$R_{16}$ and $R_{17}$ together with the carbon atom to which they are attached,
$R_6$,
$R_7$,
$R_{14}$, or
$R_{15}$ is substituted piperidine, substituted tetrahydropyridine, or a substituted bridged heterocyclic system, and, if m is other than 0 and/or n is other than 0, additionally may be piperazine, and the other substitutents are as defined above, such as a compound of formula $I_{P1}$, $I_{P4}$, $I_{P5}$, $I_{P8}$, $I_{P9}$, $I_{P12}$, $I_{P13}$ or $I_{P14}$—as defined below.

In another aspect the present invention provides a compound of formula I which is a compound of formula

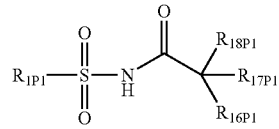

$I_{P1}$ wherein $R_{1P1}$ has the meaning as defined in $R_1$ above, and $R_{16P1}$ and $R_{17P1}$ together with the carbon atom to which they are attached are substituted piperidine or substituted tetrahydropyridine, wherein the substituents are as defined above for substituted piperidine.

In a compound of formula $I_{P1}$ preferably
$R_{1P1}$ is substituted or unsubstituted thienyl, benzthiazolyl, chromanyl, phenyl or naphthyl,
$R_{16P1}$ and $R_{17P1}$ together with the carbon atom to which they are attached are piperidine or tetrahydropyridine, preferably piperidine, substituted
a) at the nitrogen atom of the ring by substituents selected from the group consisting of
$(C_{1-6})$alkoxycarbonyl, e.g. BOC (i.e. tert.butoxycarbonyl),
$(C_{1-6})$alkoxycarbonyl$(C_{1-4})$alkyl, e.g. tert.butoxycarbonylmethyl,
unsubstituted or substituted phenyl, wherein the substituents are as defined for phenyl above,
$(C_{1-6})$alkylcarbonyl or phenylcarbonyl, $(C_{3-8})$cycloalkyl$(C_{1-4})$alkylcarbonyl,
heterocyclyl, e.g. pyridine, such as pyridin-2-yl, e.g. substituted by nitro, more preferably piperidine substituted at the nitrogen atom by BOC, or unsubstituted or substituted phenyl, and optionally b) further substituted at a carbon atom of the ring by (C$_{1-4}$)alkyl, and R$_{18P1}$ is hydrogen, phenyl or (C$_{1-4}$)alkyl, more preferably hydrogen or phenyl.

In another aspect the present invention provides a compound of formula I which is a compound of formula

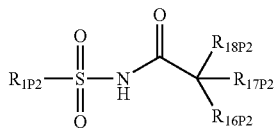

I$_{P2}$ wherein R$_{1P2}$ has the meaning of R$_1$ as defined above, R$_{16P2}$ and R$_{17P2}$ together with the carbon atom to which they are attached are substituted (C$_{4-7}$)cycloalkyl, wherein the substituents are as defined above for substituted cycloalkyl, and R$_{18P2}$ has the meaning of R$_{18}$ as defined above.

In a compound of formula I$_{P2}$ preferably

R$_{1P2}$ is substituted or unsubstituted phenyl, naphthyl, alkenyl (e.g. substituted by phenyl), or thienyl.

R$_{16P2}$ and R$_{17P2}$ together with the carbon atom to which they are attached are cyclohexyl substituted by
(C$_{1-6}$)alkoxycarbonylamino(C$_{1-4}$)alkyl, (C$_{1-6}$)alkoxycarbonylamino, (C$_{1-6}$)alkoxycarbonyl-((C$_{1-4}$)alkyl)amino, (C$_{1-6}$)alkoxycarbonyl((C$_{2-4}$)alkenyl)amino, (C$_{3-8}$)cycloalkylcarbonyl-((C$_{1-4}$)alkyl)amino, (C$_{3-8}$) cycloalkylcarbonylamino(C$_{1-4}$)alkyl, (C$_{1-6}$)alkylcarbonylamino-(C$_{1-4}$)alkyl, (C$_{3-8}$)cycloalkyl(C$_{1-4}$) alkyl-carbonyloxy, (C$_{3-8}$)cycloalkyl(C$_{1-4}$) alkylcarbonyloxy, (C$_{3-8}$)cycloalkyl((C$_{1-4}$)alkyl) aminocarbonyl, phenylcarbonyl, or heterocyclyl having 5- or 6-ring members and 1 to 4 heteroatoms selected from N,O, S, e.g. oxadiazolyl, more preferably substituted by (C$_{1-6}$)alkoxycarbonylamino(C$_{1-4}$) alkyl or (C$_{1-6}$)alkoxycarbonylamino, R$_{18P2}$ is hydrogen In another aspect the present invention provides a compound of formula I which is a compound of formula

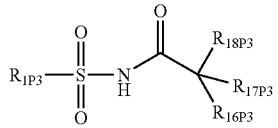

I$_{P3}$ wherein R$_{1P3}$ has the meaning of R$_1$ as defined above, R$_{16P3}$ and R$_{17P3}$ together with the carbon atom to which they are attached are a substituted bridged cycloalkyl ring system, wherein the substituents are as defined above for a bridged cycloalkyl ring system, and R$_{18P3}$ has the meaning of R$_{18}$ as defined above.

In a compound of formula I$_{P3}$ preferably

R$_{1P3}$ is unsubstituted or substituted phenyl or thienyl.

R$_{16P3}$ and R$_{17P3}$ together with the carbon atom to which they are attached are a bridged cycloalkyl ring system which is substituted by
(C$_{4-12}$)alkyl,
(C$_{1-6}$)alkyl, substituted by hydroxy, phenyl,
unsubstituted phenyl and substituted phenyl, wherein the substituents are as defined above for substituted phenyl,
(C$_{1-6}$)alkoxycarbonylamino, e.g. tert.butoxycarbonylamino,
(C$_{1-6}$)alkoxycarbonyl(C$_{1-6}$)alkyl,
(C$_{3-8}$)cycloalkylcarbonyl(C$_{1-6}$)alkyl,
(C$_{3-8}$)cycloalkoxycarbonyl(C$_{1-6}$)alkyl,
(C$_{1-6}$)alkylcarbonyl wherein alkyl is unsubstituted or substituted, e.g. by hydroxy,
(C$_{3-8}$)cycloalkyl,
(C$_{3-8}$)cycloalkylamino(C$_{1-6}$)alkyl, more preferably substituted by (C$_{1-6}$)alkoxycarbonyl, such as BOC, (C$_{4-8}$)alkyl, such as pentyl or (C$_{1-6}$)alkoxycarbonylamino, e.g. tert.butoxycarbonylamino.

R$_{18P3}$ is hydrogen, such as a compound of formula

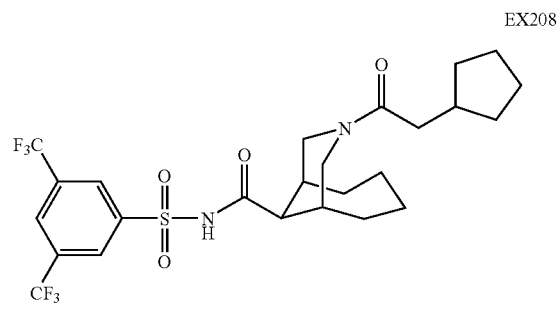

EX208 or of formula

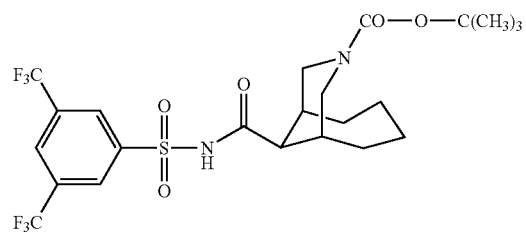

including pure isomers of formula

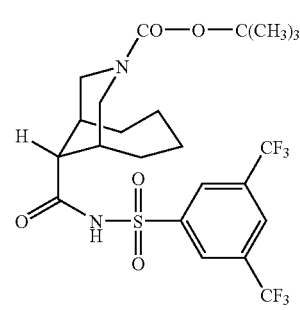

EX217 and

-continued

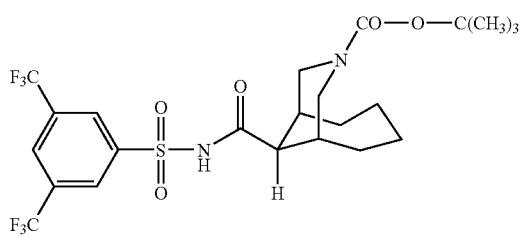
EX218 and mixtures thereof.
Compounds comprising a group of formula

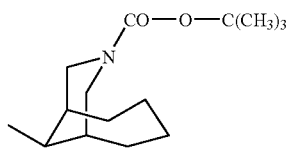

normally are obtained in the configuration of a compound of formula EX217.

In another aspect the present invention provides a compound of formula I which is a compound of formula

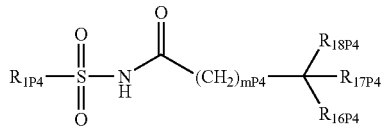
$I_{P4}$ wherein
$R_{1P4}$ has the meaning of $R_1$ as defined above, $R_{16P4}$ and $R_{17P4}$ together with the carbon atom to which they are attached are a substituted bridged cycloalkyl ring system or substituted piperidine, a substituted bridged heterocyclic system, substituted piperazine, or substituted tetrahydropyridine, wherein the substitutents are as defined above for corresponding groups and wherein piperazine is substituted by groups as defined for substituted piperidine above,
$R_{18P4}$ has the meaning of $R_{18}$ as defined above, and
$m_{P4}$ is 1, 2, 3 or 4.

In a compound of formula $I_{P4}$ preferably
$R_{1P4}$ is unsubstituted or substituted phenyl or thienyl.
$R_{16P4}$ and $R_{17P4}$ together with the carbon atom to which they are attached are a substituted bridged cycloyalkyl ring system, substituted piperidine or substituted bridged piperidine, more preferably a substituted bridged cycloyalkyl ring system or substituted piperidine, wherein substitutents are selected from
  a) $C_{1-6}$)alkoxycarbonyl, e.g. BOC,
     ($C_{1-6}$)alkoxycarbonyl($C_{1-4}$)alkyl, e.g. tert.butoxycarbonylmethyl,
     ($C_{1-4}$)alkylcarbonyloxy($C_{1-4}$)alkyl, e.g. unsubstituted or substituted by phenyl,
     unsubstituted or substituted phenyl, wherein the substituents are as defined above for phenyl,
     ($C_{1-6}$)alkylcarbonyl or phenylcarbonyl,
     ($C_{3-8}$)cycloalkyl($C_{1-4}$)alkylcarbonyl, heterocyclyl, e.g. pyridine, such as pyridin-2-yl, e.g. substituted by nitro, and optionally
  b) ($C_{1-4}$)alkyl at a carbon atom of a ring,
more preferably substitutents are selected from ($C_{1-6}$)alkoxycarbonyl, e.g. BOC, phenyl, unsubstituted phenyl and substituted phenyl, e.g. substituted by groups as defined above for substituted phenyls, such as nitro, ($C_{1-4}$)alkyl, ($C_{1-4}$)haloalkyl, e.g. trifluoromethyl, aminocarbonyl.
$R_{18P4}$ is hydrogen or hydroxy, more preferably hydrogen.
$m_{P4}$ is 1, such as compounds of formula

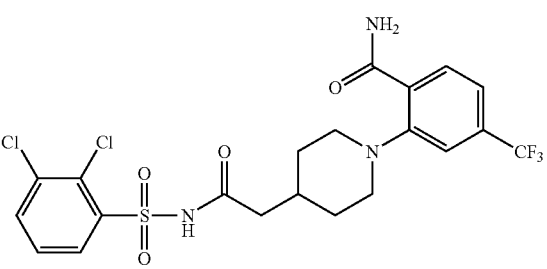
EX248 or of formula

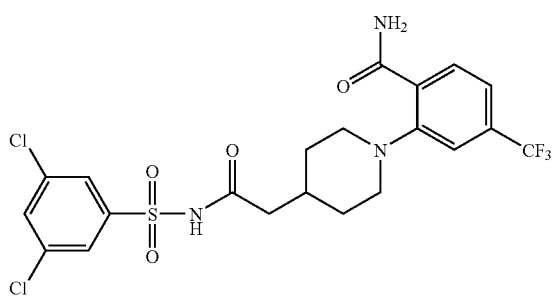
EX249 or of formula

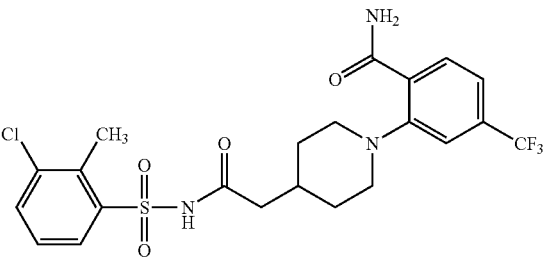
EX251

In another aspect the present invention provides a compound of formula I which is a compound of formula

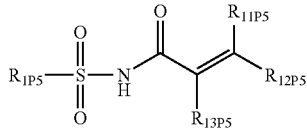

wherein
$R_{1P5}$ has the meaning of $R_1$ as defined above,
$R_{13P5}$ has the meaning of $R_{13}$ as defined above, and
$R_{11P5}$ and $R_{12P5}$ together with the carbon atom to which they are attached have the meaning of $R_{11}$ and $R_{12}$ as defined above.

In a compound of formula $I_{P5}$ preferably
$R_{1P5}$ is unsubstituted or substituted phenyl or thienyl.
$R_{11P5}$ and $R_{12P5}$ together with the carbon atom to which they are attached are piperidine, methylpiperidine or a bridged cyclolalkyl ring system substituted by $(C_{1-6})$alkoxycarbonyl, e.g. tert.butoxycarbonyl;
unsubstituted or substituted phenyl, wherein the substituents are as defined above for phenyl,
$(C_{1-8})$alkylcarbonyloxy, such as tert.butyl-methylcarbonyloxy, more preferably substitutents are selected from $(C_{1-8})$alkoxycarbonyl, such as BOC, or $(C_{1-6})$alkyl-carbonyloxy, such as tert.butylmethylcarbonyloxy,
$R_{3P5}$ is hydrogen, halogen or cyano.

In another aspect the present invention provides a compound of formula I which is a compound of formula

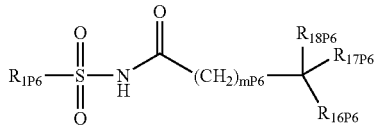

wherein
$R_{1P6}$ has the meaning of $R_1$ as defined above,
$R_{16P6}$ and $R_{17P6}$ together with the carbon atom to which they are attached are substituted $(C_{4-8})$cycloalkyl,
$R_{18P6}$ has the meaning of $R_{18}$ as defined above, and
$m_{P6}$ is 1, 2, 3 or 4.

In a compound of formula $I_{P6}$ preferably
$R_{1P6}$ is unsubstituted or substituted phenyl or thienyl.
$R_{16P6}$ and $R_{17P6}$ together with the carbon atom to which they are attached are cyclohexyl, substituted by $(C_{1-6})$alkoxycarbonyloxy or $(C_{1-6})$alkoxycarbonylamino.
$m_{P6}$ is 1.

In another aspect the present invention provides a compound of formula I which is a compound of formula

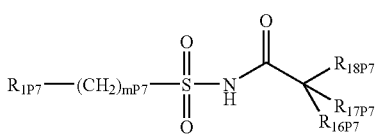

wherein
$R_{1P7}$ has the meaning of $R_1$ as defined above,
$R_{16P7}$ and $R_{17P7}$ together with the carbon atom to which they are attached are substituted $(C_{4-8})$cycloalkyl,
$R_{18P7}$ has the meaning of $R_{18}$ as defined above, and
$m_{P7}$ is 1, 2, 3 or 4.

In a compound of formula $I_{P7}$ preferably
$R_{1P7}$ is unsubstituted or substituted phenyl,
$R_{16P7}$ and $R_{17P7}$ together with the carbon atom to which they are attached are cyclohexyl substituted by $(C_{1-6})$alkoxycarbonylamino$(C_{1-4})$alkyl, or $(C_{1-6})$alkoxycarbonylamino, wherein the amine group is optionally further substituted by $(C_{1-4})$alkyl.
$R_{18P7}$ is hydrogen, and
$m_{P7}$ is 1.

In another aspect the present invention provides a compound of formula I which is a compound of formula

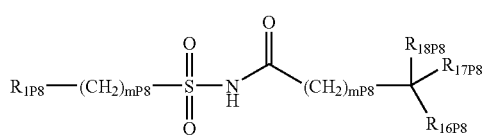

wherein
$R_{1P8}$ has the meaning of $R_1$ as defined above,
$R_{16P8}$ and $R_{178}$ together with the carbon atom to which they are attached are substituted piperidine, tetrahydropyridine or piperazine, wherein the substitutents are as defined above for piperidine,
$R_{16P8}$ has the meaning of $R_{18}$ as defined above,
$m_{P8}$ is 1 and $n_{P8}$ is 1, In a compound of formula $I_{P8}$ preferably
$R_{1P8}$ is unsubstituted or substituted phenyl,
$R_{16P8}$ and $R_{17P8}$ together with the carbon atom to which they are attached are piperidine substituted by $(C_{1-6})$alkoxycarbonyl.
$R_{18P8}$ is hydrogen.
$m_{P8}$ is 1.
$n_{P8}$ is 1.

In another aspect the present invention provides a compound of formula I, which is a compound of formula

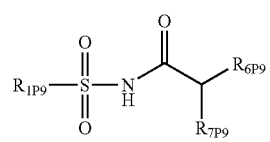

wherein $R_{1P9}$, $R_{6P9}$ and $R_{7P9}$ have the index-number corresponding meaning meaning of $R_1$, $R_6$ and $R_7$ defined above.

In a compound of formula $I_{P9}$ preferably
$R_{1P9}$ is unsubstituted or substituted phenyl,
$R_{6P9}$ and $R_{7P9}$ independently of each other are $(C_{1-6})$haloalkyl, unsubstituted or substituted phenyl, piperidinyl substituted by $(C_{3-8})$cyclyolalkylaminocarbonyl or $(C_{1-6})$alkoxycarbonyl, or amino substituted by substituted piperidine.

In another aspect the present invention provides a compound of formula

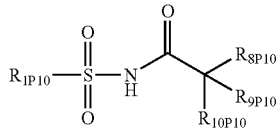

$I_{P10}$ wherein
wherein $R_{1P10}$ has the meaning meaning of $R_1$,
$R_{8P10}$ an has the meaning meaning of $R_8$, and
$R_{9P10}$ and $R_{10P10}$ together with the carbon atom to which they are attached are $(C_{4-8})$cycloalkyl.
In a compound of formula $I_{P10}$ preferably
$R_{1P10}$ is substituted or unsubstituted phenyl.
$R_{8P10}$ is piperidine substituted by $(C_{1-6})$alkoxycarbonyl or unsubstituted or substituted phenyl.
$R_{9P10}$ and $R_{10P10}$ together with the carbon atom to which they are attached are $(C_{4-7})$cycloalkyl.

In another aspect the present invention provides a compound of formula I, which is a compound of formula

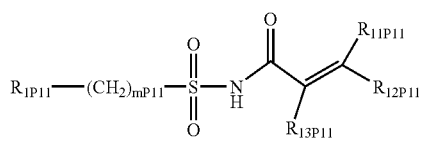

$I_{P11}$ wherein
$R_{1P11}$ has the meaning meaning of $R_1$,
$R_{11P11}$ and $R_{12P11}$ together with the carbon atom to which they are attached have the meaning of $R_{11}$ and $R_{12}$ together with the carbon atom to which they are attached,
$R_{13P11}$ has the meaning meaning of $R_{13}$, and
$m_{P11}$ is 1, 2, 3 or 4.
In a compound of formula $I_{P11}$ preferably
$R_{1P11}$ is substituted or unsubstituted phenyl.
$R_{11P11}$ and $R_{12P11}$ together with the carbon atom to which they are attached are a substituted bridged cycloalkyl ring system.
$m_{P11}$ is 1.

In another aspect the present invention provides a compound of formula I, which is a compound of formula

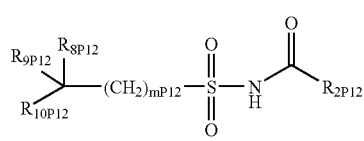

$I_{P12}$ wherein
$R_{2P12}$ has the meaning of $R_8$ as defined above and additionally is unsubstituted or substituted $(C_{6-18})$aryl wherein substituents are as defined above for aryl-substituents,
$R_{8P12}$ has the meaning of $R_8$ as defined above,
$R_{9P12}$ and $R_{10P12}$ have the meaning of $R_9$ and $R_{10}$ as defined above, and
$m_{P12}$ is 1, 2, 3 or 4.

In a compound of formula $I_{P12}$ preferably
$R_{2P12}$ is substituted or unsubstituted phenyl.
$R_{8P12}$ is hydrogen or hydroxy.
$R_{9P12}$ and $R_{10P12}$ together with the carbon atom to which they are attached are
A) piperidine substituted at the nitrogen atom of the ring by $(C_{1-6})$alkoxycarbonyl, $(C_{3-8})$cycloalkyl$(C_{1-4})$alkylcarbonyl, or unsubstituted or substituted phenyl,
B) a bridged cycloalkyl ring system substituted by oxo, e.g. and $(C_{1-4})$alkyl.
$m_{P12}$ is 1, such as a compound of formula

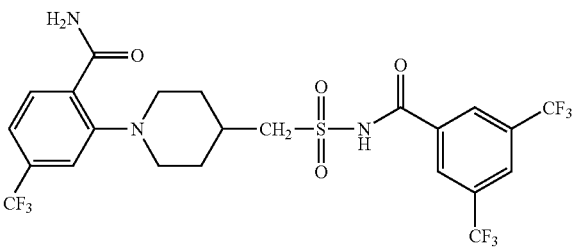

In another aspect the present invention provides a compound of formula

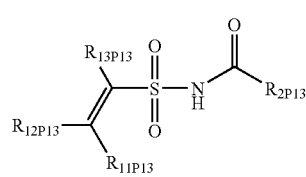

$I_{P13}$ wherein
$R_{2P13}$ has the meaning of $R_2$ as defined above, and additionally is unsubstituted or substituted $(C_{6-18})$aryl wherein substituents are as defined above for aryl-substituents,
$R_{11P13}$ and $R_{12P13}$ have the meaning of $R_{11}$ and $R_{12}$ as defined above, and
$R_{13P13}$ has the meaning of $R_{13}$ as defined above.
In a compound of formula $I_{P13}$ preferably
$R_{2P13}$ is unsubstituted or substituted phenyl.
$R_{11P13}$ and $R_{12P13}$ together with the carbon atom to which they are attached are piperidine substituted by unsubstituted or substituted phenyl, or substituted by $(C_{1-6})$alkoxyCarbonyl.
$R_{13P13}$ is hydrogen.

In another aspect the present invention provides a compound of formula I, which is a compound of formula

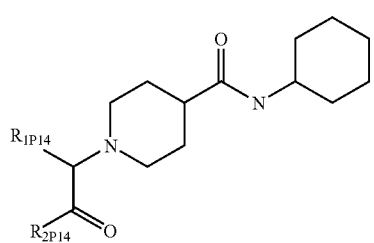

$I_{P14}$ wherein $R_{1P14}$ is $(C_{6-18})$aryl, and $R_{2P14}$ is $(C_{6-18})$arylsulfondioxideamino.

In a compound of formula $I_{P14}$ preferably $R_{1P14}$ is phenyl substituted by trifluoromethyl or halogen, and $R_{2P14}$ is $(C_{3-18})$arylsulfondioxideamino, such as phenylsulfondioxideamino, unsubstituted or substituted by $(C_{1-6})$alkyl, or halogen$(C_{1-3})$alkyl, $(C_{1-3})$alkoxy, halogen$(C_{1-3})$alkoxy, or halogen.

A compound of formula I includes a compound of formula $I_{P1}$, $I_{P2}$, $I_{P3}$, $I_{P4}$, $I_{P5}$, $I_{P6}$, $I_{P7}$, $I_{P8}$, $I_{P9}$, $I_{P10}$, $I_{P11}$, $I_{P12}$, $I_{P13}$ and $I_{P14}$. Compounds provided by the present invention are hereinafter designated as "compound(s) of the present invention". A compound of the present invention includes a compound in any form, e.g. in free form, in the form of a salt, in the form of a solvate and in the form of a salt and a solvate. In a compound of the present invention substituents indicated are unsubstituted, if not otherwise (specifically) defined.

Each single substituent defined above in a compound of formula I may be per se a preferred substituent, independently of the other substituents defined.

In another aspect the present invention provides a compound of the present invention in the form of a salt, e.g. and in the form of a salt and in the form of a solvate, or in the form of a solvate.

A salt of a compound of the present invention includes a pharmaceutically acceptable salt, e.g. including a metal salt, an acid addition salt or an amine salt. Metal salts include for example alkali or earth alkali salts; acid addition salts include salts of a compound of formula I with an acid, e.g. HCl; amine salts include salts of a compound of formula I with an amine.

A compound of the present invention in free form may be converted into a corresponding compound in the form of a salt; and vice versa. A compound of the present invention in free form or in the form of a salt and in the form of a solvate may be converted into a corresponding compound in free form or in the form of a salt in unsolvated form; and vice versa.

A compound of the present invention may exist in the form of isomers and mixtures thereof. A compound of the present invention may e.g. contain asymmetric carbon atoms and may thus exist in the form of diastereoisomeres and mixtures thereof. Substituents in a non-aromatic ring may be in the cis or in the trans configuration in respect to each other. E.g. if $R_1$ or $R_2$ includes a substituted piperidine or tetrahydropyridine which is additionally substituted by a further substitutent at a carbon atom of said ring, said further substitutent may be in the cis or in the trans configuration with respect to the (optionally —$(CH_2)_m$— or —$(CH_2)_n$)sulfonamide group also attached to said piperidine or tetrahydropyridine; and if $R_1$ or $R_2$ includes a substituted cyclohexyl, said substitutent may be in the cis or in trans configuration with respect to the (optionally —$(CH_2)_m$— or —$(CH_2)_n$)sulfonamide group also attached to said cyclohexyl ring. Isomeric mixtures may be separated as appropriate, e.g. according to a method as conventional, to obtain pure isomers. The present invention includes a compound of the present invention in any isomeric form and in any isomeric mixture.

Any compound described herein, e.g. a compound of the present invention, may be prepared as appropriate, e.g. according, e.g. analogously, to a method as conventional, e.g. or as specified herein.

In another aspect the present invention provides a process for the production of a compound of formula I comprising reacting a compound of formula

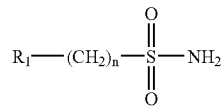

wherein $R_1$ and n are as defined above, with a compound of formula

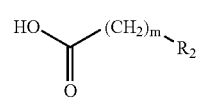

wherein $R_2$ and m are as defined above, e.g. in an activated form, e.g. and/or in the presence of a coupling agent; and isolating a compound of formula I, wherein $R_1$, $R_2$, m and n are as described above from the reaction mixture obtained, e.g. if a compound of formula I comprises a group of formula II or of formula V, a compound of formula VIII may be reacted a compound of formula

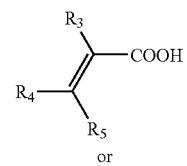

or

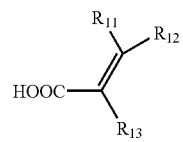

wherein the substituents are as defined above, e.g. in an activated form, e.g. and/or in the presence of a coupling agent, to obtain a compound of formula I, wherein the substitutents are as defined above.

The above reaction is an acylation reaction and may be carried out as appropriate, e.g. in appropriate solvent and at appropriate temperatures, e.g. according, e.g. analogously, to a method as conventional or according, e.g. analogously, to a method as described herein.

If in a compound of formula I a piperidine, tetrahydropyridine or piperazine, or a bridged cycloalkyl ring system comprising a nitrogen atom in a bridge, is unsubstituted present, such ring may be e.g. substituted at the nitrogen atom, e.g. by acylation to introduce a carbonyl containing residue, e.g. or by reaction with a fluoro containing phenyl wherein fluoro acts as a leaving group for N-phenylation (similarly, a heterocyclyl group may be attached to the nitrogen with a corresponding heterocyclic ring which is substituted by chloro as a leaving group). An ester group obtained by a reaction step may be saponified to obtain a carboxylic acid group, or vice versa.

Compounds of formula VIII, IX, X and XI are known or may be obtained as appropriate, e.g. according, e.g. analogously, to a method as conventional or as described herein. A compound of formula VIII, for example may be obtained from a compound of formula

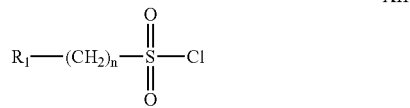

XII by treatment with (aqueous) $NH_3$.

A compound of formula X or XI may be obtained e.g. by reacting a compound $R_2$—H, wherein $R_2$ is a group of formula II or of formula V, which carries an oxo group at one of the carbon atoms of the (bridged) ring system, with (RO)$_2$OP—CHR$_x$—COO—R, wherein R is alkyl, such as (C$_{1-4}$)alkyl, e.g. methyl or ethyl and R$_x$ is R$_3$ or R$_8$ as defined above, in a solvent, e.g. tetrahydrofurane in the presence of a base e.g. sodium hydride; or Ph$_3$-P—CR$_x$—COO—C$_2$H$_5$, wherein R$_x$ is as defined above, in a solvent such as toluene, e.g. at temperatures above room temperature, or, if R$_x$ is hydrogen, by reaction with NC—CH$_2$—COOR, wherein R is as defined above, in a solvent, e.g. dimethylformamide, in the presence of a catalyst, e.g. piperidine and β-alanine, e.g. at temperatures above room temperature; and subsequent treatment of the compound obtained with NaOH or LiOH, in a solvent such as tetrahydrofurane/H$_2$O, e.g. at temperatures above room temperature.

Steroidal hormones in particular tissues are associated with several diseases, such as tumors of breast, endometrium and prostate and disorders of the pilosebaceous unit, e.g. acne, androgenetic alopecia, and hirsutism. Important precursors for the local production of these steroid hormones are steroid 3-O-sulfates which are desulfated by the enzyme steroid sulfatase in the target tissues. Inhibition of this enzyme results in reduced local levels of the corresponding active steroidal hormones, which is expected to be of therapeutic relevance. Furthermore, steroid sulfatase inhibitors may be useful as immunosuppressive agents, and have been shown to enhance memory when delivered to the brain.

Acne is a polyetiological disease caused by the interplay of numerous factors, such as inheritance, sebum, hormones, and bacteria. The most important causative factor in acne is sebum production; in almost all acne patients sebaceous glands are larger and more sebum is produced than in persons with healthy skin. The development of the sebaceous gland and the extent of sebum production is controlled honmonally by androgens; therefore, androgens play a crucial role in the pathogenesis of acne. In man, there are two major sources supplying androgens to target tissues: (i) the gonades which secrete testosterone, (ii) the adrenals producing dehydroepiandrosterone (DHEA) which is secreted as the sulfate conjugate (DHEAS). Testosterone and DHEAS are both converted to the most active androgen, dihydrotestosterone (DHT), in the target tissue, e.g. in the skin. There is evidence that these pathways of local synthesis of DHT in the skin are more important than direct supply with active androgens from the circulation. Therefore, reduction of endogeneous levels of androgens in the target tissue by specific inhibitors should be of therapeutic benefit in acne and seborrhoea. Furthermore, it opens the perspective to treat these disorders through modulation of local androgen levels by topical treatment, rather than influencing circulating hormone levels by systemic therapies.

Androgenetic male alopecia is very common in the white races, accounting for about 95% of all types of alopecia. Male-pattern baldness is caused by an increased number of hair follicles in the scalp entering the telogen phase and by the telogen phase lasting longer. It is a genetically determined hair loss effected through androgens. Elevated serum DHEA but normal testosterone levels have been reported in balding men compared with non-balding controls, implying that target tissue androgen production is important in androgenetic alopecia.

Hirsutism is the pathological thickening and strengthening of the hair which is characterized by a masculine pattern of hair growth in children and women. Hirsutism is androgen induced, either by increased formation of androgens or by increased sensitivity of the hair follicle to androgens. Therefore, a therapy resulting in reduction of endogeneous levels of androgens and/or estrogens in the target tissue (skin) should be effective in acne, androgeneuc alopecia and hirsutism.

As described above, DHT, the most active androgen, is synthesized in the skin from the abundant systemic precursor DHEAS and the first step in the metabolic pathway from DHEAS to DHT is desulfatation of DHEAS by the enzyme steroid sulfatase to produce DHEA. The presence of the enzyme in keratinocytes and in skin-derived fibroblasts has been described. The potential use of steroid sulfatase inhibitors for the reduction of endogenous levels of steroid hormones in the skin was confirmed using known steroid sulfatase inhibitors, such as estrone 3-O-sulfamate and 4-methylumbelliferyl-7-O-sulfamate. We have found that inhibitors of placental steroid sulfatase also inhibit steroid sulfatase prepared from either a human keratinocyte (HaCaT) or a human skin-derived fibroblast cell line (1BR3GN). Such inhibitors were also shown to block steroid sulfatase in intact monolayers of the HaCaT keratinocytes.

Therefore, inhibitors of steroid sulfatase may be used to reduce androgen and estrogen levels in the skin. They can be used as inhibitors of the enzyme steroid sulfatase for the local treatment of androgen-dependent disorders of the pilosebaceous unit (such as acne, seborrhoea, androgenetic alopecia, hirsubsm) and for the local treatment of squamous cell carcinoma.

Furthermore non-steroidal steroid sulfatase inhibitors are expected to be useful for the treatment of disorders mediated by the action of steroid hormones in which the steroidal products of the sulfatase cleavage play a role. Indications for these new kind of inhibitors include androgen-dependent disorders of the pilosebaceous unit (such as acne, seborrhea, androgenetic alopecia, hirsutism); estrogen- or androgen-dependent tumors, such as squamous cell carcinoma and neoplasms, e.g. of the breast, endometrium, and prostate; inflammatory and autoimmune diseases, such as rheumatoid arthritis, type I and II diabetes, systemic lupus erythematosus, multiple sclerosis, myasthenia gravis, thyroiditis, vasculitis, ulcerative colitis, and Crohn's disease, psoriasis, contact dermatitis, graft versus host disease, eczema, asthma and organ rejection following transplantation. Steroid sulfatase inhibitors are also useful for the treatment of cancer, especially for the treatment of estrogen- and androgen-dependent cancers, such as cancer of the breast and endometrium and squamous cell carcinoma, and cancer of the prostata. Steroid sulfatase inhibitors are also useful for the enhancement of cognitive function, especially in the treatment of senile dementia, including Alzheimer's disease, by increasing the DHEAS levels in the central nervous system.

Activities of compounds in inhibiting the activity of steroid sulfatase may be shown in the following test systems:

Purification of Human Steroid Sulfatase

Human placenta is obtained freshly after delivery and stripped of membranes and connective tissues. For storage, the material is frozen at −70° C. After thawing, all further steps are carried out at 4° C., while pH values are adjusted at 20° C. 400 g of the tissue is homogenized in 1.2 l of buffer A (50 mM Tris-HCl, pH 7.4, 0.25 M sucrose). The homogenate obtained is centrifuged at 10,000×g for 45 minutes. The supernatant is set aside and the pellet obtained is re-homogenized in 500 ml of buffer A. After centrifugation, the two supernatants obtained are combined and subjected to ultracentrifugation (100,000×g, 1 hour). The pellet obtained is resuspended in buffer A and centrifugation is repeated. The pellet obtained is suspended in 50 ml of 50 mM Tris-HCl, pH 7.4 and stored at −20° C. until further work-up.

After thawing, microsomes are collected by ultracentrifugation (as descrobed above) and are suspended in 50 ml of buffer B (10 mM Tris-HCl, pH 7.0, 1 mM EDTA, 2 mM 2-mercaptoethanol, 1% Triton X-100, 0.1% aprotinin). After 1 hour on ice with gentle agitation, the suspension is centrifuged (100,000×g, 1 hour). The supernatant containing the enzyme activity is collected and the pH is adjusted to 8.0 with 1 M Tris. The solution obtained is applied to a hydroxy apatite column (2.6×20 cm) and equilibrated with buffer B, pH 8.0. The column is washed with buffer B at a flow rate of 2 ml/min. The activity is recovered in the flow-through. The pool is adjusted to pH 7.4 and subjected to chromatography on a concanavalin A sepharose column (1.6×10 cm) equilibrated in buffer C (20 mM Tris-HCl, pH 7.4, 0.1% Triton X-100, 0.5 M NaCl). The column is washed with buffer C, and the bound protein is eluted with 10% methyl mannoside in buffer C. Active fractions are pooled and dialysed against buffer D (20 mM Tris-HCl, pH 8.0, 1 mM EDTA, 0.1% Triton X-100, 10% glycerol (v/v)).

The retentate obtained is applied to a blue sepharose column (0.8×10 cm) equilibrated with buffer D; which column is washed and elution is carried out with a linear gradient of buffer D to 2 M NaCl in buffer D. Active fractions are pooled, concentrated as required (Centricon 10), dialysed against buffer D and stored in aliquots at −20° C.

Assay of Human Steroid Sulfatase

It is known that purified human steroid sulfatase not only is capable to cleave steroid sulfates, but also readily cleaves aryl sulfates such as 4-methylumbelliferyl sulfate which is used in the present test system as an activity indicator. Assay mixtures are prepared by consecutively dispensing the following solutions into the wells of white microtiter plates:

1) 50 µl substrate solution (1.5 mM 4-methylumbelliferyl sulfate in 0.1 M Tris-HCl, pH 7.5)
2) 50 µl test compound dilution in 0.1 M Tris-HCl, pH 7.5, 0.1% Triton X-100 (stock solutions of the test compounds are prepared in DMSO; final concentrations of the solvent in the assay mixture not exceeding 1%)
3) 50 µl enzyme dilution (approximately 12 enzyme units/ml)

We define one enzyme unit as the amount of steroid sulfatase that hydrolyses 1 nmol of 4-methylumbelliferyl sulfate per hour at an initial substrate concentration of 500 µM in 0.1 M Tris-HCl, pH 7.5, 0.1% Triton X-100, at 37° C.

Plates are incubated at 37° C. for 1 hour. Then the reaction is stopped by addition of 100 µl 0.2 M NaOH. Fluorescence intensity is determined in a Titertek Fluoroskan II instrument with $\lambda_{ex}$=355 nm and $\lambda_{em}$=460 nm.

Calculation of Relative $IC_{50}$ Values

From the fluorescence intensity data (I) obtained at different concentrations (c) of the test compound in the human steroid sulfatase assay as described above, the concentration inhibiting the enzymatic activity by 50% ($IC_{50}$) is calculated using the equation:

$$I = \frac{I_{100}}{1 + (c/IC_{50})^s}$$

wherein $I_{100}$ is the intensity observed in the absence of inhibitor and s is a slope factor. Estrone sulfamate is used as a reference compound and its $IC_{50}$ value is determined in parallel to all other test compounds. Relative $IC_{50}$ values are defined as follows:

$$\text{rel } IC_{50} = \frac{IC_{50} \text{ of test compound}}{IC_{50} \text{ of estrone sulfamate}}$$

According to our testing and calculation estrone sulfamate shows an $IC_{50}$ value of approximately 60 nM.

The compounds of the present invention show activity in that described assay (rel $IC_{50}$ in the range of 0.0046 to 10).

CHO/STS Assay

CHO cells stably transfected with human steroid sulfatase (CHO/STS) are seeded into microtiter plates. After reaching approximately 90% confluency, they are incubated overnight with graded concentrations of test substances (e.g. compounds of the present invention). They are then fixed with 4% paraformaldehyde for 10 minutes at room temperature and washed 4 times with PBS, before incubation with 100 µl/well 0.5 mM 4-methylumbelliferyl sulfate (MUS), dissolved in 0.1 M Tris-HCl, pH 7.5. The enzyme reaction is carried out at 37° C. for 30 minutes. Then 50 µl/well stop solution (1M Tris-HCl, pH 10.4) are added. The enzyme reaction solutions are transferred to white plates (Microfluor, Dynex, Chantilly, Va.) and read in a Fluoroskan II fluorescence microtiter plate reader. Reagent blanks are subtracted from all values. For drug testing, the fluorescence units (FU) are divided by the optical density readings after staining cellular protein with sulforhodamine B ($OD_{550}$), in order to correct for variations in cell number. $IC_{50}$ values are determined by linear interpolation between two bracketing points. In each assay with inhibitors, estrone 3-O-sulfamate is run as a reference compound, and the $IC_{50}$ values are normalized to estrone 3-O-sulfamate (relative $IC_{50}$=$IC_{50}$ compound/$IC_{50}$ estrone 3-O-sulfamate).

The compounds of the present invention show activity in that described assay (rel $IC_{50}$ in the range of 0.05 to 10).

Assay Using Human Skin Homogenate

Frozen specimens of human cadaver skin (about 100 mg per sample) are minced into small pieces (about 1×1 mm) using sharp scissors. The pieces obtained are suspended in ten volumes (w/w) of buffer (20 mM Tris-HCl, pH 7.5), containing 0.1% Triton X-100. Test compounds (e.g. compounds of the present invention) are added at graded concentrations from stock solutions in ethanol or DMSO. Second, DHEAS as the substrate is added (1 µC/ml [$^3$H]DHEAS, specific activity: about 60 Cl/mmol, and 20 µM unlabeled DHEAS). Samples are incubated for 18 hrs at 37° C. At the end of the incubation period, 50 µl of 1 M Tris, pH 10.4 and 3 ml of toluene are added. A 1-ml aliquot of the organic phase is removed and subjected to liquid scintillation counting. The determined dpm-values in the aliquots are converted to nmol of DHEA cleaved per g of skin per hour.

The compounds of the present invention show activity in that described assay ($IC_{50}$ in the range of 0.03 to 10 μM).

The compounds of the present invention show activity in test systems as defined above. A compound of the present invention in salt and/or solvate form exhibits the same order of activity as a compound of the present invention in free and/or non-solvated form. The compounds of the present invention are therefore indicated for use as steroid sulfatase inhibitor in the treatment of disorders mediated by the action of steroid sulfatase, e.g. including androgen-dependent disorders of the pilosebaceous unit, such as acne, seborrhea, androgenetic alopecia, hirsutism; cancers, such as estrogen and androgen-dependent cancers; and cognitive dysfunctions, such as senile dementia including Alzheimer's disease. Treatment includes therapeutical treatment and prophylaxis.

Preferred compounds of the present invention include a compound of Example 208, a compound of Example 217 and Example 218, a compound of Example 248, a compound of Example 249, a compound of Example 251, and a compound of Example 379. These compounds show in the Human Steroid Sulfatase Assay a rel $IC_{50}$ in the range of 0.0046 to 0.29, in the CHO/STS Assay a rel $IC_{50}$ in the range of 0.05 to 0.18, and in the Assay Using Human Skin Homogenate of an $IC_{50}$ in the range of 0.03 to 0.27 μM and are thus highly active steroid sulfatase inhibitors. Even more preferred is the compound of Example 217 and Example 218, which show in the Assay of Human Steroid Sulfatase a rel $IC_{50}$ of 0.29, in the CHO/STS Assay a rel $IC_{50}$ of 0.08 and in the Assay Using Human Skin Homogenate an $IC_{50}$ of 0.27 μM.

In another aspect the present invention provides a compound of formula I for use as a pharmaceutical, e.g. in the treatment of disorders mediated by the action of steroid sulfatase.

In a further aspect the present invention provides a compound of formula I for use in the preparation of a medicament for treatment of disorders mediated by the action of steroid sulfatase.

In another aspect the present invention provides a method of treating disorders mediated by the action of steroid sulfatase comprising administering a therapeutically effective amount of a compound of formula I to a subject in need of such treatment.

For such use the dosage to be used will vary, of course, depending e.g. on the particular compound employed, the mode of administration and the treatment desired. However, in general, satisfactory results may be obtained if the compounds are administered at a daily dose of from about 0.1 mg/kg to about 100 mg/kg animal body weight, e.g. conveniently administered in divided doses two to four times daily. For most large mammals the total daily dosage is from about 5 mg to about 5000 mg, conveniently administered, for example, in divided doses up to four times a day or in retarded form. Unit dosage forms comprise, e.g. from about 1.25 mg to about 2000 mg of a compound of a present invention in admixture with at least one pharmaceutically acceptable excipient, e.g. carrier, diluent.

The compounds of the present invention may be administered in the form of a pharmaceutically acceptable salt, e.g. an acid addition salt, metal salt, amine salt; or in free form; optionally in the form of a solvate.

The compounds of the present invention may be administered in similar manner to known standards for use in such indications. The compounds of the present invention may be admixed with conventional, e.g. pharmaceutically acceptable, excipients, such as carriers and diluents and optionally further excipients. The compounds of the present invention may be administered, e.g. in the form of pharmaceutical compositions,
orally, e.g. in the form of tablets, capsules;
parenterally, intravenously, e.g. in the form of liquids, such as solutions, suspensions;
topically, e.g. in the form of ointments, creams.

The concentrations of the active substance in a pharmaceutical composition will of course vary, e.g. depending on the compound used, the treatment desired and the nature of the composition used. In general, satisfactory results may be obtained at concentrations of from about 0.05 to about 5% such as from about 0.1 to about 1% w/w in topical compositions, and by about 1% w/w to about 90% w/w in oral, parenteral or intravenous compositions.

In another aspect the present invention provides a pharmaceutical composition comprising a pharmaceutically effective amount of at least one compound of the present invention in association with at least one pharmaceutically acceptable excipient.

A pharmaceutical composition of the present invention may comprise as an active ingredient one or more compounds of the present invention, e.g. at least one, and one or more other pharmaceutically active agents. At least one compound of the present invention thus may be used for pharmaceutical treatment alone, or in combination with one or more further pharmaceutically active agents. Such further pharmaceutically active agents include e.g. retinoids, e.g. retinoic acid, such as isotretinoin; tretinoin (Roche); adapalene (6-[3-(1-adamantyl)-4-methoxyphenyl]-2-naphthoic acid); oral contraceptives, e.g. 19- nor-17a-pregna-1,3,5(10)-trien-20-in-3, 17-diol, 6-Chlor-17-hydroxy-1a,2a-methylen-4,6-pregnadien-3,20-dion, such as Diane® (Schering), antibacterials, such as erythromycins, including erythromycin A, azithromycin, clarithromycin, roxythromycin; tetracyclines, lincosamid-antibiotics, such as clindamycin (methyl 7-chlor-6,7,8-tridesoxy-6-(trans-1-methyl-4-propyl-L-2-pyrrolidin-carboxamido)-1-thio-L-threo-a-D-galacto-octopyranosid), azelaic acid (nonanedionic acid), nadifloxacin; benzoyl peroxide.

Combinations include
fixed combinations, in which two or more pharmaceutically active agents are in the same pharmaceutical composition,
kits, in which two or more pharmaceutically active agents in separate compositions are sold in the same package, e.g. with instruction for co-administration; and
free combinations in which the pharmaceutically active agents are packaged separately, but instruction for simultaneous or sequential administration are given.

In another aspect the present invention provides a compound of the present invention in combination with at least one other pharmaceutically effective agent for use as a pharmaceutical, such as a pharmaceutical composition comprising a combination of at least one compound of the present invention with at least one other pharmaceutically effective agent in association with at least one pharmaceutical acceptable excipient.

In the following examples all temperatures are in degree Centigrade and are uncorrected.

The following abbreviations are used:
DIEA: diisopropylethylamine
DMA: N,N-dimethylacetamide
DMAP: N,N-dimethylaminopyridine
DMF: N,N-dimethylformamide
DMSO: dimethylsulfoxide EDC: 1-ethyl-3-(3'-dimethylaminopropyl)carbodiimide in the form of a hydrochloride
EtAc: ethyl acetate
EX: Example
HEX: n-hexane
c-HEX: cyclohexane
m.p.: melting point
PPA: propanephosphonic acid anhydride
RT: room temperature
THF: tetrahydrofurane Procedures

EXAMPLE A 4-(4-Bromo-2,5-dichloro-thiophene-3-sulfonylaminocarbonyl)-piperidine-1-carboxylic acid tert.-butyl ester (compound of Example 1)

a. 4-Bromo-2,5-dichloro-thiophene-3-sulfonamide 90 ml of an aqueous solution of $NH_3$ (32%) is added at room temperature to a solution of 8.88 g of 4-bromo-2,5-dichloro-thiophene-3-sulfonylchloride in 120 ml of EtAc. The mixture obtained is stirred for ca. 15 hours. Two phases obtained are separated, the organic layer is washed with 1 N HCl and $H_2O$, and dried. Solvent of the organic phase obtained is evaporated. 4-Bromo-2,5-dichloro-thiophene-3-sulfonamide is obtained in the form of a white powder. m.p. 113-117°; $^{13}C$—NMR ($CDCl_3$): δ=108.287; 125.342; 130.404; 135.716.

b. 4-(4-Bromo-2,5-dichloro-thiophene-3-sulfonylaminocarbonyl)-piperidine-1-carboxylic acid tert.-butyl ester 60 mg of DMAP, 130 mg of DIEA and 192 mg of EDC are added to a solution of 155 mg of 4-bromo-2,5-dichloro-thiophene-3-sulfonamide and 230 mg of 1-(tert.butyloxycarbonyl)-piperidine-4-carboxylic acid in 8 ml of DMF. The mixture obtained is stirred for ca. 16 h at ca. 30°, solvent is evaporated and the evaporation residue is treated with EtAc. The mixture obtained is washed with aqueous 1 N HCl, aqueous saturated $NaHCO_3$ and brine, and dried. Solvent from the organic phase obtained is evaporated and the evaporation residue is subjected to chromatography. 4-(4-Bromo-2,5-dichloro-thiophene-3-sulfonylaminocarbonyl)-piperidine-1-carboxylic acid tert.-butyl ester is obtained and lyophilized from 1,4-dioxane.

EXAMPLE B 4-(3,5-Bis-trifluoromethyl-benzenesulfonylaminocarbonyl)-cis-3-methyl-piperidine-1-carboxylic acid tert.-butyl ester (compound of Example 72) and 4-(3,5-Bis-trifluoromethyl-benzenesulfonylaminocarbonyl)trans-3-methyl-piperidine-1-carboxylic acid tert.-butyl ester (compound of Example 73)

18 ml of a sodium bis(trimethylsilyl)amide solution (2M) in THF are added to a suspension of 12.4 g of methoxymethyltriphenylphosphonium chloride in 25 ml of dry THF at 0°. To the mixture obtained, 5.87 g of 3-methyl-4-oxo-piperidine-1-carboxylic acid tert.butyl ester in 25 ml of THF are slowly added, the mixture obtained is stirred at 0°, diluted with EtAc and extracted with aqueous 1M HCl, saturated aqueous $NaHCO_3$ solution and brine. The organic layer obtained is dried and solvent is evaporated. The evaporation residue obtained is subjected to filtration over silica gel and solvent of the filtrate obtained is evaporated. 3.6 g of the filtration residue obtained are dissolved in 150 ml of $CH_3CN$, 1.68 g of cerium trichloride heptahydrate and 337 mg of sodium iodide are added and the resulting mixture is stirred at 40° overnight. From the mixture obtained solvent is evaporated and the evaporation residue obtained is treated with EtAc. The mixture obtained is extracted with aqueous 1M HCl, saturated aqueous $NaHCO_3$ solution and brine. The organic layer obtained is dried, solvent is evaporated and the evaporation residue obtained is subjected to filtration over silica gel and solvent of the filtrate obtained is evaporated. 494 mg of the evaporation residue obtained and 1.18 g of magnesium monoperoxyphthalic acid hexahydrate in 36 ml of $EtOH/H_2O$ (1:1) are stirred at RT and diluted with EtAc. The mixture obtained is extracted with aqueous 1M HCl. The organic layer obtained is dried, solvent is evaporated and the evaporation residue is subjected to filtration and solvent of the filtrate obtained is evaporated. To a solution of 60 mg of the evaporation residue obtained, 71 mg of 3,5-bis(trifluoromethyl)phenylsulfonamide, 94 mg of EDC and 30 mg of DMAP in 2 ml of DMF and 84 µl of DIEA are added and the mixture obtained is shaked at RT. From the mixture obtained solvent is removed and the concentrated residue obtained is subjected to preparative HPLC on an RP-18 column ($CH_3CN/H_2O$ (0.1% TFA).

4-(3,5-Bis-trifluoromethyl-benzenesulfonylaminocarbonyl)-cis-3-methyl-piperidine-1-carboxylic acid tert.-butyl ester and 4-(3,5-Bis-trifluoromethyl-benzenesulfonyl-aminocarbonyl)-trans-3-methyl-piperidine-1-carboxylic acid tert.-butyl ester are obtained.

EXAMPLE C

N-[1-(2-Nitro-phenyl)-piperidine-4-carbonyl]-3,5-bis-trifluoromethyl-benzenesulfonamide (compound of Example 81)

a. N-(Piperidine-4-carbonyl)-3,5-bis-trifluoromethyl-benzenesulfonamide in the form of a hydrochloride 2 g of 4-(3,5-bis-trifluoromethyl-benzenesulfonylaminocarbonyl)-piperidine-1-carboxylic acid tert.-butyl ester are dissolved in a mixture of 1 ml MeOH and 9 ml of $CH_2Cl_2$. The resulting mixture is treated at RT with 20 ml of 3 N HCl in $(C_2H_5)_2O$ for ca. 16 hours. Solvent is evaporated and N-(piperidine-4-carbonyl)-3,5-bis-trifluoromethyl-benzenesulfonamide in the form of a hydrochloride is obtained. m.p. 285-291°.

b. N-[1-(2-Nitro-phenyl)-piperidine-4-carbonyl]-3,5-bis-trifluoromethyl-benzenesulfonamide 0.13 g of DIEA and 0.07 g of 1-fluoro-2-nitrobenzene are added to a solution of 0.22 g N-(piperidine-4-carbonyl)-3,5-bis-trifluoromethyl-benzenesulfonamide in the form of a hydrochloride in 4 ml of DMSO. The mixture obtained is stirred for ca. 18 h at 80°, solvent is evaporated and the evaporation residue is subjected to flash chromatography on silica gel (eluent: EtAc). N-[1-(2-Nitro-phenyl)-piperidine-4-carbonyl]-3,5-bis-trifluoromethyl-benzenesulfonamide is obtained.

EXAMPLE D trans-[4-(4-Bromo-2,5-dichloro-thiophene-3-sulfonylaminocarbonyl)-cyclohexylmethyl]-carbamic acid tert-butyl ester (compound of Example 109)

a. 4-Bromo-2,5-dichloro-thiophene-3-sulfonamide 90 ml of an aqueous solution of $NH_3$ (32%) is added at RT to a solution of 8.88 g of 4-bromo-2,5-dichloro-thiophene-3-sulfonylchloride in 120 ml of EtAc. The mixture obtained is stirred for ca. 15 h and two phases obtained are separated. The organic layer is washed with 1 N HCl and $H_2O$, and dried. Solvent of the organic solution obtained is evaporated. 4-Bromo-2,5-dichloro-thiophene-3-sulfonamide in the form of a white powder is obtained. m.p. 113-117° C., $^{13}$C-NMR: δ=108.287; 125.342; 130.404; 135.716.

b. trans-[4-(4-Bromo-2.5-dichloro-thiophene-3-sulfonylaminocarbonyl)-cyclohexylmethyl]-carbamic acid tert.-butyl ester 60 mg of DMAP, 130 mg of DIEA and 192 mg of EDC are added to a solution of 155 mg of 4-bromo-2,5-dichloro-thiophene-3-sulfonamide and 257 mg of trans-1-(tert.butyloxycarbonyl-aminomethyl)cyclohexane-4-carboxylic acid in 8 ml of DMF and the mixture obtained is stirred for ca. 16 hours at ca. 30°. From the mixture obtained solvent is evaporated and the evaporation residue obtained is dissolved in EtAc. The solution obtained is washed with 1 N HCl, saturated $NaHCO_3$ solution and brine and dried. From the organic phase obtained solvent is evaporated and the evaporation residue obtained is subjected to chromatography. trans-[4-(4-Bromo-2,5-dichloro-thiophene-3-sulfonylaminocarbonyl)-cyclohexylmethyl]-carbamic acid tert.-butyl ester is obtained.

EXAMPLE E

4-Chloro-N-(4-pentyl-bicyclo[2.2.2]octane-1-carbonyl)benzenesulfonamide (compound of Example 186)

0.42 g of 4-chlorophenylsulfonamide, 60 mg of DMAP and 0.42 g of EDC are added to a solution of 0.5 g of 4-pentyl-bicyclo[2.2.2]octane-1-carboxylic acid in 8 ml of DMF, the mixture obtained is stirred for ca. 16 h at RT and solvent from the mixture obtained is evaporated. The evaporation residue obtained is dissolved in EtAc and washed with 1 N HCl, saturated $NaHCO_3$ solution and brine and the organic phase obtained is dried. Solvent of the organic phase obtained is evaporated and the evaporation residue obtained is subjected to chromatography. 4-Chloro-N-(4-pentyl- bicyclo[2.2.2]octane-1-carbonyl)-benzenesulfonamide is obtained in the form of a white powder;

EXAMPLE F 10-(3,5-bis-trifluoromethyl-benzenesulfonylaminocarbonyl)-8-aza-bicyclo[4.3.1]decane-8-carboxylic acid tert-butyl ester (compound of Example 217)

a. 10-Oxo-8-aza-bicyclo[4.3.1]decane-8-carboxylic acid tert-butyl ester 25 g of 8-methyl-8-aza-bicyclo[4.3.1]decane-10-one in the form of a hydrobromide are dissolved in $H_2O$ and a pH of ~11 is adjusted by addition of aqueous NaOH solution. The mixture obtained is extracted with $(C_2H_5)_2O$. The organic layer obtained is dried and solvent is evaporated. The evaporation residue obtained is dissolved in 50 ml of dichloroethane, 23.7 ml of 1-chloroethyl chloroformate are added at 0° and the mixture obtained is stirred at 80°, cooled to RT, and 50 ml of MeOH are added. The mixture obtained is stirred at 60°, solvent is evaporated and the evaporation residue obtained together with 18 g of $K_2CO_3$ and 28.4 g of di-tert.-butyldicarbonate is treated with 240 ml of THF/$H_2O$ (5:1) and stirred at RT. The mixture obtained is concentrated under reduced pressure and diluted with EtAc. The mixture obtained is extracted with $H_2O$, 1M HCl, aqueous, saturated $NaHCO_3$ solution and brine. The organic layer obtained is dried and solvent is evaporated. The evaporation residue is subjected to filtration over silica gel with EtAc/c-Hex (1:3). 10-Oxo-8-aza-bicyclo[4.3.1]decane-8-carboxylic acid tert-butyl ester is obtained. m.p.: 50-52°; $^{13}$C-NMR: 211.99, 154.82, 80.20, 48.70, 28.44, 26.40.

b. 10-Methoxymethylene-8-aza-bicyclo[4.3.1]decane-8-carboxylic acid tert-butyl ester To a suspension of 9.54 g of methoxymethyltriphenylphosphonium chloride in 25 ml of dry THF, 13.8 ml of a sodium bis(trimethylsilyl)amide solution (2M) in THF are added at 0° under stirring. To the mixture obtained 5.40 g of 10-oxo-8-aza-bicyclo[4.3.1]decane-8-carboxylic acid tert-butyl ester in 25 ml of THF are slowly added and stirring at 0° is continued. The mixture obtained—diluted with EtAc—is extracted with aqueous 1M HCl, aqueous saturated $NaHCO_3$ solution and brine. The organic layer obtained is dried and solvent is evaporated. The evaporation residue obtained is subjected to filtration over silica gel with EtAc/c-Hex (1:9). 10-Methoxymethylene-8-aza-bicyclo[4.3.1]decane-8-carboxylic acid tert-butyl ester is obtained. $^{13}$C-NMR: 155.54, 142.46, 118.38, 79.58, 59.82, 52.17, 50.89, 49.54, 36.93, 35.53, 34.91, 33.80, 33.50, 32.08, 28.94, 27.30, 27.18.

c. 10-Formyl-8-aza-bicyclo[4.3.1]decane-8-carboxylic acid tert-butyl ester 4.8 g of 10-methoxymethylene-8-aza-blcyclo[4.3.1]decane-8-carboxylic acid tert-butyl ester are dissolved in 180 ml of $CH_3CN$, 1.94 g of cerium trichloride heptahydrate and 390 mg of sodium iodide are added and the mixture obtained is stirred at 40° overnight. From the mixture obtained solvent is evaporated and the evaporation residue obtained is dissolved in EtAc. The mixture obtained is extracted with aqueous 1M HCl, aqueous, saturated $NaHCO_3$-solution and brine. The organic layer obtained is dried, solvent is evaporated and the evaporation residue obtained is subjected to filtration over silica gel with EtAc/c-Hex (1:4→1:2). 10-Formyl-8-aza-bicyclo[4.3.1]decane-8-carboxylic acid tert-butyl ester is obtained. m.p.: 55-60°; $^{13}$C-NMR: 204.53, 155.28, 78.00, 55.40, 32.44, 32.12, 30.06, 28.89, 27.29.

d. 8-Aza-bicyclo[4.3.1]decane-8.10-dicarboxylic acid 8-tert-butyl ester 2.86 g of 10-formyl-8-aza-bicyclo[4.3.1]decane-8-carboxylic acid tert-butyl ester and 5.8 g of magnesium monoperoxyphthalic acid hexahydrate in 170 ml of EtOH/$H_2O$ (1:1) are stirred at RT. The mixture obtained is diluted with EtAc. The mixture obtained is extracted with aqueous 1M HCl and brine. The organic layer obtained is dried, solvent is evaporated and the evaporation residue is crystallized from MeOH/$H_2O$. 8-aza-bicyclo[4.3.1]decane-8,10-dicarboxylic acid 8-tert-butyl ester is obtained. m.p.: 218-222°; $^{13}$C-NMR: 179.88, 155.31, 80.00, 52.43, 50.98, 47.63, 33.14, 32.31, 28.91, 27.06.

e. 10-(35-Bis-trifluoromethyl-benzenesulfonylaminocarbonyl)-8-aza-bicyclo[4.3.1]decane-8-carboxylic acid tert-butyl ester 6.1 ml of a 50% PPA solution in DMF, 633 mg of DMAP in 50 ml of dimethylamine and 1.8 ml of DIEA are added to a solution of 1.5 g of 8-aza-bicyclo[4.3.1]decane-8,10-dicarboxylic acid 8-tert-butyl ester, 2.3 g of 3,5-bis(trifluoromethyl)phenylsulfonamide, the mixture obtained is stirred at 40° and diluted with EtAc. The mixture obtained is extracted with aqueous 1M $NaHSO_4$-solution, saturated $NaHCO_3$-solution and brine. From the mixture obtained solvent is distilled off. The distillation residue obtained is purified by filtration over silica gel with EtAc/c-Hex/MeOH (5:5:1) and the purified residue is subjected to crystallization from $CH_3CN$:$H_2O$ (4:6). 10-(3,5-Bis-trifluoromethylbenzenesulfonylamino-carbonyl)-8-aza-bicyclo[4.3.1]decane-8-carboxylic acid tert-butyl ester in the form of a sodium salt is obtained which is dissolved in EtAc and 1 M aqueous HCl and $H_2O$, the phases obtained are separated, the organic layer obtained is dried and solvent is evaporated. 10-(3,5-bis-trifluoromethyl-benzene-sulfonylaminocarbonyl)-8-aza-bicyclo[4.3.1]decane-8-carboxylic acid tert-butyl ester is obtained.

EXAMPLE G

2-{4-[2-(3,5-Bis-trifluoromethyl-benzenesulfonylamino)-2-oxo-ethyl]-piperidin-1-yl}-4-trifluoromethyl-benzamide (compound of Example 241)

a. 3,5-Bis-(trifluoromethyl)benzene-sulfonamide

An aqueous solution of $NH_3$ (32%) is added at RT to a solution of 3,5-bis(trifluoromethyl)-benzene-sulfonylchloride in EtAc. The mixture obtained is stirred and two phases are obtained and are separated. The organic layer obtained is washed with 1 N HCl and $H_2O$, and dried. Solvent of the organic solution obtained is evaporated. 3,5-Bis-trifluoromethyl-benzene sulfonamide is obtained.

b. 2-{4-[2-(3.5-Bis-trifluoromethyl-benzenesulfonyamino)-2-oxo-ethyl]-piperidin-1-yl}-4-trifluoromethyl-benzamide 0.46 g of 2-fluoro-4-(trifluoromethyl)benzamide are added to a suspension of 1.8 g $K_2CO_3$ and 0.8 g of piperidin-4-yl acetic acid hydrochloride In 12 ml of DMSO, the mixture obtained is stirred for 4 h at 150°, solvent is evaporated, the evaporation residue obtained is suspended in MeOH and filtrated. The filtrate obtained is concentrated and subjected to chromatography on silica gel. [1-(2-Carbamoyl-5-trifluoromethyl-phenyl)-piperidin-4-yl]-acetic acid is obtained. 300 mg of EDC are added to a solution of 260 mg of [1-(2-carbamoyl-5-trifluoromethyl-phenyl)-piperidin-4-yl]-acetic acid, 230 mg of 3,5-bis-trifluoromethyl-benzenesulfonamide, 200 mg of DIEA and 90 mg of DMAP in 4 ml of DMF. The mixture obtained is stirred for 3 days at RT, solvent is evaporated in vacuo and the evaporation residue obtained is treated with EtAc. The mixture obtained is washed with 1 N HCl, saturated aqueous $NaHCO_3$ solution and brine, dried, concentrated in vacuo and subjected to chromatography on silica gel. 2-{4-[2-(3,5-Bis-trifluoromethyl-benzenesulfonylamino)-2-oxo-ethyl]-piperidin-1-yl}-4-trifluoromethyl-benzamide is obtained.

EXAMPLE H

3-[2-(4-Bromo-2,5-dichloro-thiophene-3-sulfonylamino)-2-oxo-ethyl]-9-aza-bicyclo[3.3.1]nonane-9-carboxylic acid tert-butyl ester (compound of Example 242)

a. 3-Oxo-9-aza-bicyclo[3.3.1]nonane-9-carboxylic acid tert-butyl ester 19.1 g of 9-methyl-9-aza-bicydo[3.3.1]nonane-3-one in the form of a hydrochloride are suspended in 150 ml of dichloroethane and 26 ml of DIEA are added slowly at 0°. The mixture obtained is stirred for 1 hour at 0°, to the mixture obtained 27 ml of 1-chloroethyl chloroformate are added and the mixture obtained is stirred at 80° for 8 hours and cooled to RT. To the mixture obtained 100 ml of MeOH are added, the mixture obtained is stirred at 600 for 5 hours and solvent is evaporated. The evaporation residue obtained, 18 g of $K_2CO_3$ and 28.4 g of di-tert.-butyldicarbonate are treated with 250 ml of THF/$H_2O$, the mixture obtained is stirred at RT for 3 hours, concentrated under reduced pressure and diluted with EtAc. The mixture obtained is washed with $H_2O$. 1M HCl, saturated $NaHCO_3$ solution and brine, the organic layer obtained is dried and solvent is evaporated. The evaporation residue obtained is subjected to filtration over silica gel. 3-Oxo-9-aza-bicyclo[3.3.1]nonane-9-carboxylic acid tert-butyl ester is obtained in the form of an oil and is crystallized. $^{13}$C-NMR: 209.94, 168.09, 154.33, 80.56, 48.90, 47.58, 45.81, 45.61, 30.95, 30.67, 28.81, 16.67.

b. 3-Ethoxycarbonylmethylene-9-aza-bicyclo[3.3.1] nonane-9-carboxylic acid tert-butyl ester 0.54 ml of (diethoxy-phosphoryl)-acetic acid ethyl ester are added dropwise to a suspension of 108 mg of NaH (55% in mineral oil) in 5 ml of THF at 0°. The mixture obtained is stirred and 650 mg of 3-oxo-9-aza-bicyclo[3.3.1]nonane-9-carboxylic acid tert-butyl ester in 5 ml of THF are slowly added. The mixture obtained is stirred at 60° C. for 3 days, diluted with c-HEX and washed with 1M aqueous $NaH_2PO_4$ and saturated aqueous $NaHCO_3$ solution. The organic layer obtained is dried, solvent is evaporated and the evaporation residue obtained is subjected to chromatography on silica gel. 3-Ethoxycarbonylmethylene-9-aza-bicyclo[3.3.1]nonane-9-carboxylic acid tert-butyl ester is obtained in the form of an oil. $^{13}$C-NMR: 171.79, 154.45, 154.27, 133.38, 132.77, 127.11, 126.30, 79.64, 79.54, 61.03, 61.00, 48.59, 47.20, 46.81, 45.22, 42.72, 33.61, 33.42, 32.59, 32.17, 30.73, 30.07, 28.87, 28.57, 28.13, 16.48, 14.59.

c. 3-Ethoxycarbonylmethyl-9-aza-bicyclo[3.3.1]nonane-9-carboxylic acid tert-butyl ester 390 mg of 3-ethoxycarbonylmethylene-9-aza-bicyclo[3.3.1]nonane-9-carboxylic acid tert-butyl ester are dissolved in 50 ml of EtOH and hydrogenated (50 bar, RT) in the presence of 100 mg of $PtO_2$ as a catalyst. From the mixture obtained the catalyst is filtrated off and 3-ethoxycarbonylmethyl-9-aza-bicyclo[3.3.1]nonane-9-carboxylic acid tert-butyl ester in the form of a mixture of the syn and anti isomers is obtained. $^{13}$C-NMR: 172.95, 172.88, 155.55, 154.44, 79.46, 79.42, 60.63, 47.40, 45.96, 45.88, 44.60, 43.77, 40.69, 37.01, 36.63, 32.24, 32.03, 31.40, 31.02, 29.61, 29.21, 29.17, 27.43, 20.60, 14.65, 14.07.

d. 3-Carboxymethyl-9-aza-bicyclo[3.3.1]nonane-9-carboxylic acid tert-butyl ester 10 ml of 1M aqueous NaOH are added to a solution of 3-ethoxycarbonylmethyl-9-aza-bicyclo[3.3.1]nonane-9-carboxylic acid tert-butyl ester in 20 ml of THF and the mixture obtained is stirred at RT. To the mixture obtained 10 ml of brine and 70 ml of EtAc are added, and the mixture obtained is washed with 1M aqueous HCl. The organic layer obtained is dried and solvent is evaporated. 3-Carboxymethyl-9-aza-bicyclo[3.3.1]nonane-9-carboxylic acid tert-butyl ester in the form of an oil is obtained. $^{13}$C-NMR: 178.47, 177.28, 155.61, 154.50, 79.70, 79.63, 47.39, 45.88, 43.39, 40.31, 36.92, 32.22, 31.98, 31.37, 30.99, 30.74, 30.64, 30.08, 29.59, 29.20, 21.15, 20.60, 14.05.

e. 3-[2-(4-Bromo-2,5-dichloro-thiophene-3-sulfonylamino)-2-oxo-ethyl]-9-aza-bicyclo[3.3.1]nonane-9-carboxylic acid tert-butyl ester 69 µl of DIEA are added to a solution of 57 mg of 3-carboxymethyl-9-aza-bicyclo[3.3.1]nonane-9-carboxylic acid tert-butyl ester, 93 mg of 2,4,5-trichloro-thiophene-3-sulfonic acid amide, 233 µl of PPA and 24 mg of DMAP in 2 ml of DMA, and the mixture obtained is stirred at RT for 48 hours. From the mixture obtained solvent is evaporated and the evaporation residue obtained is subjected to preparative HPLC on an RP-18 column followed by lyophilisation from dioxane. 3-[2-(4-Bromo-2,5-dichloro-thiophene-3-sulfonylamino)-2-oxo-ethyl]-9-aza-bicyclo[3.3.1]nonane-9-carboxylic acid tert-butyl ester in the form of a powder is obtained.

EXAMPLE J

9-[1-Fluoro-2-oxo-2-(2,4,5-trichloro-thiophene-3-sulfonylamino)ethylidene]-3-aza-bicyclo[3.3.1]nonane-3-carboxylic acid tert-butyl ester (compound of Example 288)

a. 9-Oxo-3-aza-bicyclo[3.3.1]decane-3-carboxylic acid tert-butyl ester 20 g of 3-methyl-3-aza-bicyclo[3.3.1]decane-10-one oxalate are dissolved in $H_2O$ and the pH is adjusted to ~11 by addition of 1M aqueous NaOH solution. The mixture obtained is extracted with $(C_2H_5)_2O$, the organic layer obtained is dried and solvent is evaporated. The evaporation residue obtained is dissolved in 100 ml of dichloroethane, 22.5 ml of 1-chloroethyl chloroformate are added at 0°, the mixture obtained is stirred at 80°, cooled to RT and 100 ml of MeOH are added. The mixture obtained is stirred at 60° and solvent is evaporated. The evaporation residue obtained, 14.8 g of $K_2CO_3$ and 23.4 g of di-tert.-butyldicarbonate are treated with 300 ml of $THF/H_2O$ and stirred at RT. The mixture obtained is concentrated under reduced pressure, diluted with EtAc and washed with $H_2O$, 1M HCl, saturated aqueous $NaHCO_3$ solution and brine. The organic layer obtained is dried, solvent is evaporated and the evaporation residue is subjected to filtration over silica gel with EtAc/c-HEX. 9-Oxo-3-aza-bicyclo[3.3.1]decane-3-carboxylic acid tert-butyl ester is obtained in crystalline form. $^{13}$C-NMR: 216.58, 154.49, 80.36, 51.00, 50.15, 47.11, 34.08, 28.45, 19.49.

b. 9-(Fluoro-Ethoxycarbonylmethylene-3-aza-bicyclo[3.3.1]nonane-3-carboxylic acid tert-butyl ester 1.14 ml of (diethoxy-phosphoryl)-fluoro-acetic acid ethyl ester are added dropwise to a suspension of 244 mg of NaH (55% in mineral oil) in THF at 0°, the mixture obtained is stirred, 918 mg of 9-oxo-3-aza-bicyclo[3.3.1]decane-3-carboxylic acid tert-butyl ester in 10 ml of THF are added slowly and the mixture obtained is stirred at RT overnight. The mixture obtained is diluted with c-HEX and the diluted mixture obtained is washed with 1M aqueous $NaH_2PO_4$ and saturated aqueous $NaHCO_3$ solution. The organic layer obtained is dried, solvent is removed by distillation and the distillation residue obtained is subjected to chromatography on silica gel. 9-(Fluoro-ethoxycarbonylmethylene-3-aza-bicyclo[3.3.1]-nonane-3-carboxylic acid tert-butyl ester is obtained in the form of an oil. $^{13}$C-NMR: 161.43, 161.15, 154.65, 139.95, 139.4, 137.97, 79.79, 61.15, 50.33, 49.98, 48.97, 48.53, 31.39, 31.04, 30.98, 28.54, 28.49, 19.70, 14.14.

c. 9-(Carboxy-fluoro-methylene)-3-aza-bicyclo[3.3.1]nonane-3-carboxylic acid tert-butyl ester 10 ml of 1M aqueous NaOH are added to a solution of 9-(fluoro-ethoxycarbonylmethylene-3-aza-bicyclo[3.3.1]nonane-3-carboxylic acid tert-butyl ester in 20 ml of THF, the mixture obtained is stirred at 40°, 10 ml of brine are added and the mixture obtained is diluted with EtAc. The diluted mixture obtained is washed with 1M aqueous HCl, the organic layer obtained is dried and solvent is evaporated. 9-(Carboxy-fluoro-methylene)-3-aza-bicyclo[3.3.1]nonane-3-carboxylic acid tert-butyl ester in the form of an oil is obtained. $^{13}$C-NMR: 165.25, 164.96, 154.81, 142.21, 139.37, 137.42, 80.23, 50.39, 50.03, 49.37, 49.05, 33.21, 33.10, 32.94, 32.81, 31.74, 31.73, 31.37, 31.31, 28.51, 19.64.

d. 9-[1-Fluoro-2-oxo-2-(2,4,5-trichloro-thiophene-3-sulfonylamino)-ethylidene]-3-aza-bicyclo[3.3.1]nonane-3-carboxylic acid tert-butyl ester 69 µl of DIEA are added to a solution of 60 mg of 9-(carboxy-fluoro-methylene)-3-aza-bicyclo[3.3.1]nonane-3-carboxylic acid tert-butyl ester, 71 mg of 2,4,5-trichloro-thiophene-3-sulfonyl amide, 233 µl of PPA and 24 mg of DMAP in 2 ml of DMA, and the mixture obtained is stirred at 40° overnight. The mixture obtained is diluted with 10 ml of EtAc/c-HEX, and washed with 1M $NaHSO_4$ solution. The organic layer obtained is dried and solvent is evaporated. The evaporation residue obtained is subjected to chromatography on silica gel and on Sephadex LH20 (MeOH) and relevant fractions obtained from chromatography are subjected to lyophilisation from dioxane. 9-[1-Fluoro-2-oxo-2-(2,4,5-trichloro-thiophene-3-sulfonylamino)-ethylidene]-3-aza-bicyclo[3.3.1]nonane-3-carboxylic acid tert.-butyl ester in the form of a powder is obtained.

EXAMPLE K

3-[2-(4-Bromo-2,5-dichloro-thiophene-3-sulfonylamino)-1-cyano-2-oxo-ethylidene]-8-aza-bicyclo[3.2.1]octane-8-carboxylic acid tert-butyl ester (compound of Example 289)

a. 3-(Cyano-methoxycarbonyl-methylene)-8-azabicyclo[3.2.1]octane-8-carboxylic acid tert-butyl ester A solution of 2 g of 3-oxo-8-aza-bicyclo[3.2.1]octane-8-carboxylic acid tert-butyl ester, 1.2 ml of cyano-acetic acid methyl ester, 130 µl of piperidine and 38 mg of β-alanine in 4 ml of DMF is stirred at 70° C. for 48 hours, the mixture obtained is diluted with EtAc, washed with H$_2$O and brine, the organic layer obtained is dried, solvent is removed in vacuo and the residue obtained is subjected to chromatography on silica gel. 3-(cyano-methoxycarbonyl-methylene)-8-aza-bicyclo[3.2.1]octane-8-carboxylic acid tert-butyl ester is obtained in the form of an oil. $^{13}$C-NMR: 174.13, 162.27, 153.68, 115.37, 107.45, 80.70, 53.92, 53.08, 28.81.

b. 3-(Carboxy-cyano-methylene)-8-aza-bicyclo[3.2.1]octane-8-carboxylic acid tert-butyl ester 3-(cyano-methoxycarbonyl-methylene)-8-aza-bicyclo[3.2.1]octane-8-carboxylic acid tert-butyl ester is saponified analogously to the method described in example J, c). 3-(Carboxy-cyano-methylene)-8-aza-bicyclo[3.2.1]octane-8-carboxylic acid tert-butyl ester in the form of a foam is obtained. $^{13}$C-NMR: 165.14, 153.83, 115.12, 107.51, 81.23, 28.82.

c. 3-[2-(4-Bromo-2.5-dichloro-thiophene-3-sulfonylamino)-1-cyano-2-oxo-ethylidene]-8-aza-bicyclo[3.2.1]octane-8-carboxylic acid tert-butyl ester 120 µl of DIEA are added to a solution of 102 mg of 3-(carboxy-cyano-methylene)-8-aza-bicyclo[3.2.1]octane-8-carboxylic acid tert-butyl ester, 162 mg of 4-bromo-2,5-dichloro-thiophene-3-sulfonamide, 583 µl of PPA in DMF (50%) and 43 mg of DMAP in 4 ml of DMA, and the mixture obtained is stirred at RT for 48 hours. From the mixture obtained solvent is removed in vacuo and the residue obtained is subjected to preparative HPLC on an RP-18 column. 3-[2-(4-Bromo-2,5-dichloro-thiophene-3-sulfonylamino)-1-cyano-2-oxo-ethylidene]-8-aza-bicyclo[3.2.1]octane-8-carboxylic acid tert-butyl ester in the form of a foam is obtained.

EXAMPLE L 3,3-Dimethyl-butyric acid 4-[2-(4-bromo-2,5-dichloro-thiophene-3-sulfonylamino)-1-fluoro-2-oxo-ethylidene]-adamantan-1-yl ester (compound of Example 290)

a. 3.3-Dimethyl-butyric acid 4-oxo-adamantan-1-yl ester

A solution of 1.03 g of 5-hydroxy-2-adamantanone, 1.83 g of DMAP and 1.9 ml of 3,3-dimethylbutanoyl chloride in 10 ml of CH$_2$Cl$_2$ is stirred at 40° C. for 48 hours, 6 ml of aqueous 1M KH$_2$PO$_4$ solution are added and the mixture obtained is stirred. The layers obtained are separated, from the organic layer obtained solvent is evaporated and the evaporation residue obtained is subjected to chromatography. 3,3-Dimethyl-butyric acid 4-oxo-adamantan-1-yl ester in the form of an oil is obtained. $^{13}$C-NMR: 215.61, 171.52, 49.10, 47.02, 41.38, 39.93, 38.17, 30.74, 29.79, 29.62.

b. 3,3-Dimethyl-butyric acid 4-(fluoro-ethoxycarbonyl-methylene)-adamantan-1-yl ester 1.48 ml of (diethoxy-phosphoryl)-fluoro-acetic acid ethyl ester are added dropwise to a suspension of 317 mg of NaH (55% in mineral oil) in 30 ml of THF at 0°. The mixture obtained is stirred, 1.37 g of 3,3-dimethyl-butyric acid 4-oxo-adamantan-1-yl ester in 10 ml of THF are added slowly and the mixture obtained is stirred at RT overnight. The mixture obtained is diluted with EtAc and the diluted mixture obtained is washed with 1M aqueous NaH$_2$PO$_4$ and saturated aqueous NaHCO$_3$ solution. The organic layer obtained is dried, solvent is evaporated and the evaporation residue obtained is subjected to chromatography on silica gel. 3,3-Dimethyl-butyric acid 4-(fluoro-ethoxycarbonyl-methylene)-adamantan-1-yl ester is obtained in the form of an oil. $^{13}$C-NMR: 171.54, 161.64, 140.78, 140.66, 139.92, 137.45, 78.28, 61.06, 49.23, 41.82, 41.80, 41.46, 40.27, 37.78, 37.54, 32.41, 32.39, 32.19, 30.72, 30.20, 29.63, 14.21.

c. 3.3-Dimethyl-butyric acid 4-(carboxy-fluoro-methylene)-adamantan-1-yl ester 3,3-dimethyl-butyric acid 4-(fluoro-ethoxycarbonyl-methylene)-adamantan-1-yl ester is saponified analogously to the method as described in example J c. 3,3-Dimethyl-butyric acid 4-(carboxy-fluoro-methylene)-adamantan-1-yl ester in the form of a foam is obtained. $^{13}$C-NMR: 172.09, 166.50, 166.13, 144.79, 144.67, 139.55, 137.13, 78.52, 49.62, 42.22, 42.20, 41.83, 40.55, 38.31, 37.96, 33.12, 33.10, 32.95, 32.87, 31.94, 31.15, 30.52, 30.10, 30.04.

d. 3,3-Dimethyl-butyric acid 4-[2-(4-bromo-2,5-dichloro-thiophene-3-sulfonylamino)-1-fluoro-2-oxo-ethylidene]-adamantan-1-yl ester Coupling of 3,3-dimethyl-butyric acid 4-(carboxy-fluoro-methylene)-adamantan-1-yl ester with 4-bromo-2,5-dichloro-thiophene-3-sulfonamide and isolation is performed analogously to the method as described in Example K c. 3,3-Dimethyl-butyric acid 4-[2-(4-bromo-2,5-dichloro-thiophene-3-sulfonylamino)-1-fluoro-2-oxo-ethylidene]-adamantan-1-yl ester is obtained.

EXAMPLE M

[4cis/trans-(3,5-Bis-(trifluoromethyl)-benzene-sulfonaminocarbonylmethyl)-cyclohexyl]-carbamic acid tert.-butyl ester (compound of Example 331)

a. 3,5-Bis-(trifluoromethyl)benzene-sulfonamide

An aqueous solution of NH$_3$ (32%) is added at room temperature to a solution of 3,5-bis-(trifluoromethyl)benzene-sulfonylchloride in EtAc. The mixture obtained is stirred and two phases obtained are separated, the organic layer obtained is washed with 1 N HCl and H$_2$O, and dried. Solvent of the organic solution obtained is evaporated. 3,5-Bis-trifluoromethyl-benzene sulfonamide is obtained.

b. [4-cis/trans-(3.5-Bis-(trifluoromethyl)-benzene-sulfonylaminocarbonylmethyl)-cyclohexyl]-carbamic acid tert.-butyl ester 60 mg of DMAP, 130 mg of DIEA and 192 mg of EDC are added to a solution of 293 mg of 3,5-bis-trifluoromethyl-benzene-sulfonamide and 257 mg of cis/trans-1-(tert.butyloxy-carbonylamino)cyclohexane-4-acetic acid in 10 ml of DMF, and the mixture obtained is stirred for 16 h at ca. 30°. Solvent from the mixture obtained is evaporated and the evaporation residue obtained is dissolved in EtAc. The solution obtained is washed with 1 N HCl, saturated NaHCO$_3$ solution and brine, and dried. From the organic phase obtained solvent is evaporated and the evaporation residue obtained is subjected to chromatography. [4-cis/trans-(3,5-bis-(trifluoromethyl)-benzenesulfonylaminocarbonylethyl)-cyclohexyl]-carbamic acid tert.-butyl ester in the form of an isomeric mixture is obtained.

EXAMPLE N

1-[2-(3,5-Bis-trifluoromethyl-benzenesulfonylamino)-2-oxo-(4-chloro-phenyl)-ethyl]-piperidine-4-carboxylic acid cyclohexylamide (compound of Example 371)

140 mg of triethylamine and 0.32 ml of 50% propylphosphonic acid anhydride (solution in DMF) are added to a solution of 150 mg of (4-chlorophenyl)-(4-cyclohexylcarbamoyl-piperidin1-yl)-acetic acid, 174 mg of 3,5-bis(trifluoromethyl)-benzenesulfonamide and 24 mg of DMAP in 6 ml of anhydrous DMF at 10°. The mixture obtained is stirred for ca. 60 hours at RT, solvent is evaporated off and the evaporation residue obtained is treated with EtAc and H$_2$O. Two phases obtained are separated and the organic layer obtained is washed, dried and solvent is evaporated. The evaporation residue obtained is subjected to chromatography on silica gel. 1-[2-(3,5-Bis-trifluoromethyl-benzenesulfonylamino)-2-oxo-(4-chloro-phenyl)-ethyl]-piperidine-4-carboxylic acid cyclohexylamide is obtained.

EXAMPLE O

1-[2-Benzenesulfonylamino-1-(3,5-bistrifluoromethyl-phenyl)-2-oxo-ethyl]-piperidine-4-carboxylic acid cyclohexylamide (compound of Example 365)

A solution of 500 mg of bromo-(4-chlorophenyl)-acetic acid methyl ester in 1.3 ml of CH$_3$CN is added to a solution of 288 mg piperidine-4-carboxylic acid cyclohexylamide and 0.239 ml DIEA in 4 ml of CH$_3$CN at RT, the mixture obtained is stirred for ca. 24 hours at RT, solvent is evaporated and the evaporation residue obtained is treated with EtAc and H$_2$O. The organic phase obtained is washed, dried and solvent is evaporated. 1-[2-Benzenesulfonylamino-1-(3,5-bistrifluoromethyl-phenyl)-2-oxo-ethyl]-piperidine-4-carboxylic acid cyclohexylamide is obtained.

EXAMPLE P (COMPOUND OF EXAMPLE 375)

4(1-Carboxy-cyclopentyl)-piperidine-1-carboxylic acid tert-butyl ester a. 1-Pyridin-4-yl-cyclopentanecarboxylic acid ethyl ester 25 ml of a n-buthyllithium solution in HEX (1.6M) is slowly added to a solution of 2.17 ml of pyridin-4-yl-acetic acid ethyl ester in 200 ml of THF, the mixture obtained is stirred at RT for 30 minutes, is cooled to −78° C. and treated with 2.8 ml of 1,4-dibromobutane in 20 ml of THF. The mixture obtained is allowed to warm up to RT overnight, is treated with EtAc, the organic layer obtained is washed with water, saturated NaHCO$_3$ solution and brine, dried and solvent is evaporated. The evaporation residue obtained is subjected to chromatography.

1-Pyridin-4-yl-cyclopentanecarboxylic acid ethyl ester is obtained. $^{13}$C-NMR: 175.05, 152.68, 150.15, 122.44, 61.63, 59.18, 36.19, 24.06, 14.33.

b. 1-Piperidin-4-yl-cyclopentanecarboxylic acid ethyl ester in the form of a hydrochloride 1.75 g of 1-pyridin-4-yl-cyclopentanecarboxylic acid ethyl ester are dissolved in a mixture of 100 ml of MeOH and aqueous HCl (32%) and the mixture obtained is hydrogenated in the presence of 175 mg of PtO$_2$ as a catalyst under pressure for 5 hours. From the mixture obtained the catalyst is removed by filtration and solvent is evaporated. 1-Piperidin-4-yl-cyclopentanecarboxylic acid ethyl ester in the form of a hydrochloride salt is obtained. $^{13}$C-NMR (CD$_3$OD): 176.73, 61.33, 57.71, 45.08, 45.00, 42.14, 33.80, 25.49, 25.43, 25.36, 14.58.

c. 4-(1-Ethoxycarbonyl-cyclopentyl)-piperidine-1-carboxylic acid tert-butyl ester 2.0 g of 1-piperidin-4-yl-cyclopentanecarboxylic acid ethyl ester in the form of a hydrochloride is converted into 4-(1-ethoxycarbonyl-cyclopentyl)-piperidine-1-carboxylic acid tert-butyl ester analogously to the procedure as described in Example F, c. 4-(1-Ethoxycarbonyl-cyclopentyl)-piperidine-1-carboxylic acid tert-butyl ester is obtained. $^{13}$C-NMR: 177.22, 155.16, 79.67, 60.75, 58.22, 44.77, 44.46, 33.73, 28.83, 28.67, 25.34, 14.66.

d. 4-(1-Carboxy-cyclopentyl)-piperidine-1-carboxylic acid tert-butyl ester

A solution of 1.2 g of 4-(1-ethoxycarbonyl-cyclopentyl)-piperidine-1-carboxylic acid tert-butyl ester in a mixture of 100 ml of EtOH and 50 ml of an 1M aqueous NaOH is stirred at 70° for 14 days, EtAc is added and two phases obtained are are separated. The aqueous layer obtained is acidified with hydrochloric acid (pH 2-3) and extracted with EtAc. The organic layer obtained is washed with brine, dried and solvent is evaporated. 4-(1-Carboxy-cyclopentyl)-piperidine-1-carboxylic acid tert-butyl ester is obtained.

EXAMPLE Q

4-[(3,5-bis-trifluoromethyl-benzoylsulfamoyl)-methyl]-piperidine-1-carboxylic acid tert-butyl ester (compound of Example 378)

a. 4-[(benzhydryl-sulfamoyl)-methyl]-4-hydroxy-piperidine-1-carboxylic acid tert.-butyl ester 28 ml of n-butyllithium (1.6 N solution in HEX) are added at −700 to a solution of 5.22 g of N-(diphenylmethyl)-methanesulfonamide in 120 ml of THF. The mixture is warmed to 0°, cooled to −30° and treated with 4 g of BOC-piperidin-4-one in 15 ml of THF. The mixture obtained is stirred at RT overnight, solvent is evaporated, the evaporation residue obtained is treated with EtAc, washed with 1 N HCl, saturated, aqueous NaHCO$_3$ solution and brine, the organic layer obtained is dried and solvent is evaporated. The evaporation residue obtained is subjected to chromatography on silica gel. 4-[(Benzhydryl-sulfamoyl)-methyl]-4-hydroxy-piperidine-1-carboxylic acid tert.-butyl ester in the form of a powder is obtained. m.p. 121-123°.

b. 4-Hydroxy-4-sulfamoylmethyl-piperidine-1-carboxylic acid tert.-butyl ester 5.19 g of 4-[(benzhydryl-sulfamoyl)-methyl]-4-hydroxy-piperidine-1-carboxylic acid tert.-butyl ester in 150 ml of MeOH are treated with 100 µl of triethylamine and the mixture obtained is hydrogenated overnight at RT with 10% Pd/C as a catalyst. From the mixture obtained the catalyst is filtrated off, solvent is evaporated and the evaporation residue is subjected to chromatography on silica gel. 4-Hydroxy-4-sulfamoylmethyl-piperidine-1-carboxylic acid tert.-butyl ester are obtained. m.p. 176-180°.

c. 4-[(3.5-bis-trifluoromethyl-benzoyisulfamoyl)-methyl]-4-hydroxy-piperidine-1-carboxylic acid tert-butyl ester 1510 mg of 3,5-bis-(trifluoromethyl)-benzoic acid, 477 mg of DMAP, 1010 mg of DIEA and 1500 mg of EDC are added to a solution of 1150 mg of 4-hydroxy-4-sulfamoylmethyl-piperidine-1-carboxylic acid tert-butyl ester. The mixture obtained is stirred for 16 hours, solvent is evaporated and the evaporation residue is treated with EtAc, washed with 1 N HCl, saturated, aqueous NaHCO$_3$ solution and brine, the organic layer obtained is dried and subjected to chromatography on silica gel. 4-[(3,5-bis-trifluoromethyl-benzoylsulfamoyl)-methyl]-4-hydroxy-piperidine-1-carboxylic acid tert-butyl ester are obtained. m.p. 154-159°.

d. 4-[(3.5-bis-trifluoromethyl-benzoylsulfamoyl)-methylene]-piperidine-1-carboxylic acid tert.-butyl ester 1510 mg of Martin Sulfurane dehydrating agent are added to 300 mg of 4-[(3,5-bis-trifluoromethyl-benzoylsulfamoyl)-methyl]-4-hydroxy-piperidine-1-carboxylic acid tert.-butyl ester in 5 ml of CH$_2$Cl$_2$. The mixture obtained is stirred in a microwave oven at 100° for 15 minutes, from the mixture obtained solvent is evaporated and the evaporation residue is subjected to chromatogry on silica gel.

4-[(3,5-bis-trifluoromethyl-benzoylsulfamoyl)-methylene]-piperidine-1-carboxylic acid tert.-butyl ester is obtained. m.p. 132-136°.

e. 4-[(3,5-bis-trifluoromethyl-benzoylsulfamoyl)-methyl]-piperidine-1-carboxylic acid tert-butyl ester A solution of 880 mg of 4-[(3,5-bis-trifluoromethyl-benzoylsulfamoyl)-methylene]-piperidine-1carboxylic acid tert.-butyl ester in 100 ml of MeOH is hydrogenated (10% Pd/C as a catalyst). From the mixture obtained the catalyst is filtrated off and solvent is evaporated.

4-[(3,5-Bis-trfluoromethyl-benzoylsulfamoyl)-methyl]-piperidine-1-carboxylic acid tert-butyl ester is obtained.

Analogously to methods as described in the PROCEDURES (Examples A to Q), but using appropriate starting materials, compounds of formula

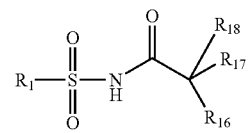

wherein R$_{18}$ is hydrogen and R$_1$ and R$_{16}$+R$_{17}$ are as defined in TABLE 1 (compounds of formula I, wherein m is 0, n is 0, and R$_1$ is a group of formula VII) are obtained, if not otherwise indicated in TABLE 1. If not otherwise indicated, in TABLE 1 $^{13}$C-NMR and $^1$H-NMR data are determined in CDCl$_3$.

TABLE 1

| EX | R$_1$ | R$_{16}$ + R$_{17}$ | m.p./$^1$H-NMR/$^{13}$C-NMR |
|---|---|---|---|
| 1 | Cl, Br, CH$_3$, Cl-thiophene | piperidine-N-C(O)O—C(CH$_3$)$_3$ | (DMSO-d$_6$): δ = 1.40(s, 9H); 1.41-1.82(m, 4H); 2.42(m, 1H), 2.78(t, 2H); 4.08(d, 2H) |
| 2 | (CH$_3$)$_3$C-phenyl | piperidine-N-C(O)O—C(CH$_3$)$_3$ | 1.20-1.38(m, 2H); 1.30(s, 9H); 1.64(d, 2H); 2.35(m, 1H); 2.60-2.80(m, 2H); 3.82(d, 2H); 7.58 + 7.78(2m, 4H) |
| 3 | 2,4,6-trimethylphenyl (CH$_3$, H$_3$C, CH$_3$) | piperidine-N-C(O)O—C(CH$_3$)$_3$ | 1.41(s, 9H); 1.43-1.80(m, 2H); 2.35(s, 3H); 2.34-2.42(m, 1H); 2.72(s, 6H); 2.60-2.80(m, 2H); 3.98-4.14(m, 2H); 6.98(s, 2H); 8.98(s, 1H) |

TABLE 1-continued

| EX | R₁ | R₁₆ + R₁₇ | m.p./¹H-NMR/¹³C-NMR |
|---|---|---|---|
| 4 | 2,4,6-tris(isopropyl)-3-methylphenyl (with CH(CH₃)₂ groups and CH₃) | 4-methylpiperidine-1-carboxylic acid tert-butyl ester | 1.24; 1.26; 1.28; 1.29; 1.32(5s, 18H); 1.43(s, 9H); 1.45-1.78 (m, 5H); 1.70(t, 2H); 2.91(sep, 1H); 4.03-4.25(m + sep, 4H); 7.24(s, 2H); 8.44(s, 1H) |
| 5 | 5-chloro-2,4-dimethylphenyl | 4-methylpiperidine-1-carboxylic acid tert-butyl ester | 1.40(s, 9H); 1.40-1.60(m, 2H); 1.72(m, 2H); 2.38(m, 1H); 2.40 (s, 3H); 2.56(s, 3H); 2.72(t, 2H); 4.04(d, 2H); 7.22(s, 1H); 7.98(s, 1H) |
| 6 | 2-(trifluoromethyl)phenyl | 4-methylpiperidine-1-carboxylic acid tert-butyl ester | 1.41(s, 9H); 1.41-1.82(m, 4H); 2.38(m, 1H), 2.75(t, 2H); 4.08 (d, 2H); 7.58-7.81(m, 2H); 7.85 (m, 1H); 8.50(m, 1H) |
| 7 | 4-(trifluoromethyl)phenyl | 4-methylpiperidine-1-carboxylic acid tert-butyl ester | 1.42(s, 9H); 1.45-1.90(m, 4H); 2.35(m, 1H); 2.78(t, 2H); 4.05 (d, 2H); 8.30(broad, 4H) |
| 8 | 3,5-bis(trifluoromethyl)phenyl | 4-methylpiperidine-1-carboxylic acid tert-butyl ester | 1.41(s, 9H); 1.45-1.68(m, 2H); 1.80(m, 2H); 2.30-2.40(m, 1H); 2.80(t, 2H); 4.10(d, 2H); 8.15 (s, 1H); 8.40(s, 1H); 8.54(s, 2H). 1.40(s, 9H); 1.40-1.60(m, 2H); 1.72(m, 2H); 2.30(m, 2H); 3.88(s, 3H); 4.04(d, 2H) |
| 9 | 5-chloro-2-methoxy-N-[2-(4-methylphenyl)ethyl]benzamide | 4-methylpiperidine-1-carboxylic acid tert-butyl ester | 1.12-1.36(m, 2H); 1.40(s, 9H); 1.63(d, 2H); 2.36-2.42(m, 1H); 2.60-2.80(m, 2H); 2.96(t, 2H); 3.55(q, 2H); 3.80(s, 3H); 3.84 (d, 2H); 7.18(d, 1H); 7.46-7.52 (m, 3H); 7.61(d, 1H); 7.81(d, 1H); 8.24(d, 1H) |
| 10 | 4-methoxyphenyl | 4-methylpiperidine-1-carboxylic acid tert-butyl ester | 1.40(s, 9H); 1.40-1.60(m, 2H); 1.72(m, 2H); 2.30(m, 2H); 3.88 (s, 3H); 4.04(d, 2H); 6.95(d, 2H); 7.90(2, 2H) |
| 11 | 2,4-dimethoxy-3-methylphenyl | 4-methylpiperidine-1-carboxylic acid tert-butyl ester | 1.40(s, 9H); 1.40-1.60(m, 2H); 1.72(m, 2H); 2.38(m, 1H); 2.72 (t, 2H); 3.85(s, 3H); 4.00(s, 3H); 4.04(d, 2H); 6.98(d, 1H); 7.18(dd, 1H); 7.60(d, 1H) |
| 12 | 4-(trifluoromethoxy)phenyl | 4-methylpiperidine-1-carboxylic acid tert-butyl ester | 1.41(s, 9H); 1.56-1.90(m, 4H); 2.30(m, 1H); 2.72(t, 2H); 4.04 (d, 2H); 7.34(d, 2H); 8.10(d, 2H); 8.22(s, 1H) |

TABLE 1-continued
| EX | R$_1$ | R$_{16}$ + R$_{17}$ | m.p./$^1$H-NMR/$^{13}$C-NMR |
|---|---|---|---|
| 13 | 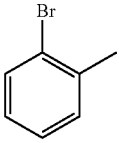 | 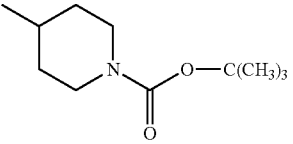 | 1.41(s, 9H); 1.50-1.90(m, 4H); 2.40(m, 1H); 2.78(t, 2H); 4.04 (d, 2H); 7.41-7.59(m, 2H); 7.74 (d, 1H); 8.28(d, 1H); 8.60(s, 1H) |
| 14 | 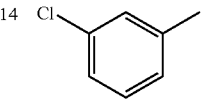 | 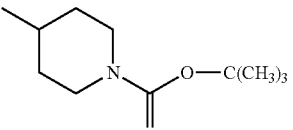 | 1.18-1.38(m, 2H); 1.40(s, 9H); 1.70(d, 2H); 2.38-2.45(m, 1H); 2.60-2.80(m, 2H); 3.82(d, 2H); 7.62 + 7.90(2m, 4H) |
| 15 | 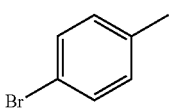 | 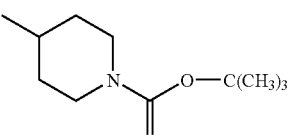 | 1.20-1.38(m, 2H); 1.40(s, 9H); 1.65(d, 2H); 2.40(m, 1H); 2.60-2.80(m, 2H); 3.84(d, 2H); 7.80 + 7.83(2m, 4H) |
| 16 | 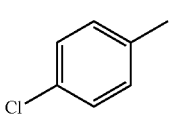 | 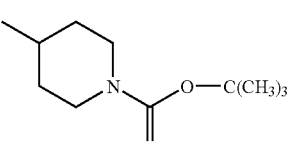 | 1.20-1.35(m, 2H); 1.40(s, 9H); 1.63(d, 2H); 2.41(m, 1H); 2.73 (t, 2H); 3.90(d, 2H); 7.70 + 7.90(2m, 4H) |
| 17 | 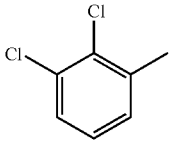 | 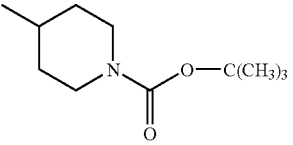 | 1.40(s, 9H); 1.40-1.60(m, 2H); 1.72(m, 2H); 2.38(m, 1H); 2.72 (t, 2H); 4.04(d, 2H); 7.38(t, 1H); 7.62(d, 1H); 8.13(d, 1H) |
| 18 | 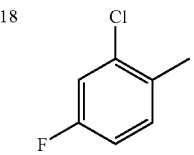 | 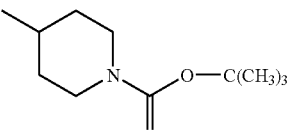 | 1.41(s, 9H); 1.38-1.90(m, 4H); 2.39(m, 1H); 2.78(t, 2H); 4.06 (d, 2H); 7.13-7.30(m, 2H); 8.26 (m, 1H) |
| 19 | 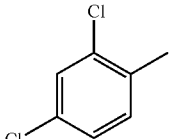 | 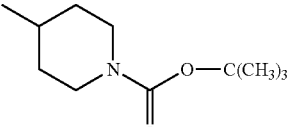 | 1.41(s, 9H); 1.40-1.93(m, 4H); 2.40(m, 1H); 2.80(t, 2H); 4.08 (d, 2H); 7.50(dd, 1H); 7.54(d, 1H); 8.18(d, 1H); 8.58(s, 1H) |
| 20 | 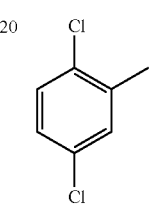 | 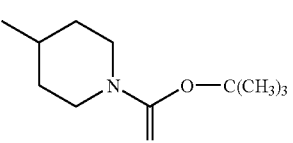 | 1.40(s, 9H); 1.40-1.60(m, 2H); 1.72(m, 2H); 2.38(m, 1H); 2.72 (t, 2H); 4.04(d, 2H); 7.38-7.50 (m, 2H); 8.18(m, 1H) |
| 21 | 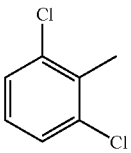 | 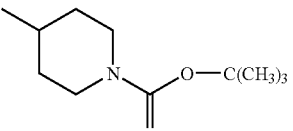 | 1.41(s, 9H); 1.41-1.85(m, 4H); 2.40(m, 1H); 2.78(t, 2H); 4.08 (d, 2H); 7.36-7.54(m, 3H) |

TABLE 1-continued
| EX | R$_1$ | R$_{16}$ + R$_{17}$ | m.p./$^1$H-NMR/$^{13}$C-NMR |
|---|---|---|---|
| 22 | 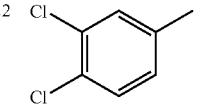 | 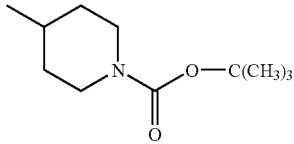 | 1.43(s, 9H); 1.44-1.95(m, 4H); 2.31(m, 1H); 3.76(t, 2H); 4.08 (d, 2H); 7.62(d, 1H); 7.90(d, 1H); 8.18(d, 1H) |
| 23 | 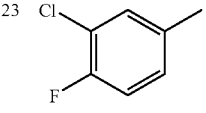 | 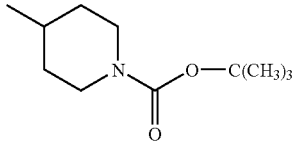 | 1.41(s, 9H); 1.41-1.88(m, 4H); 2.30(m, 1H); 2.74(t, 2H); 4.06 (d, 2H); 7.22(m, 1H); 7.98(m, 1H); 8.04(m, 1H); 8.30(s, 1H) |
| 24 | 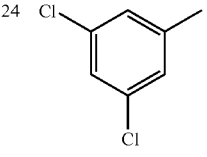 | 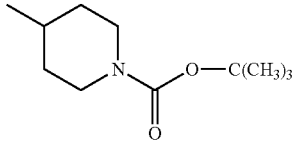 | 1.42(s, 9H); 1.35-1.90(m, 4H); 2.38(m, 1H); 2.76(t, 2H); 4.02(m, 2H); 7.56(s, 1H); 7.81(s, 2H) |
| 25 | 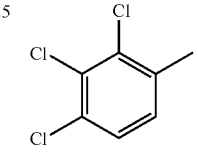 | 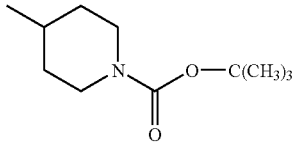 | 1.41(s, 9H); 1.40-1.91(m, 4H); 2.38(m, 1H); 2.78(t, 2H); 4.08 (d, 2H); 7.01(d, 1H); 8.14(d, 1H); 8.42(s, 1H) |
| 26 | 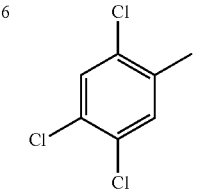 | 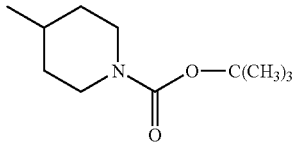 | 1.41(s, 9H); 1.38-1.88(m, 4H); 2.40(m, 1H); 2.78(t, 2H); 4.10 (d, 2H); 7.61(s, 1H); 8.32(s, 1H); 8.42(s, 1H) |
| 27 | 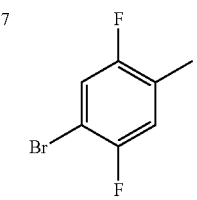 | 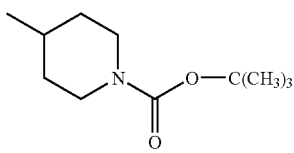 | 0.90(m, 1H); 1.20-1.90(m, 3H); 1.43(s, 9H); 2.40(m, 1H); 2.80 (t, 2H); 4.10(d, 2H); 7.43(dd, 1H); 7.83(dd, 1H); 8.48(s, 1H) |
| 28 | 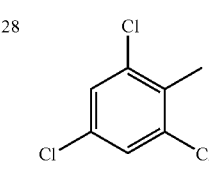 | 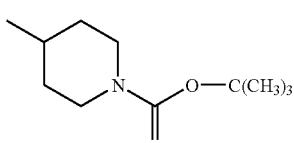 | 1.40(s, 9H); 1.40-1.90(m, 4H); 2.40(m, 1H); 2.78(t, 2H); 4.08 (d, 2H); 7.50(s, 2H); 8.84(s, 1H) |
| 29 | 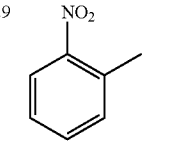 | 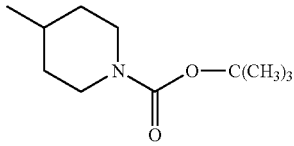 | 1.40(s, 9H); 1.40-1.60(m, 4H); 1.72(m, 2H); 2.40(m, 1H); 2.80 (t, 2H); 4.04(d, 2H); 7.78-7.82 (m, 3H); 8.42(m, 1H) |
| 30 | 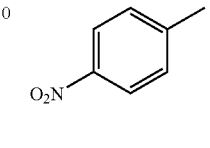 | 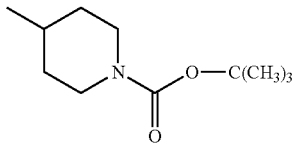 | 1.42(s, 9H); 1.42-1.86(m, 4H); 2.35(m, 1H); 2.74(t, 2H); 4.04 (d, 2H); 8.22 and 8.38(AB, 4H); 8.42(s, 1H) |

TABLE 1-continued
| EX | R$_1$ | R$_{16}$ + R$_{17}$ | m.p./$^1$H-NMR/$^{13}$C-NMR |
|---|---|---|---|
| 31 | 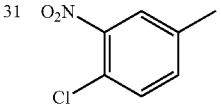 | 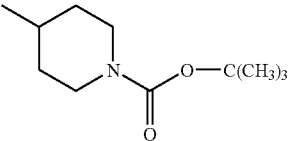 | 1.42(s, 9H); 1.40-1.96(m, 6H); 1.38(m, 1H); 1.79(t, 2H); 4.10 (d, 2H); 7.75(d, 1H); 8.23(dd, 1H); 8.50(d, 1H); 8.62(s, 1H) |
| 32 | 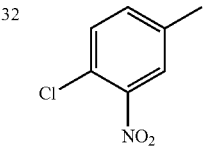 | 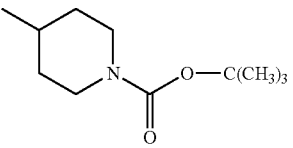 | 1.40(s, 9H); 1.42-1.90(m, 4H); 2.38(m, 1H); 2.78(t, 2H); 4.10 (d, 2H); 7.72(d, 1H); 8.21(dd, 1H); 8.41(s, 1H); 8.50(d, 1H) |
| 33 | 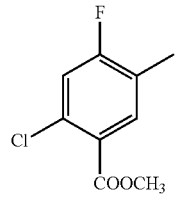 | 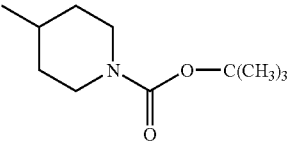 | 8.22(d, J=7.6Hz, 1H), 7.61(d, J=13.9Hz, 1H), 3.87(s, 3H), 3.73-3.82(m, 2H), 2.65-2.77(br.s, 1H), 2.07-2.16(br.s, 1H), 1.56-1.63(m, 2H), 1.36(s, 9H), 1.17-1.29(m, 2H) |
| 34 | 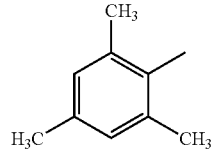 | 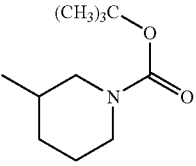 | 1.44(s, 9H); 1.65-1.99(m, 4H); 2.30(s, 3H); 2.40(m, 1H); 2.70 (s, 6H); 3.02-3.30(2m, 2H); 3.54-3.82(2m, 2H); 7.24(s, 2H) |
| 35 | 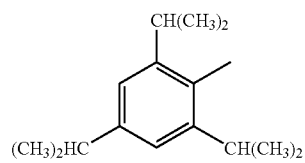 | 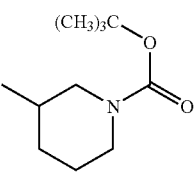 | 1.18-1.35(m, 18H); 1.48(s, 9H); 1.44-1.94(m, 4H); 2.40(m, 1H); 2.90(sep, 1H); 3.08-3.19(2m, 2H); 3.51-3.63(2m, 2H); 4.20 (sep, 2H); 7.07(s, 1H); 7.18(s, 2H) |
| 36 | 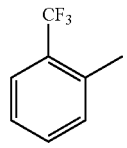 | 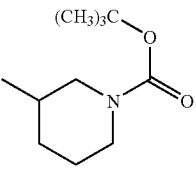 | 1.43 and 1.48(2s, 9H); 7.78(m, 2H); 7.80(m, 1H); 8.50(m, 1H) (mixture of rotamers) |
| 37 | 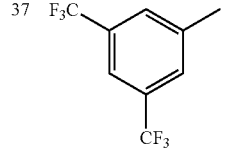 | 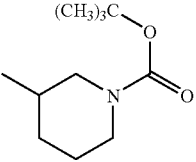 | 1.35-1.60(m, 11H), 1.70-2.20 (m, 2H); 2.50(m, 1H); 3.20-3.40 (m, 4H); 8.10(s, 1H); 8.55(s, 2H) |
| 38 | 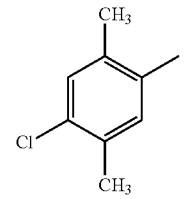 | 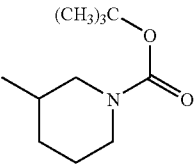 | 1.40-1.55(m, 11H); 1.80(m, 2H); 2.40(s, 3H); 2.42(m, 1H); 2.60(s, 3H); 3.10-3.80(m, 4H); 7.22(s, 1H); 8.00(s, 1H) |

TABLE 1-continued
| EX | R$_1$ | R$_{16}$ + R$_{17}$ | m.p./$^1$H-NMR/$^{13}$C-NMR |
|---|---|---|---|
| 39 | 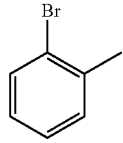 | 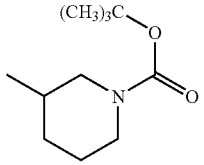 | 1.42 and 1.50(2s, 9H), 7.40-7.50(m, 2H); 7.63(dd, 1H); 8.28(dd, 1H) (mixture of rotamers) |
| 40 | 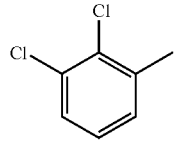 | 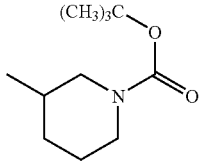 | 1.50(m, 11H); 2.50(m, 1H); 3.20-3.60(m, 3H); 3.70(m, 1H); 7.40(t, 1H); 7.50(d, 1H); 8.20(d, 1H) |
| 41 | 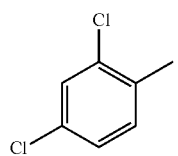 | 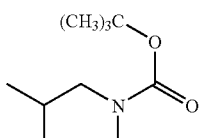 | 1.50(s, 9H); 1.78-2.00(m, 4H); 2.46(m, 1H); 3.18-3.58(m, 3H); 3.62-3.78(m, 1H); 7.43(dd, 1H); 7.54(d, 1H); 8.19(d, 1H) |
| 42 | 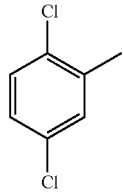 | 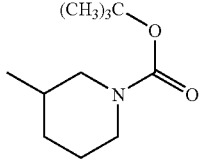 | 1.43(s, 9H); 1.50(m, 2H); 1.90(m, 2H); 2.50(m, 1H); 3.20-3.80(m, 4H); 7.40-7.58(m, 2H); 8.22(d, 1H) |
| 43 | 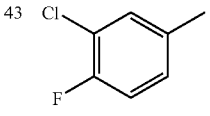 | 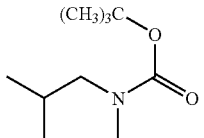 | 1.48(s, 9H); 1.70-2.10(m, 4H); 2.42(m, 1H); 3.40(m, 2H); 3.58(m, 2H); 7.20-7.29(m, 1H); 7.98(ddd, 1H); 8.10(dd, 1H) |
| 44 | 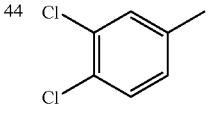 | 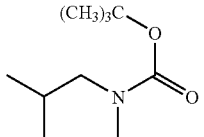 | 1.52(s, 9H); 1.60-2.15(m, 4H); 2.51(m, 1H); 3.30-3.72(m, 4H); 7.60(d, 1H); 7.86(dd, 1H); 8.10(d, 1H) |
| 45 | 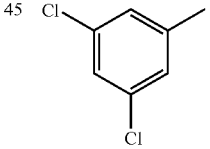 | 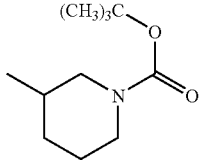 | 1.51(s, 9H); 1.62-2.16(m, 4H); 2.50(m, 1H); 3.35-3.66(m, 4H); 7.58(t, 1H); 7.94(d, 2H) |
| 46 | 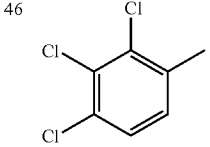 | 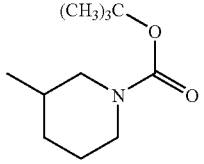 | 1.50(s, 9H); 1.79-1.99(m, 4H); 2.51(m, 1H); 3.27-3.72(m, 4H); 7.58(d, 1H); 8.10(d, 1H) |

TABLE 1-continued
| EX | R₁ | R₁₆ + R₁₇ | m.p./¹H-NMR/¹³C-NMR |
|---|---|---|---|
| 47 | 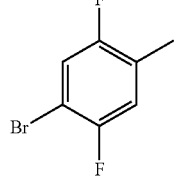 | 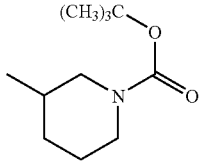 | 1.50(s, 9H); 1.75-2.02(m, 4H); 2.53(m, 1H); 3.22-3.80(m, 4H); 7.48(dd, 1H); 7.82(dd, 1H) |
| 48 | 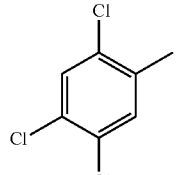 | 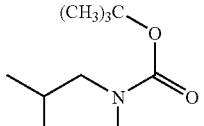 | 1.50(s, 9H); 1.70-2.02(m, 4H); 2.50(m, 1H); 3.22-3.38(m, 1H); 3.40-3.58(m, 2H); 3.68(m, 1H); 7.60(s, 1H); 8.34(s, 1H) |
| 49 | 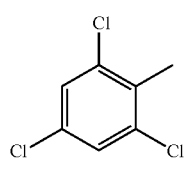 | 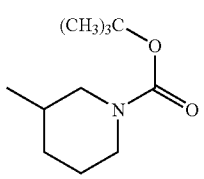 | 1.43(s, 9H); 1.40-1.98(m, 4H); 2.50(m, 1H); 3.23-3.40(2m, 2H); 3.54 and 3.74(2m, 2H); 7.52(s, 2H) |
| 50 | 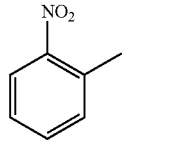 | 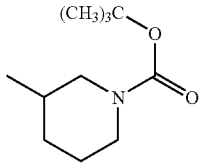 | 1.40-2.00(m, 13H), 2.50(m, 1H); 2.98-3.20(m, 2H); 3.70(m, 2H); 3.98(d, 2H); 7.80(m, 3H); 8.40(m, 1H) |
| 51 | 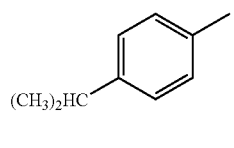 | 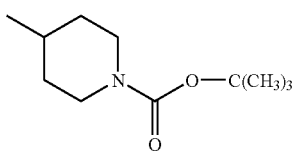 | 1.24(d, 6H); 1.42(s, 9H); 1.44-1.90 (m, 4H); 2.35(m, 1H); 2.78(t, 2H); 3.00(sept, 1H); 4.05(d, 1H); 7.38 (d, 2H); 7.90(d, 2H); 8.28(s, 1H) |
| 52 | 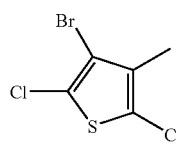 | 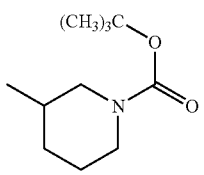 | 1.50(s, 9H); 1.80-2.04(m, 4H); 2.52(m, 1H); 3.21-3.78(m, 4H) |
| 53 | 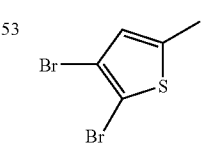 | 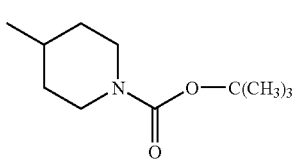 | 1.45(s, 9H), 1.60(dq, 2H), 1.78 (broad d, 2H), 2.32(tt, 1H), 4.06(broad d, 2H), 7.63(s, 1H) |
| 54 | 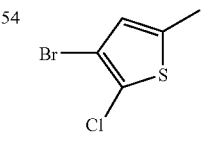 | 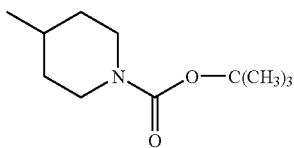 | 1.45(s, 9H), 1.59(dq, 2H), 1.76 (dq, 2H), 2.34(tt, 1H), 2.77 (broad t, 2H), 4.05(broad d, 2H), 7.60(s, 1H) |
| 55 | 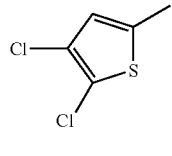 | 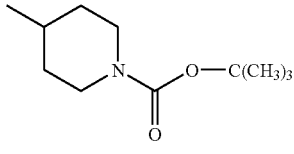 | 1.45(s, 9H), 1.59(dq, 2H), 1.77 (dq, 2H), 2.38-2.43(m, 3H), 2.76(broad t, 2H), 4.06(d, 2H), 7.63(s, 1H) |

TABLE 1-continued
| EX | R₁ | R₁₆ + R₁₇ | m.p./¹H-NMR/¹³C-NMR |
|---|---|---|---|
| 56 | 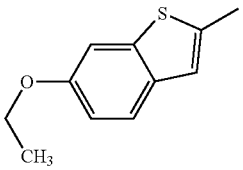 | 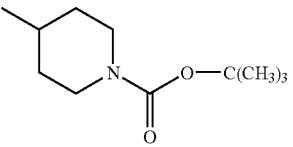 | 1.20-1.38(m, 2H), 1.40-1.42(m, 12H); 1.75(d, 2H); 2.40-2.55 (m, 1H); 2.62-2.82(m, 2H); 3.84 (d, 2H); 4.18(q, 2H); 7.23(dd, 1H); 7.81(d, 1H); 8.08(d, 1H) |
| 57 | 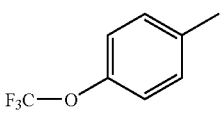 | 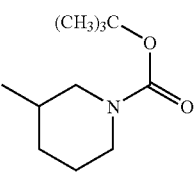 | 1.43(s, 9H); 1.43-2.10(m, 4H); 2.42(m, 1H); 3.26-3.59(m, 4H); 7.30(d, 2H); 8.08(d, 2H) |
| 58 | 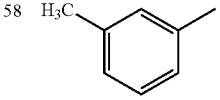 | 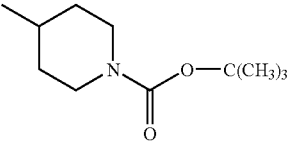 | 1.44(s, 9H); 1.52-1.61(m, 2H), 1.76(m, 2H); 2.31(m, 1H); 2.46 (s, 3H); 2.73(m, 2H); 4.05 (broad, 2H); 7.41-7.49(m, 2H); 7.82-7.88(m, 2H); 8.30(bs, 1H) |
| 59 | 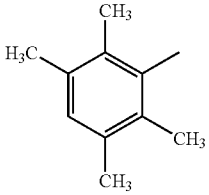 | 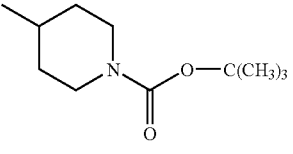 | (DMSO-d₆): 1.32(m, 2H); 1.43 (s, 9H); 1.76(m, 2H); 2.32(s, 6H); 2.52(m, 1H); 2.70-2.82 (broad, 2H); 3.40(s, 6H); 3.95 (d, 2H); 7.35(s, 1H) |
| 60 | 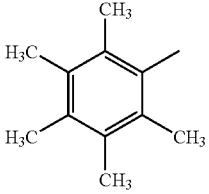 | 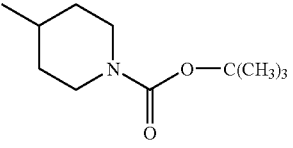 | (DMSO-d₆): 1.22(m, 2H); 1.38 (s, 9H); 1.66 d, 2H); 2.18(s, 6H); 2.22(s, 3H); 2.42(m, 1H); 2.54(s, 6H); 2.59-2.76(m, 2H); 3.87(d, 2H); 12.08(bs, 1H) |
| 61 | 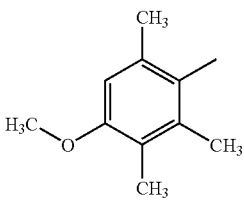 | 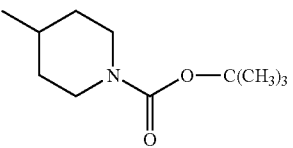 | (DMSO-d₆): 1.02(m, 2H); 1.16 (s, 9H); 1.44(m, 2H); 1.87(s, 3H); 2.12-2.25(m, 1H); 2.43(s, 3H); 2.48(broad, 2H); 3.61(s, 3H); 3.65(d, 2H); 6.60(s, 1H); 11.83(bs, 1H) |
| 62 | 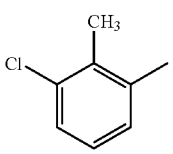 | 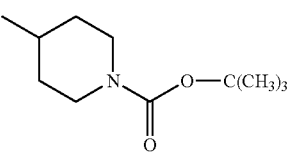 | 1.44(s, 9H); 1.53(m, 2H); 1.74(m, 2H); 2.35(m, 1H); 2.66(s, 3H); 2.75 (m, 2H); 4.03(d, 2H); 7.32(dt, 1H); 7.62(dd, 1H); 8.11(dd, 1H) |
| 63 | 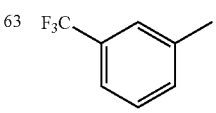 | 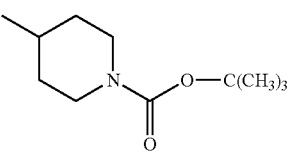 | 1.43(s, 9H); 1.53(m, 2H); 1.72 (m, 2H); 2.31(m, 1H); 2.73(m, 2H); 4.01(m, 2H); 7.70(t, 1H); 7.99(d, 1H); 8.26-8.30(m, 2H) |

TABLE 1-continued

| EX | R$_1$ | R$_{16}$ + R$_{17}$ | m.p./$^1$H-NMR/$^{13}$C-NMR |
|---|---|---|---|
| 64 | F$_3$C-phenyl with NC, 0lp;1p | 4-methylpiperidine N-C(O)O-C(CH$_3$)$_3$ | DMSO-d$_6$: 1.10(m, 2H); 1.23(s, 9H); 1.48(m, 2H); 1.97(m, 1H); 2.50-2.64(broad, 2H); 3.60(d, 2H); 8.02(dd, 1H); 8.05(d, 1H); 8.10(d, 1H) |
| 65 | F$_3$C-phenyl-Cl | 4-methylpiperidine N-C(O)O-C(CH$_3$)$_3$ | CDCl$_3$ + 5% CD$_3$OD: 1.44(s, 9H); 1.53(m, 2H); 1.78(d, 2H); 2.41(m, 1H); 2.78(m, 2H), 4.03 (m, 2H); 7.67(d, 1H); 7.81(dd, 1H); 8.51(d, 1H) |
| 66 | biphenyl | 4-methylpiperidine N-C(O)O-C(CH$_3$)$_3$ | (DMSO-d$_6$): 1.03(m, 2H); 1.45 (m, 2H); 2.18(m, 1H); 2.41-2.52 (m, 2H); 3.63(d, 2H); 7.30-7.35 (m, 1H); 7.40(t, 2H); 7.53(d, 2H); 7.67 and 7.72(AB, 4H) |
| 67 | 2,4-difluorophenyl | 4-methylpiperidine N-C(O)O-C(CH$_3$)$_3$ | 1.44(s, 9H); 1.57(m, 2H); 1.79 (m, 2H); 2.37(m, 1H); 2.77(m, 2H); 4.07(broad, 2H); 6.97(m, 1H); 7.08(m, 1H); 8.12(m, 1H), 8.45-8.85(broad, 1H) |
| 68 | 2-naphthyl | 4-methylpiperidine N-C(O)O-C(CH$_3$)$_3$ | CDCl$_3$ + 5% CD$_3$OD: 1.42(s, 9H); 1.50(m, 2H); 1.71(m, 2H); 2.34(m, 1H); 2.75(m, 2H); 7.60-7.70(m, 2H); 7.90-8.05(m, 4H); 8.63(s, 1H) |
| 69 | 1-naphthyl | 4-methylpiperidine N-C(O)O-C(CH$_3$)$_3$ | 1.34-144(m, 9 + 2H); 1.61(m, 2H); 2.29(m, 1H); 2.67(t, 2H); 3.91(dt, 2H); 7.57-7.63(m, 2H); 7.67(m, 1H); 7.96(dd, 1H); 8.12 (d, 1H); 8.48(dd, 1H); 8.58(dd, 1H) |
| 70 | 5-(dimethylamino)naphthyl | 4-methylpiperidine N-C(O)O-C(CH$_3$)$_3$ | CDCl$_3$ + 5% CD$_3$OD: 1.39(s, 9H); 1.42(m, 2H); 1.62(m, 2H); 2.29(m, 1H); 2.67(m, 2H); 2.90 (s, 6H); 3.93(m, 2H); 7.16(d, 1H); 7.52-7.61(m, 2H); 8.19(d, 1H); 8.48(dd, 1H); 8.59(d, 1H) |
| 71 | 2,2,5,7,8-pentamethylchroman | 4-methylpiperidine N-C(O)O-C(CH$_3$)$_3$ | (DMSO-d$_6$): 0.99(m, 2H); 1.04 (s, 6H); 1.13(s, 9H); 1.43(m, 2H); 1.56(t, 2H); 1.83(s, 3H); 2.15-2.23(m, 1H); 2.24-2.27 (m, 5H); 3.39(t, 2H); 2.42-2.48 (broad, 2H); 3.65(d, 2H) |

TABLE 1-continued
| EX | R₁ | R₁₆ + R₁₇ | m.p./¹H-NMR/¹³C-NMR |
|---|---|---|---|
| 72 | 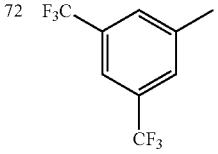 | 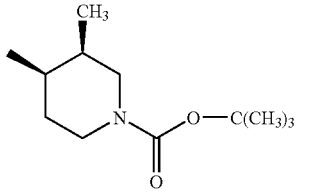 | 141.53, 133.45, 133.10, 129.33, 128.00, 80.35, 32.06, 28.74(cis) |
| 73 | 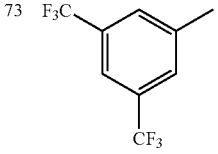 | 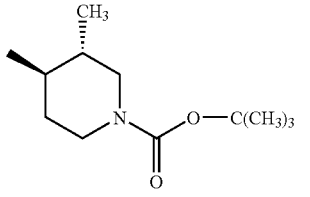 | 154.89, 141.61, 133.44, 133.10, 129.27, 127.92, 124.04, 121.33, 80.71, 67.48, 51.98, 33.31, 28.77, 16.90(trans) |
| 74 | 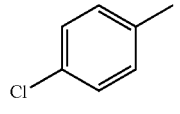 | 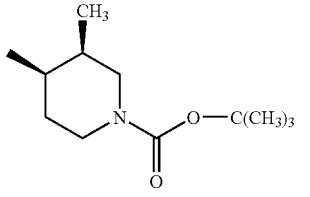 | 171.63, 155.41, 141.28, 137.19, 130.31, 128.72, 80.20, 67.48, 46.34, 32.05, 28.76, 13.01(cis) |
| 75 | 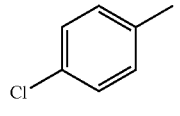 | 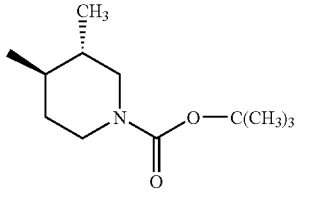 | 172.36, 154.83, 141.31, 137.18, 130.26, 129.75, 80.42, 51.87, 33.38, 28.76, 17.04(trans) |
| 76 | 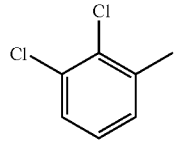 | 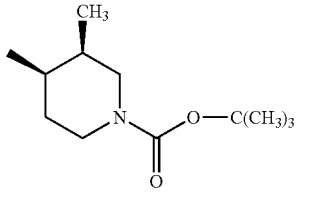 | 171.78, 155.40, 138.26, 136.08, 135.90, 132.07, 130.47, 128.10, 80.16, 67.48, 46.49, 31.95, 28.76, 12.93(cis) |
| 77 | 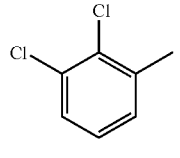 | 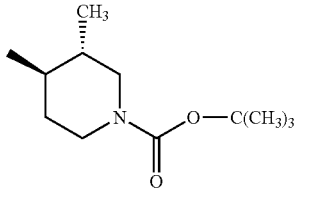 | 172.34, 154.77, 138.28, 136.11, 135.95, 132.01, 128.09, 80.39, 67.48, 51.98, 33.17, 28.77, 17.08(trans) |
| 78 | 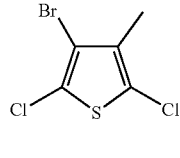 | 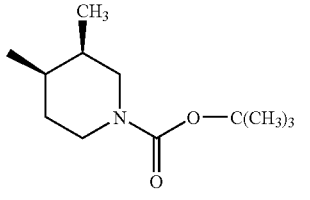 | 172.08, 155.42, 137.67, 131.09, 126.31, 108.53, 80.22, 67.48, 31.89, 28.78, 13.07(cis) |

TABLE 1-continued
| EX | R$_1$ | R$_{16}$ + R$_{17}$ | m.p./$^1$H-NMR/$^{13}$C-NMR |
|---|---|---|---|
| 79 | 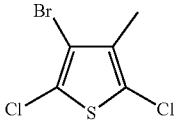 | 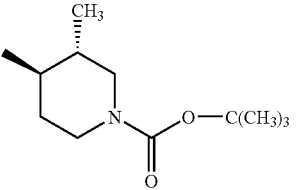 | 172.85, 154.79, 108.49, 80.43, 67.48, 51.87, 33.16, 28.79, 17.21(trans) |
| 80 | 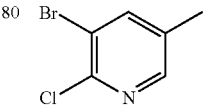 | 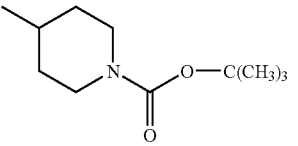 | 1.45(s, 9H), 1.55(dq, 2H), 1.75 (broad d, 2H), 2.32(tt, 1H), 2.75 (bt, 2H), 4.05(broad d, 2H), 8.58(d, 1H), 8.88(d, 1H) |
| 81 | 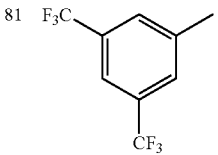 | 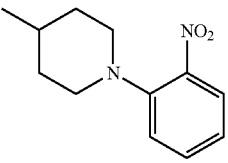 | δ = 1.80-1.95(m, 4H); 2.32-2.40(m, 1H); 2.73-2.83(m, 2H); 3.22(bd, 2H); 6.98(t, 1H); 7.08 (d, 1H); 7.42(dt, 1H); 7.71(dd, 1H); 7.94(s, 1H); 8.48(s, 2H) |
| 82 | 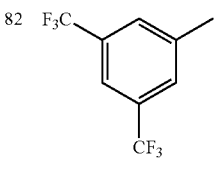 | 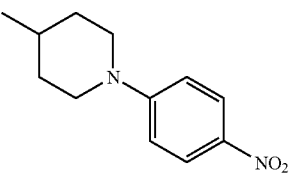 | 1.40-1-52(m, 2H); 1.68-1.76(m, 2H); 2.56(m, 1H); 3.03(dt, 2H); 3.98(dt, 2H); 6.98(d, 2H); 8.00 (d, 2H); 8.17(s, 1H); 8.25(s, 2H) |
| 83 | 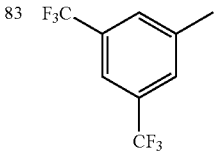 | 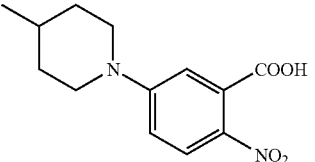 | 224-227° |
| 84 | 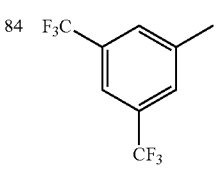 | 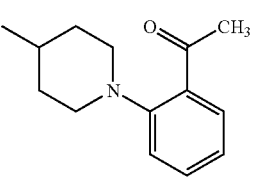 | (DMSO-d$_6$): 1.57(dq, 2H), 1.79 (broad d, 2H), 2.31(tt, 1H), 2.51(s, 3H), 2.66(dt, 2H), 3.07 (dt, 2H), 7.02(t, 1H), 7.10(d, 1H), 7.29(dd, 1H), 7.40(dt, 1H), 8.39(s, 2H), 8.49(s, 1H) |
| 85 | 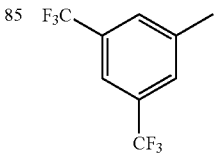 | 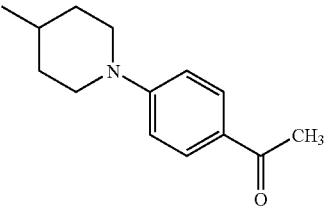 | (DMSO-d$_6$): 1.43(dq, 2H), 1.70 (dd, 2H), 2.20(m, 1H), 2.40(s, 3H), 2.84(t, 2H), 3.79(m, 2H), 4.05(broad, 1H, NH), 6.90(d, 2H), 7.73(d, 2H), 8.20(s, 1H), 8.25(s, 2H) |
| 86 | 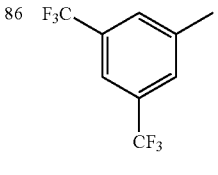 | 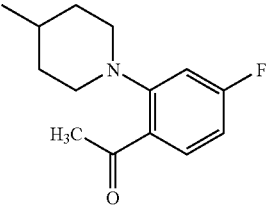 | 189-192° |

TABLE 1-continued
| EX | R$_1$ | R$_{16}$ + R$_{17}$ | m.p./$^1$H-NMR/$^{13}$C-NMR |
|---|---|---|---|
| 87 | 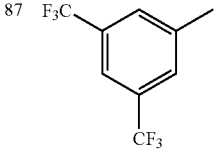 | 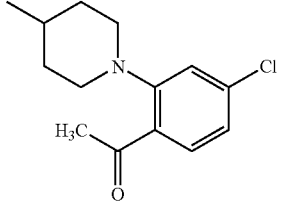 | 81-83° |
| 88 | 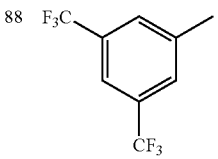 | 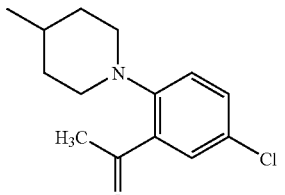 | 84-87° |
| 89 | 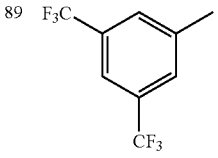 | 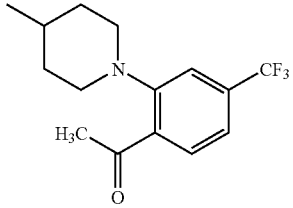 | 158-161° |
| 90 | 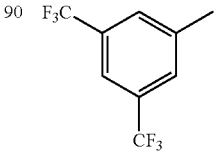 | 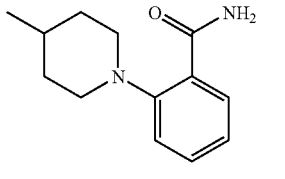 | 95-97° |
| 91 | 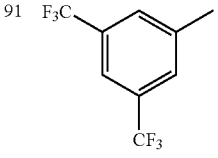 | 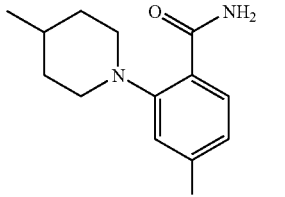 | 1.73-1.86(m, 2H); 1.94-2.08 (m, 2H); 2.30-2.40(m, 1H); 2.65-2.78(m, 2H); 3.15-3.22 (m, 2H); 6.85(d, 1H); 7.31(s, 1H); 7.36(d, 1H); 7.90(s, 1H); 8.12(d, 1H); 8.43(s, 2H); 9.08(d, 1H) |
| 92 | 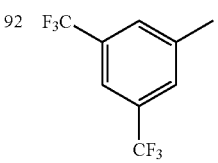 | 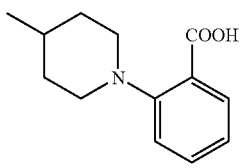 | (DMSO-d$_6$): 1.53-1.66(m, 2H); 1.89-1.98(m, 2H); 2.50-2.62 (m, 1H); 2.90-3.14(m, 4H); 7.35-7.40(m, 2H); 7.62(m, 1H); 7.96(d, 1H); 8.43(s, 2H); 8.58(s; 1H) |
| 93 | 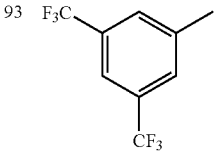 | 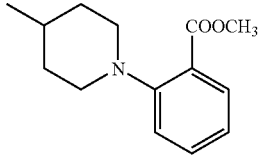 | (DMSO-d$_6$): 1.55(dq, 2H); 1.72 (dd, 2H); 2.04-2.13(m, 1H); 2.65(dd, 2H); 3.15(dt, 2H); 3.78 (s, 3H); 6.95(t, 1H); 7.05(d, 1H); 7.40(m, 1H); 7.54 (dd, 1H); 8.26(s, 1H); 8.33(s, 1H) |
| 94 | 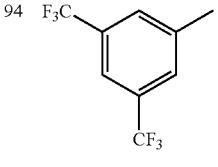 | 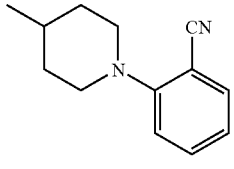 | (DMSO-d$_6$): 1.40(dq, 2H); 1.57(dd, 2H); 1.85-1.95(m, 1H); 2.55(dt, 2H); 3.12-3.22 (m, 2H); 6.81(t, 1H); 6.90(d, 1H); 7.32(m, 1H); 7.43(d, 1H); 8.02(s, 1H); 8.09(s, 2H) |

TABLE 1-continued
| EX | R₁ | R₁₆ + R₁₇ | m.p./¹H-NMR/¹³C-NMR |
|---|---|---|---|
| 95 | 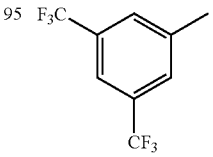 | 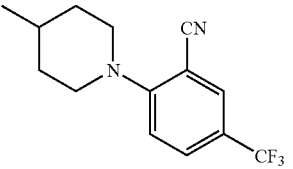 | (DMSO-d₆): 1.57(dq, 2H); 1.80 (dd, 2H); 2.23-2.34(m, 1H); 2.92(dt, 2H); 3.60(dt, 2H); 7.22(d, 1H); 7.79 (dd, 1H); 8.03(d, 1H); 8.33(s, 3H) |
| 96 |  | 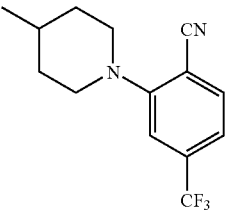 | (DMSO-d₆): 1.52-1.65(m, 2H); 1.73-1.84(m, 2H); 2.10-2.22 (m, 1H); 2.85(dt ,2H); 3.42-3.53(m, 2H); 7.30(s, 1H); 7.32(d, 1H); 7.87(d, 1H); 8.24 (s, 1H); 8.29(s, 2H) |
| 97 | 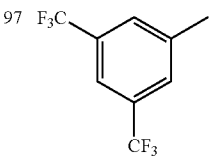 | 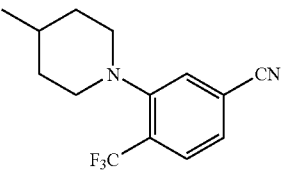 | (DMSO-d₆): 1.51(dq, 2H), 1.77 (m, 2H), 2.29(m, 1H), 2.74(t, 2H), 2.93(m, 2H), 7.74(d, 1H), 7.82(d, 1H), 7.98(s, 1H), 8.37 (s, 2H), 8.46(s, 1H). |
| 98 | 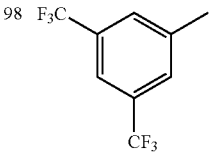 | 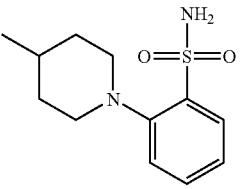 | (DMSO-d₆): 1.62-1.75(m, 2H); 1.78-1.86(m, 2H); 2.16-2.26 (m, 1H); 2.75(dt, 2H); 3.04-3.13(m, 2H); 7.37(dd, 1H); 7.52(d, 1H); 7.64(dd, 1H); 7.88 (d, 1H); 8.32(s, 1H); 8.38(s, 2H) |
| 99 | 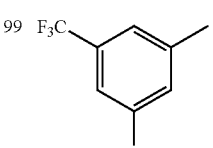 | 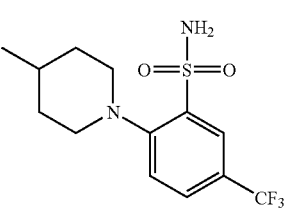 | (DMSO-d₆): 1.51-1.80(m, 4H), 2.13(m, 1H), 2.71(m, 1H), 3.12 (d, 1H), 7.59(d, 1H), 7.90(d, 1H), 8.07(s, 1H), 8.25(s, 1H), 8.30(s, 2H). |
| 100 | 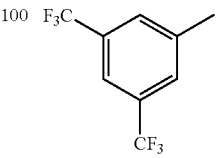 | 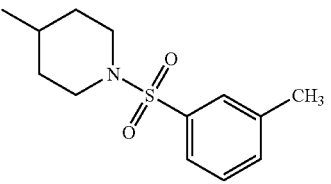 | (DMSO-d₆): 1.42(m, 2H), 1.76 (m, 2H), 2.19-2.33(m, 3H), 2.48 (s, 3H), 3.40-3.50(m, 2H), 7.47-7.55(m, 4H), 8.38(s, 2H), 8.56 (s, 2H) |
| 101 | 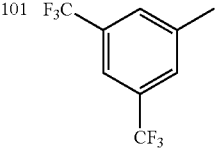 | 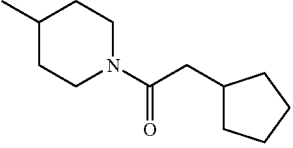 | 111-114° |
| 102 |  | 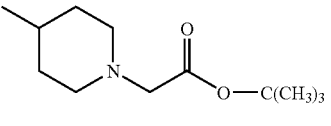 | 115-119° |

TABLE 1-continued
| EX | R$_1$ | R$_{16}$ + R$_{17}$ | m.p./$^1$H-NMR/$^{13}$C-NMR |
|---|---|---|---|
| 103 | 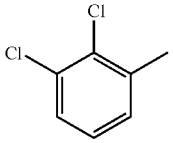 | 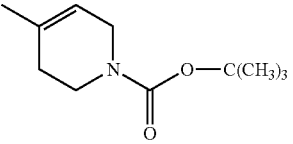 | 163.8, 154.77, 138.30, 136.01, 135.92, 132.04, 130.82, 128.04, 80.85, 28.77, 24.39 |
| 104 | 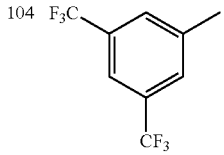 | 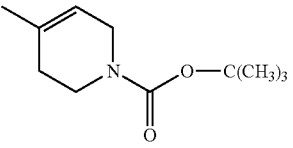 | 141.46, 136.06, 133.38, 133.04, 129.61, 128.03, 124.09, 121.37, 80.98, 28.75, 24.40 |
| 105 | 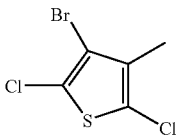 | 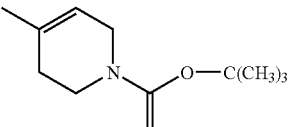 | 164.17, 154.79, 135.90, 130.75, 126.26, 108.61, 80.89, 28.78, 24.40 |
| 106 | 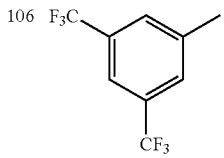 | 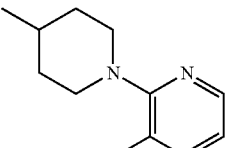 | (DMSO-d$_6$): 1.47(dq, 2H); 1.78 (dd, 2H); 2.51-2.57(m, 1H); 2.97(dt, 2H); 3.67(dt, 2H); 6.88 (dd, 1H); 8.22(dd, 1H); 8.38 (dd, 1H); 8.42(s, 2H); 8.54 (s, 1H) |
| 107 | 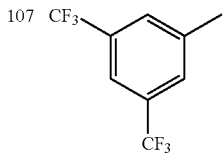 | 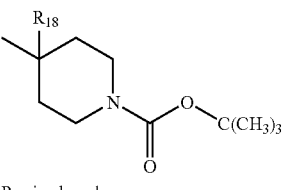
R$_{18}$ is phenyl | (DMSO-d$_6$): δ = 1.10-1.20(m, 2H); 1.32(s, 9H); 1.59(m, 2H); 2.42 (broad, 1H); 2.98(m, 2H); 3.70(m, 2H); 6.95-7.06(m, 3H); 7.16-7.21(m, 2H); 7.75(s, 1H); 8.10 (s, 2H) |
| 108 | 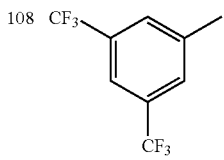 | 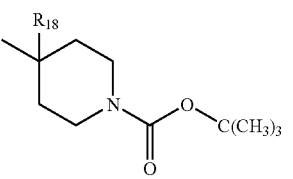
R$_{18}$ is methyl | 131-135° |

Analogously to methods as described in the PROCEDURES (Examples A to Q), but using appropriate starting materials, compounds of formula

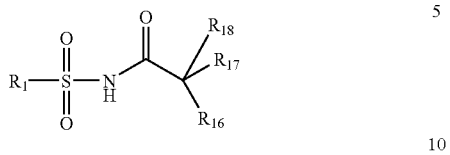

wherein $R_{18}$ is hydrogen and $R_1$ and $R_{16}+R_{17}$ are as defined in TABLE 2 (compounds of formula I, wherein m is 0, n is 0, and $R_1$ is a group of formula VII) are obtained. If not otherwise indicated in TABLE 2 $^1$HNMR and $^{13}$C-NMR data are determined in $CDCl_3$.

TABLE 2

| EX | $R_1$ | $R_{16}+R_{17}$ | m.p./$^1$H-NMR/$^{13}$C-NMR |
|---|---|---|---|
| 109 | 2,5-dichloro-3-bromo-4-methylthiophene | cyclohexylmethyl-NH-CO-O-C(CH$_3$)$_3$ | δ = 0.98(q, 2H); 1.42(s, 9H); 1.36-2.26(m, 8H); 2.98(t, 2H); 4.52(broad, 1H) |
| 110 | 2,5-dichloro-3-methylthiophene | cyclohexylmethyl-NH-CO-O-C(CH$_3$)$_3$ | 0.94(dq, 2H), 1.33-1.49(m, 12H), 1.83(broad d, 2H), 1.91 (broad d, 2H), 2.14(tt, 1H), 2.95(d, 2H), 7.28(s, 1H) |
| 111 | 2,3-dichloro-5-methylthiophene | cyclohexylmethyl-NH-CO-O-C(CH$_3$)$_3$ | 0.92(dq, 2H), 1.32-1.48(m, 12H), 1.65(broad, 1H), 1.82(d, 2H), 1.88(d, 2H), 2.09(tt, 1H), 2.93(d, 2H), 7.61(s, 1H) |
| 112 | 2,3-dibromo-5-methylthiophene | cyclohexylmethyl-NH-CO-O-C(CH$_3$)$_3$ | 0.93(dq, 2H), 1.35-1.50(m, 11H), 1.76-2.05(m, 5H), 2.10 (tt, 1H), 2.95(d, 2H), 4.72 (broad, 1H), 7.63(s, 1H) |
| 113 | 3-bromo-2-chloro-5-methylthiophene | cyclohexylmethyl-NH-CO-O-C(CH$_3$)$_3$ | 0.94(dq, 2H), 1.35-1.49(m, 12H), 1.78-1.93(m, 4H), 2.11 (tt, 1H), 2.94(d, 2H), 4.78 (broad, 1H), 7.65(s, 1H) |
| 114 | 3-bromo-2-chloro-5-methylpyridine | cyclohexylmethyl-NH-CO-O-C(CH$_3$)$_3$ | 0.92(dq, 2H), 1.31-1.46(m, 12H), 1.83(broad t, 2H), 2.03-2.14(m, 3H), 2.93(d, 2H), 4.72 (broad, 1H), 8.58(d, 1H), 8.87 (d, 1H) |
| 115 | 4-tert-butylphenyl | cyclohexylmethyl-NH-CO-O-C(CH$_3$)$_3$ | 0.90(m, 2H); 1.30(m, 1H); 1.38(s, 9H); 1.42(s, 9H); 1.75-2.20(m, 7H); 2.98(t, 2H); 4.52(broad, 1H); 7.55(d, 2H); 7.92(d, 2H); 8.30(s, 1H) |

TABLE 2-continued
| EX | R₁ | R₁₆ + R₁₇ | m.p./¹H-NMR/¹³C-NMR |
|---|---|---|---|
| 116 | 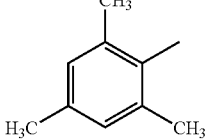 | 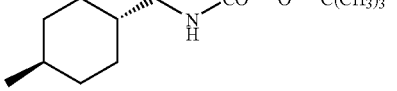 | 0.92(q, 2H); 1.41(s, 9H); 1.25-2.18(m, 8H); 2.35(s, 3H); 2.70 (s, 6H); 2.98(t, 2H); 4.50 (broad, 1H); 6.94(s, 2H); 8.52(s, 1H) |
| 117 | 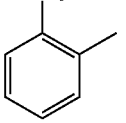 |  | 0.92(q, 2H); 1.42(s, 9H); 1.20-2.18(m, 8H); 2.94(t, 2H); 4.58 (broad, 1H); 7.78(t, 2H); 7.86 (m, 1H); 8.41(s, 1H); 8.50(dd, 1H) |
| 118 | 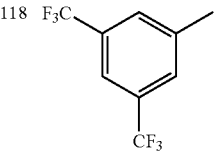 | 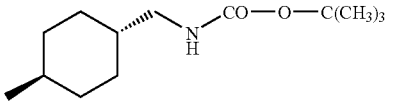 | 0.95(m, 2H); 1.20-2.30(m, 8H); 1.46(s, 9H); 3.00(t, 2H); 4.58 (broad, 1H); 8.06(s, 1H); 8.50 (s, 2H) |
| 119 | 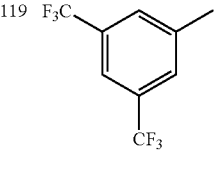 | 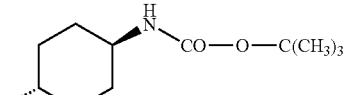 | 1.02(q, 2H); 1.39(s, 9H); 1.40-1.46 (m, 1H); 1.72-1.88(m, 5H); 2.08 (t, 1H); 3.30(broad, 1H); 4.48(d, 1H); 7.90(s, 1H); 8.35(s, 2H) |
| 120 | 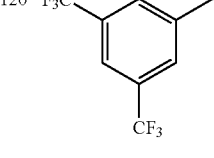 | 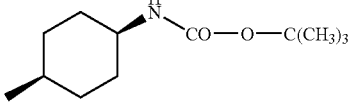 | 1.40(s, 9H); 1.40-1.80(m, 8H); 2.25(m, 1H); 3.55(m, 1H); 7.92 (s, 1H); 8.36(s, 2H) |
| 121 | 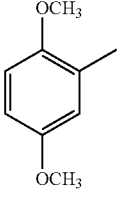 | 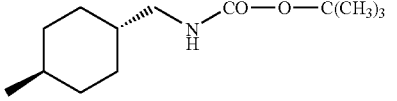 | 1.00(m, 2H); 1.30-2.00(m, 7H); 1.42(s, 9H); 2.20(t, 1H); .98(t, 2H); 3.80(s, 3H); 3.90(s, 3H); 5.58 (broad, 1H); 6.95(d, 1H); 7.14 (dd, 1H); 7.58(d, 1H); 8.50(s, 1H) |
| 122 | 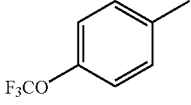 | 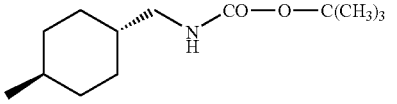 | 0.98(q, 2H); 1.41(s, 9H); 1.36-2.20(m, 8H); 2.98(t, 2H); 4.55 (broad, 1H); 7.30 and 8.10(2d, 4H); 8.13(s, 1H) |
| 123 | 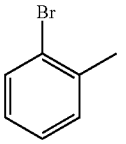 | 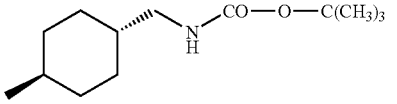 | 0.95(q, 2H); 1.43(s, 9H); 1.20-2.26(m, 8H); 2.95(t, 2H); 4.53 (broad, 1H); 7.40-7.55(m, 2H); 7.70 and 8.30(2dd, 2H); 8.46(s, 1H) |
| 124 | 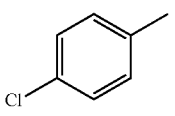 | 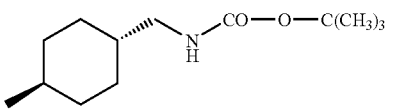 | 0.91(q, 2H); 1.40(s, 9H); 1.25-1.63(m, 3H); 1.78-2.18(m, 5H); 2.96(t, 2H); 4.58(broad, 1H); 7.50 and 7.98(AB, 2H); 8.38(s, 1H) |
| 125 | 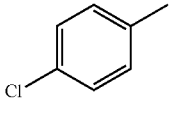 | 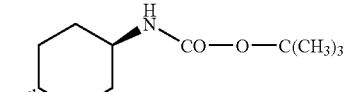 | 1.42(s, 9H); 1.54-1.78(m, 8H); 2.30(m, 1H); 3.64(m, 1H); 4.50 (broad, 1H); 7.51 and 7.99(AB, 4H); 8.36(broad, 1H) |

TABLE 2-continued
| EX | R₁ | R₁₆ + R₁₇ | m.p./$^1$H-NMR/$^{13}$C-NMR |
|---|---|---|---|
| 126 | 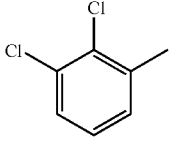 | 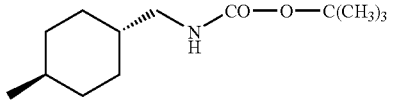 | 1.00(m, 2H); 1.30-2.00(m, 7H); 1.42(s, 9H); 2.20(t, 1H); 2.98 (t, 2H); 5.58(broad, 1H); 7.40 (t, 1H); 7.70(d, 1H); 8.22(d, 1H) |
| 127 | 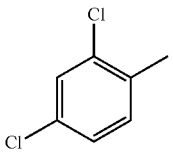 | 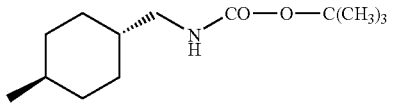 | 0.98(q, 2H); 1.41(s, 9H); 1.55-2.22(m, 8H); 2.85(t, 2H); 4.54 (broad, 1H); 7.42(dd, 1H); 7.52 (d, 1H); 8.19(d, 1H) |
| 128 | 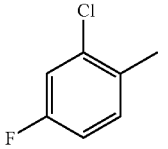 | 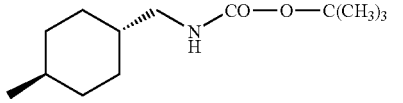 | 0.98(q, 2H); 1.40(s, 9H); 1.25-2.25(m, 8H); 2.98(t, 2H); 4.70 (broad, 1H); 7.13-7.24(m, 2H); 8.26(dd, 1H); 8.58(s, 1H) |
| 129 | 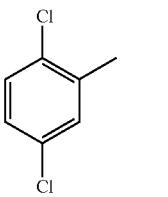 | 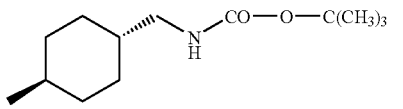 | 0.80-2.00(m, 9H); 1.42(s, 9H); 2.20(t, 1H); 2.98(t, 1H); 4.55 (broad, 1H); 7.36-7.50(m, 2H); 8.20(m, 2H) |
| 130 | 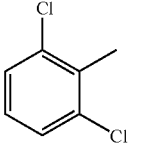 | 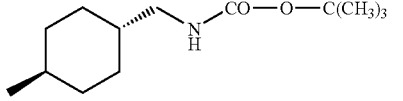 | 0.98(q, 2H); 1.43(s, 9H); 1.22-2.30(m, 8H); 2.98(t, 2H); 4.58 (broad, 1H); 7.30-7.58(m, 3H) |
| 131 | 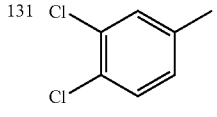 | 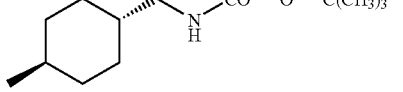 | 0.98(q, 2H); 1.41(s, 9H); 1.35-2.20(m, 8H); 2.98(t, 2H); 4.52 (broad, 1H); 7.60(d, 1H); 7.70(dd, 1H); 8.10(d, 1H) |
| 132 | 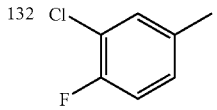 | 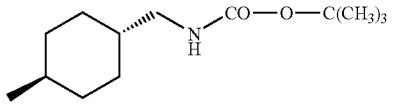 | 0.94(q, 2H); 1.40(s, 9H); 1.25-1.41(m, 2H); 1.70-1.96 (m, 5H); 2.10(t, 1H); 2.94(t, 2H); 4.58(broad, 1H); 7.30 (m, 1H); 7.96(m, 1H); 8.12 (m, 1H); 8.39(s, 1H) |
| 133 | 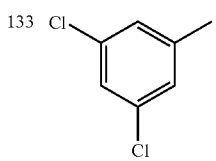 | 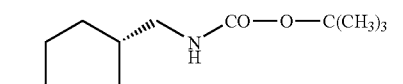 | 0.91(q, 2H); 1.40(s, 9H); 1.26-1.70 (m, 3H); 1.78-2.20(m, 5H); 2.95 (t, 2H); 4.52(broad, 1H); 7.54(m, 1H); 7.86(m, 2H); 8.50(s, 1H) |
| 134 | 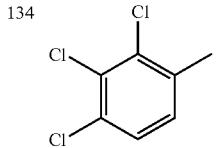 | 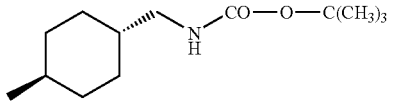 | 0.98(q, 2H); 1.42(s, 9H); 1.38-2.30 (m, 8H); 2.96(t, 2H); 4.54(broad, 1H); 7.60(d, 1H); 8.08(d, 1H) |

TABLE 2-continued
| EX | R₁ | R₁₆ + R₁₇ | m.p./¹H-NMR/¹³C-NMR |
|---|---|---|---|
| 135 | 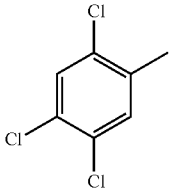 | 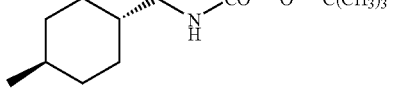 | (CDCl₃ + 10% DMSO-d₆) 0.98 (q, 2H); 1.42(s, 9H); 1.25-2.25(m, 8H); 2.95(d, 2H); 5.10(broad, 1H); 7.60(s, 1H); 8.24(s, 1H) |
| 136 | 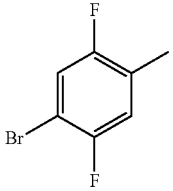 | 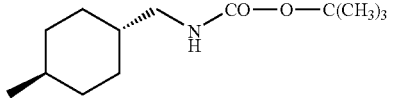 | 0.58-1.04(m, 2H); 1.42(s, 9H); 1.30-1.96(m, 7H); 2.16(m, 1H); 2.98(t, 2H); 4.58(broad, 1H); 7.48(dd, 1H); 7.82(dd, 1H); 8.65(s, 1H) |
| 137 | 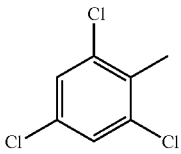 | 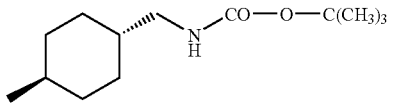 | 0.92(q, 2H); 1.42(s, 9H); 1.20-1.54(m, 2H); 1.70-2.20(m, 6H); 2.90(d, 2H); 7.42(s, 2H) |
| 138 | 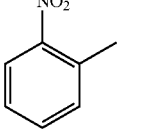 | 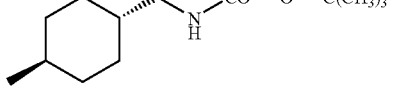 | 0.90(m, 2H); 1.20-2.30(m, 8H); 1.46(s, 9H); 2.98(t, 2H); 4.58 (broad, 1H); 7.75-7.82(m, 3H); 8.41(m, 1H) |
| 139 | 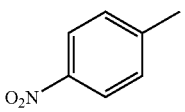 | 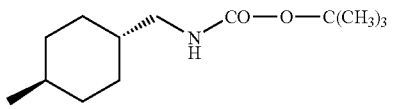 | 0.94(q, 2H); 1.42(s, 9H); 1.20-1.45(m, 1H); 1.60-2.20(m, 7H); 2.95(t, 2H); 4.58(broad, 1H); 8.23 and 8.38(AB, 4H), 8.60(s, 1H) |
| 140 | 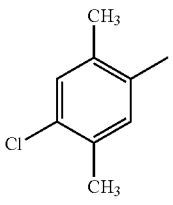 | 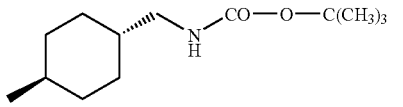 | (m, 2H); 1.30-2.00(m, 7H); 1.42 (s, 9H); 2.20(t, 1H); 2.40(s, 3H); 2.60(s, 3H); 2.98(t, 2H); 5.58(broad, 1H); 7.40(t, 1H); 7.70(d, 1H); 8.22(d, 1H) |
| 141 | 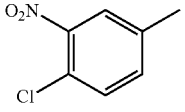 | 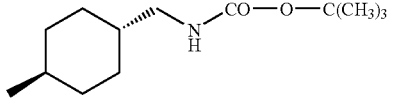 | 0.94(q, 2H); 1.41(s, 9H); 1.24-1.70(m, 2H); 1.80-2.20(m, 6H); 2.98(q, 2H); 4.58(broad, 1H); 7.75 (d, 1H); 8.22(dd, 1H); 8.46 (d, 1H); 8.54(s, 1H) |
| 142 | 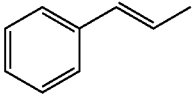 | 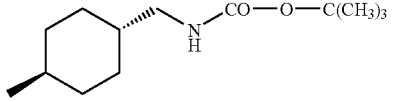 | 0.93(q, 2H); 1.40(s, 9H); 1.32-1.58(m, 2H); 1.78-2.20(m, 6H); 2.92(d, 2H); 7.04 and 7.62 (AB, 2H); 7.34-7.56(m, 5H) |
| 143 | 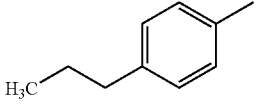 | 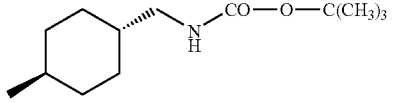 | 0.95(m, 4H); 1.30-2.20(m, 10H); 1.42(s, 9H); 2.70(t, 2H); 2.98(t, 2H); 4.56(broad, 1H); 7.30(d, 2H); 7.90(d, 2H); 8.18(s, 1H) |
| 144 | 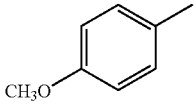 | 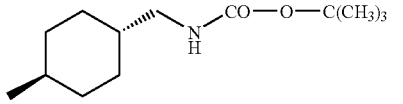 | 0.90(m, 2H); 1.20-2.20(m, 8H); 1.48(s, 9H); 2.98(t, 2H); 3.90(s, 3H); 4.55 (broad, 1H); 6.99(d, 2H); 8.00(d, 2H); 8.20(s, 1H) |

TABLE 2-continued

| EX | R$_1$ | R$_{16}$ + R$_{17}$ | m.p./$^1$H-NMR/$^{13}$C-NMR |
|---|---|---|---|
| 145 | 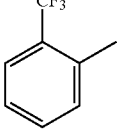 | 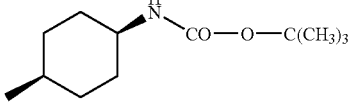 | CDCl$_3$ + 5% DMSO-d$_6$: 1.43 (s, 9H); 1.54-1.73(m, 4H); 2.32(m, 1H); 2.52-2.64(m, 4H); 3.76(m, 1H); 5.32(bd, 1H); 7.72-7.78(m, 2H); 7.84-7.88(m, 1H); 8.45-8.50(m, 1H) |
| 146 | 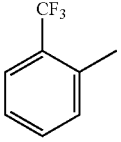 | 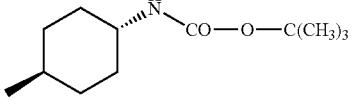 | CDCl$_3$ + 5% CD$_3$OD: 1.06(m, 2H); 1.40(s, 9H); 1.43(m, 2H); 1.84(m, 2H); 2.03(m, 2H); 2.08 (m, 1H); 3.30(broad, 1H); 7.71-7.77(m, 2H); 7.82-7.87(m, 1H); 8.46-8.51(m, 1H) |
| 147 | 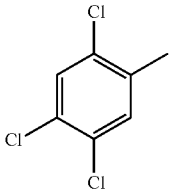 | 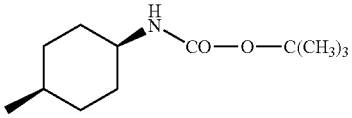 | CDCl$_3$ + 5% DMSO-d$_6$: 1.42(s, 9H); 1.55(m, 2H); 1.60-1.80(m, 6H); 2.38(m, 1H); 2.50(m, 2H); 3.75(m, 1H); 5.30(bd, 1H); 7.70(s, 1H); 8.30(s, 1H) |
| 148 | 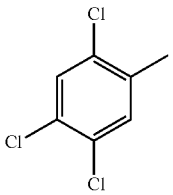 | 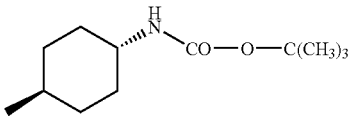 | CDCl$_3$ + 5% CD$_3$OD: 1.08(m, 2H); 1.42(s, 9H); 1.47(m, 2H); 1.88(m, 2H); 2.03(m, 2H); 2.12 (m, 1H); 2.31(broad, 1H); 7.59 (s, 1H); 8.31(s, 1H) |
| 149 | 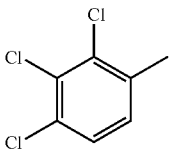 | 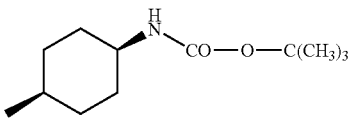 | CDCl$_3$ + 5% DMSO-d$_6$: 1.45(s, 9H); 1.50(m, 2H); 1.55-1.75(m, 4H); 2.32(m, 1H); 2.58(m, 2H); 3.77(m, 1H); 5.33(bd, 1H); 7.61(d, 1H); 8.13(d, 1H) |
| 150 | 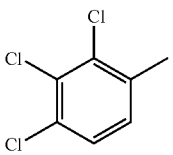 | 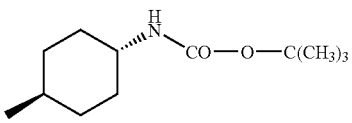 | CDCl$_3$ + 5% CD$_3$OD: 1.08(m, 2H); 1.40(s, 9H); 1.44(m, 2H); 1.86(m, 2H); 2.02(m, 2H); 2.10 (m, 1H); 3.28(m, 1H); 7.55(d, 1H); 8.11(m, 1H) |
| 151 | 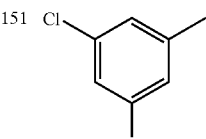 | 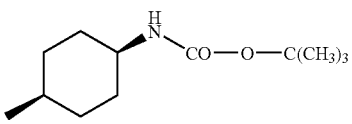 | CDCl$_3$ + 5% DMSO-d$_6$: 1.40(s, 9H); 1.50-1.78(m, 6H); 2.32(m, 1H); 2.54(m, 2H); 3.73(m, 1H); 5.22 (bd, 1H); 7.60(s, 1H); 7.90 (s, 1H) |
| 152 | 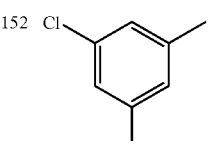 | 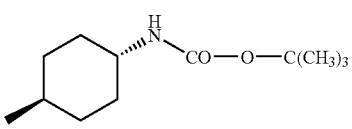 | CDCl$_3$ + 5% CD$_3$OD: 1.08(m, 2H); 1.40(s, 9H); 1.47(m, 2H); 1.85 (m, 2H); 2.04(m, 1H); 3.29 (broad, 1H); 7.56(t, 1H); 7.87(d, 1H) |
| 153 | 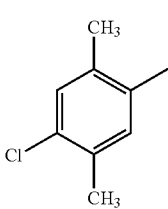 | 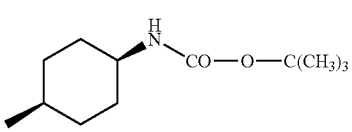 | CDCl$_3$ + 5% DMSO-d$_6$: 1.42(s, 9H); 1.70-1.80(m, 8H); 2.30(m, 1H); 2.40(s, 3H); 2.56(s, 3H); 3.77(m, 1H); 5.25(bd, 1H); 7.24(s, 1H); 7.98(s, 1H) |

TABLE 2-continued
| EX | R₁ | R₁₆ + R₁₇ | m.p./¹H-NMR/¹³C-NMR |
|---|---|---|---|
| 154 | 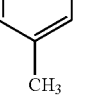 |  | CDCl₃ + 5% CD₃OD: 1.05(m, 2H); 1.38(s, 9H); 1.42(m, 2H); 1.80(m, 2H); 1.97(m, 2H); 2.07 (m, 1H); 2.35(s, 3H); 2.50(s, 3H); 3.25(broad, 1H); 7.22(s, 1H); 7.95(s, 1H) |
| 155 | 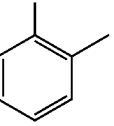 | 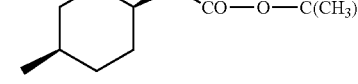 | CDCl₃ + 5% DMSO-d₆: 1.44(s, 9H); 1.54(m, 2H); 1.62-1.79(m, 4H); 2.33-2.44(m, 5H); 3.77 (broad, 1H); 5.28(bd, 1H); 7.41 (t, 1H); 7.71(dd, 1H); 8.20(dd, 1H) |
| 156 | 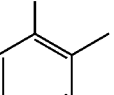 | 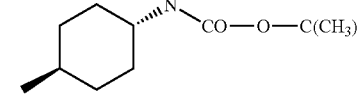 | CDCl₃ + 5% CD₃OD: 1.08(m, 2H); 1.40(s, 9H); 1.44(m, 2H); 1.86(m, 2H); 2.01(m, 2H); 2.12(m, 1H); 3.28(broad, 1H); 7.38(t, 1H); 7.68(dd, 1H); 8.18(dd, 1H) |
| 157 | 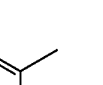 | 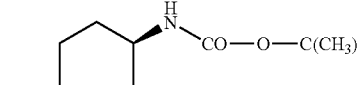 | CDCl₃ + 5% DMSO-d₆: 1.42(s, 9H); 1.55(m, 2H); 1.60-1.77(m, 4H); 2.35(m, 2H); 3.76(m, 1H); 5.24(m, 1H); 7.43(d, 1H); 7.50 (dd, 1H); 8.24(d, 1H) |
| 158 |  | 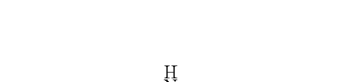 | CDCl₃ + 5% CD₃OD: 1.08(m, 2H); 1.41(m, 9H); 1.46(m, 2H); 1.88(m, 2H); 2.03(m, 2H); 2.13 (m, 1H); 3.28(broad, 1H); 7.39 (d, 1H); 7.48(dd, 1H); 8.20(d, 1H) |
| 159 | 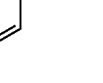 |  | 1.09(dq, 2H), 1.41(s, 9H), 1.52 (dq, 2H), 1.92(broad d, 2H), 2.05(broad, d, 2H), 2.15(tt, 1H), 3.32(broad, 1H) trans isomer |
| 160 | 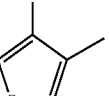 | 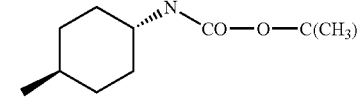 | (CDCl₃ + 5% DMSO-d₆): 23.814, 28.811, 29.586, 29.944, 44.056, 45.056, 79.296, 108.900, 125.462, 155.603, 175.574 |
| 161 |  | 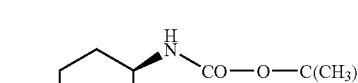 | 223-225° |

TABLE 2-continued
| EX | R₁ | R₁₆ + R₁₇ | m.p./¹H-NMR/¹³C-NMR |
|---|---|---|---|
| 162 | 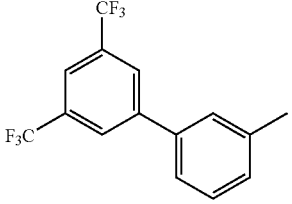 | 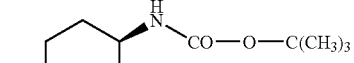 | (DMSO-d₆): 8.30(s, 2H), 8.15 (s, 2H), 8.07(d, J=7.82.16 (br.s, 1H), Hz, 1H), 7.92(d, J= 7.8Hz, 1H), 7.68(t, J=7.8 Hz, 1H), 1.35-1.73(m, 8H), 1.35(s, 9H) |
| 163 | 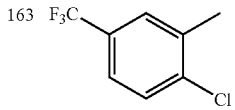 | 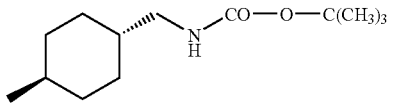 | DMSO-d₆: 0.77(m, 2H); 1.08 (m, 2H); 1.10(m, 1H); 1.32(s, 9H); 1.62(m, 2H); 1.72(m, 2H); 2.20(m, 1H); 2.70(t, 2H); 6.71 (t, 1H); 7.91(d, 1H); 8.07(dd, 1H); 8.22(d, 1H); 12.65(bs, 1H) |
| 164 | 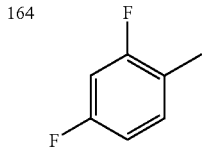 | 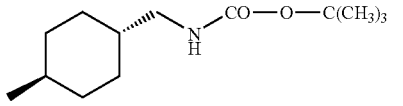 | 0.94(m, 2H); 1.32-1.50(m, 3H); 1.43(s, 9H); 1.83(m, 2H); 1.91 (m, 2H); 2.14(m, 1H); 2.97(t, 2H); 4.54(broad, 1H); 6.95(m, 1H); 7.06(m, m, 1H); 8.11(m, 1H); 8.68(bs, 1H) |
| 165 | 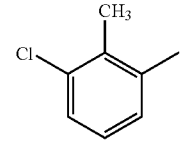 | 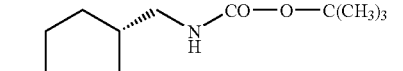 | 1.04(m, 2H); 1.32-1.50(m, 3H); 1.42(s, 9H); 1.82(m, 2H); 1.89 (m, 2H); 2.16(m, 1H); 2.68(s, 3H); 2.96(t, 2H); 4.55(broad, 1H); 7.33(t, 1H); 7.64(dd, 1H); 8.13(dd, 1H); 8.77(bs, 1H) |
| 166 | 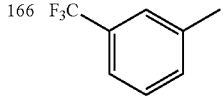 | 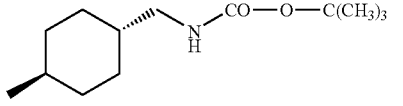 | 0.92(m, 2H); 1.32-1.50(m, 3H); 1.43(s, 9H); 1.82(m, 2H); 1.84 (m, 2H), 2.12(m, 1H); 2.96(t, 2H); 4.55(broad, 1H); 7.70(t, 1H); 7.89(d, 1H); 8.28(s, 1H); 8.31(s, 1H); 8.63(bs, 1H) |
| 167 | 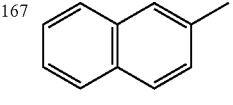 | 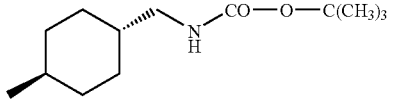 | 0.88(m, 2H); 1.25-1.48(m, 3H); 1.43(s, 9H); 1.81(m, 4H); 2.10(m, 1H); 2.92(t, 2H); 4.70(t, 1H); 7.57-7.69(m, 3H); 7.92(d, 1H); 7.96(s, 2H); 8.01(d, 1H); 8.63(s, 1H) |
| 168 | 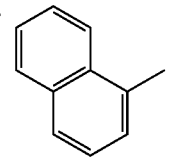 | 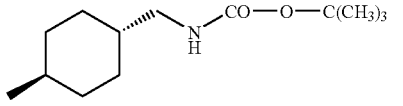 | 0.83(m, 2H); 1.22(m, 2H); 1.28 (m, 1H); 1.42(s, 9H); 1.72(m, 4H); 2.08(m, 1H); 2.90(t, 2H); 4.49(broad, 1H); 7.58-7.69(m, 3H); 7.98(d, 1H); 8.13(d, 1H); 8.52 (dd, 1H); 8.59(d, 1H); 9.03 bs, 1H) |
| 169 | 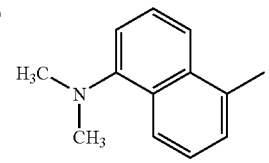 | 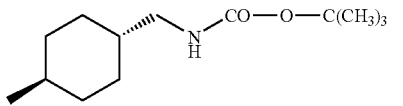 | 0.83(m, 2H); 1.17-1.36(m, 3H); 1.46(s, 9H); 1.74(t, 4H); 2.10 (m, 1H); 2.80-3.00(m, 2H); 2.94 (s, 6H); 4.52(broad, 1H); 7.23 (d, 1H); 7.53-7.64(m, 2H); 8.27 (d, 1H); 8.50(dd, 1H); 8.61(d, 1H); 9.15 bs, 1H) |
| 170 | 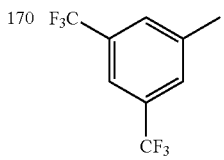 | 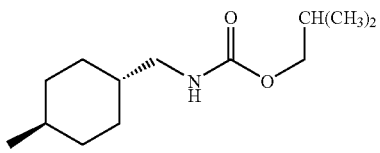 | 165-169° |

TABLE 2-continued

| EX | R₁ | R₁₆ + R₁₇ | m.p./¹H-NMR/¹³C-NMR |
|---|---|---|---|
| 171 | 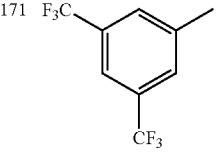 | 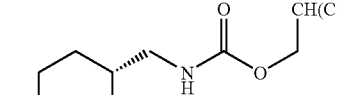 | 90-94° |
| 172 | 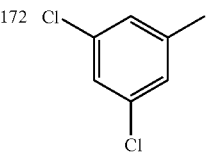 | 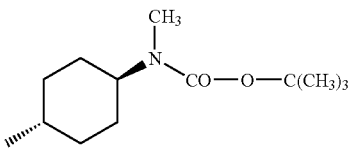 | (DMSO-d₆): 8.07(I, J=1.9Hz, 1H), 7.86(d, J=1.9Hz, 2H), 3.70(br.s, 1H), 2.64(s, 3H), 2.20(tt, J=3.3 + 8.6Hz, 1H), 1.23-1.64(m, 8 H), 1.38(s, 9H) |
| 173 | 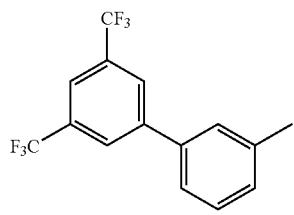 | 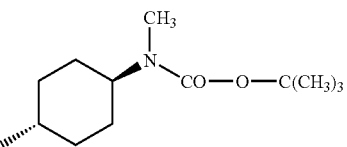 | (DMSO-d₆): 12.16(s, 1H), 8.37 (s, 2H), 8.20-8.25(m, 37.99-8.03(m, 1H), 7.81(t, J=7.9Hz, 1H), 3.69(br.s, 1H), 2.63(s, 3H), 2.19(tt, J=3.4 + 12Hz, 1H), 1.77-1.85(m, 2H), 1.21-1.63(m, 6H), 1.37(s, 9H) |
| 174 | 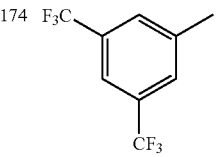 | 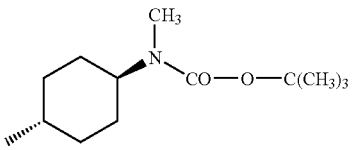 | (DMSO-d₆): 8.22(s, 2H), 8.15(s, 1H), 3.45-3.70(br.m, 1H), 2.60(s, 3H), 1.69-1.84(m, 3H), 1.36(s, 9H), 1.12-1.57 (m, 6H) |
| 175 | 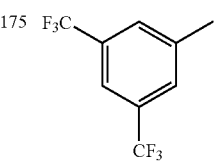 | 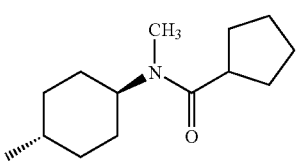 | (DMSO-d₆): 2 rotamers, selected signals: 12.47(br.s, 1H), 8.59(s, 1H), 8.42(s, 2H), 4.12 + 3.66(2 × m, 1H), 2.79 + 2.62(2 × s, 3H) |
| 176 | 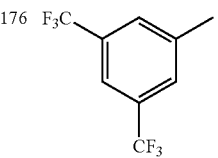 | 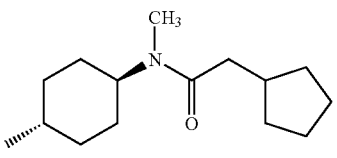 | (DMSO-d₆): 2 rotamers, selected signals: 12.41(br.s, 1H), 8.59(s, 1H), 8.42(s, 2H), 4.10-4.19(m, 1H), 2.74 + 2.61 (2 × s, 3H) |
| 177 | 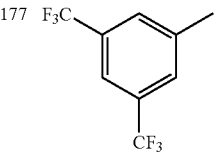 | 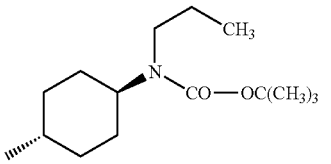 | 12.47(s, 1H), 8.60(s, 1H), 8.43 (s, 2H), 3.57(br.s, 1H), 2.96 (br.s, 2H), 2.19(tt, J=3.4 + 12Hz, 1H), 1.18-1.82(m, 10H), 1.37(s, 9H), 0.80(t, J=7Hz, 3H) |
| 178 | 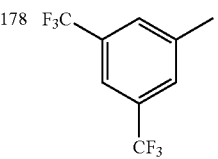 | 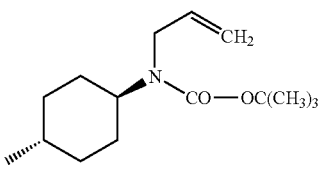 | (DMSO-d₆): 12.47(s, 1H), 8.59(s, 1H), 8.42(s, 2H), 5.68-5.78(m, 1H), 5.09(d, J=17.7Hz, 1H), 5.04(d, J=9Hz, 1H), 3.68 (br.s, 3H), 2.17(tt, J=3.2 + 9Hz, 1H), 1.16-1.67(m, 8H), 1.37(s, 9H) |

TABLE 2-continued
| EX | R₁ | R₁₆ + R₁₇ | m.p./¹H-NMR/¹³C-NMR |
|---|---|---|---|
| 179 | 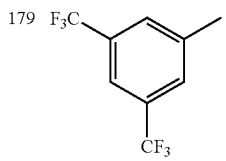 | 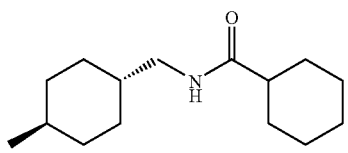 | 198-204° |
| 180 | 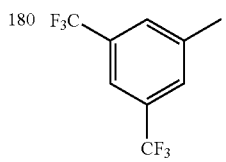 | 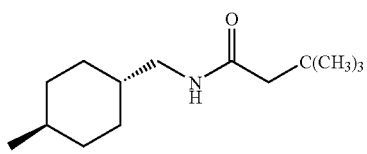 | 136-140° |
| 181 | 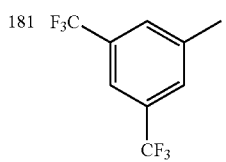 | 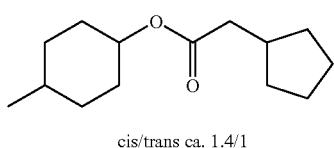<br>cis/trans ca. 1.4/1 | (DMSO-d₆): E/Z stereoisomers, selected signals: 12.5(br.s, 1H), 8.59(s, 1H), 8.41(s, 2H), 4.81 + 4.51(br.s + m, 1H) |
| 182 | 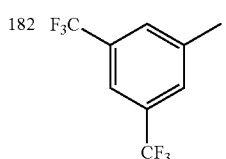 | 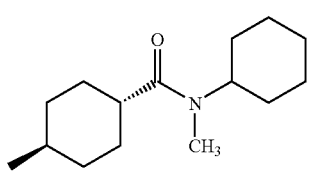 | 230-238° |
| 183 | 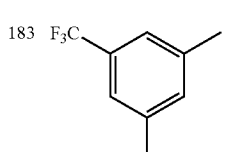 | 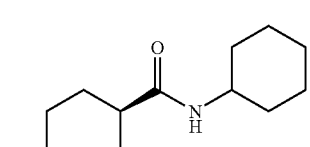 | 220-230° |
| 184 | 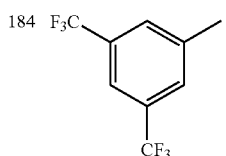 | 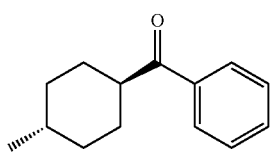 | 173-175° |
| 185 | 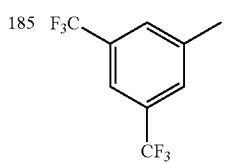 | 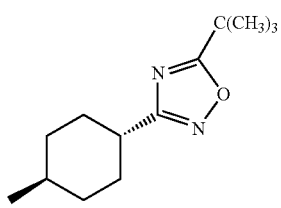 | (DMSO-d₆): 1.54(s, 9H), 1.55-1.77(m, 4H), 2.10(dd, 2H), 2.31(dd, 2H), 2.57(tt, 1H), 3.19 (tt, 1H), 8.68(s, 2H), 8.85(s, 1) |

Analogously to methods as described in the PROCEDURES (Examples A to Q), but using appropriate starting materials, compounds of formula

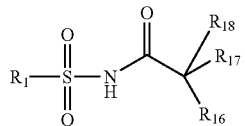

(5)

wherein $R_{18}$ is hydrogen and $R_1$ and $R_{16}+R_{17}$ are as defined in TABLE 3 (compounds of formula I, wherein m is 0, n is 0, and $R_1$ is a group of formula VII) are obtained. If not otherwise indicated in TABLE 3 $^{13}$C-NMR and $^1$HNMR data are determined in CDCl$_3$.

TABLE 3

| EX | R$_1$ | R$_{16}$ + R$_{17}$ | m.p./$^1$HNMR/$^{13}$C-NMR |
|---|---|---|---|
| 186 | 4-Cl-phenyl | bicyclic-CH$_3$ | (DMSO-d$_6$): δ = 0.80-0.95(m, 3H); 0.95-1.40(m, 10H); 1.50-1.75(m, 8H); 7.62/7.82(AB, 4H) |
| 187 | 3,5-(CF$_3$)$_2$-phenyl | bicyclic-CH$_3$ | 322-333° |
| 188 | 3,5-(CF$_3$)$_2$-phenyl | adamantyl-NH—CO—O—C(CH$_3$)$_3$ | 98-100°/(DMSO-d$_6$): 1.38/1.40 (s, 9H), 1.60-2.10(m, 12H); 3.41-3.57(m, 1H); 6.68/6.80(bd, 1H); 8.36/8.40 (s, 2H); 8.48/8.50(s, 1H) |
| 189 | 2,4,5-Cl$_3$-phenyl | adamantyl-NH—CO—O—C(CH$_3$)$_3$ | 1.47(s, 9H); 1.51-2.13(m, 12H); 3.72(m, 1H); 4.81(d, 1H); 7.60(s, 1H); 8.30(s, 1H) |
| 190 | 2,5-Cl$_2$-4-Br-thienyl | adamantyl-NH—CO—O—C(CH$_3$)$_3$ | 132-133° |
| 191 | 3,5-(CF$_3$)$_2$-phenyl | adamantyl-CH$_3$, N(CH$_3$)—CO—O—C(CH$_3$)$_3$ | 2 rotamers, selected signals: 8.55(s, 2H), 8.35 + 8.32(2x br, s, 1H), 8.16(s, 1H), 3.87 + 3.83 (2xs, 1H), 3.05 + 3.00(2xs, 3H); 2.40 + 2.32(2xs, 2H), 1.47(s, 9H) |

TABLE 3-continued
| EX | R₁ | R₁₆ + R₁₇ | m.p./¹HNMR/¹³C-NMR |
|---|---|---|---|
| 192 | 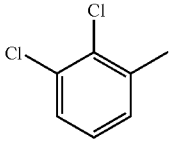 | 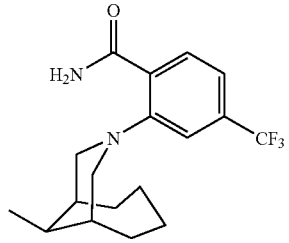 | (DMSO-d₆): 173.12, 170.12, 150.43, 136.52, 135.24, 133.86, 131.29, 130.04, 129.79, 129.19, 128.87, 128.47, 125.10, 122.94, 117.86, 115.85, 60.09, 47.76, 32.80, 31.60, 26.06 |
| 193 | 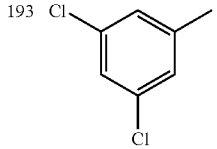 | 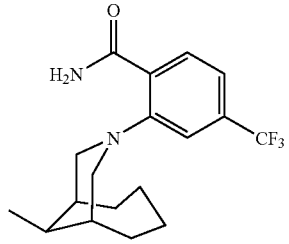 | (DMSO-d₆): 170.59, 150.93, 136.92, 135.02, 134.99, 130.44, 130.20, 129.63, 126.47, 125.56, 118.24, 116.16, 60.62, 48.20, 33.27, 32.02, 26.55 |
| 194 | 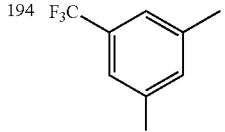 | 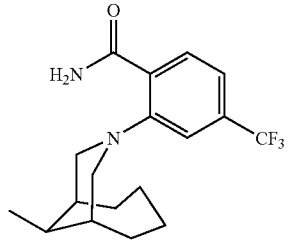 | (CDCl₃/DMSO-d₆): 173.42, 170.56, 151.37, 142.90, 134.67, 132.89, 132.61, 130.16, 129.31, 128.97, 128.51, 126.99, 119.30, 116.91, 61.47, 48.66, 33.60, 32.09, 26.78 |
| 195 | 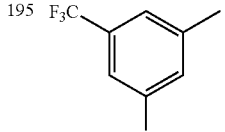 | 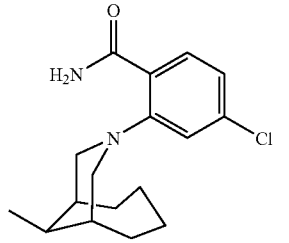 | (CDCl₃/DMSO-d₆): 173.72, 170.83, 152.28, 143.07, 136.26, 132.79, 132.52, 130.78, 130.13, 128.95, 127.04, 122.48, 121.83, 120.56, 61.41, 48.74, 33.65, 32.13, 26.82 |
| 196 | 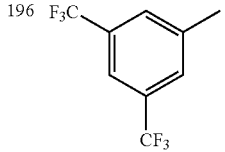 | 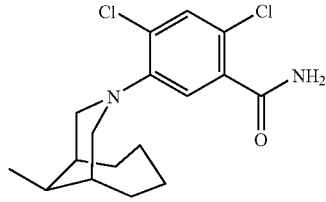 | 173.14, 167.61, 149.63, 142.55, 133.06, 132.70, 132.46, 132.37, 129.13, 127.26, 124.99, 124.20, 123.54, 60.42, 48.87, 40.38, 33.78, 32.27, 27.00 |
| 197 | 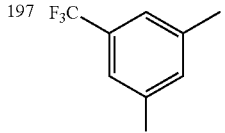 | 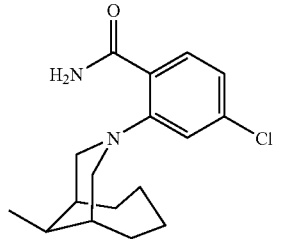 | 171.33, 141.88, 133.33, 133.06, 129.38, 127.69, 123.86, 62.30, 33.47, 31.79, 26.45 |

TABLE 3-continued
| EX | R₁ | R₁₆ + R₁₇ | m.p./¹HNMR/¹³C-NMR |
|---|---|---|---|
| 198 | 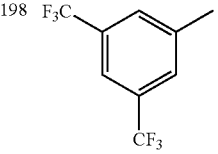 | 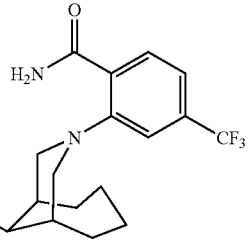 | 203.85, 171.03, 150.68, 141.52, 133.44, 133.17, 129.45, 128.13, 127.90, 119.82, 118.09, 61.87, 48.42, 33.89, 32.13, 31.92, 26.61 |
| 199 | 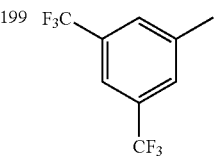 | 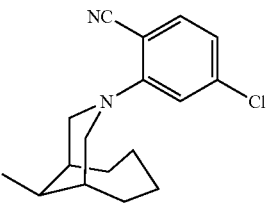 | 170.40, 154.09, 140.96, 138.32, 134.78, 133.31, 133.04, 132.76, 132.48, 129.06, 129.03, 127.61, 125.55, 123.38, 121.20, 117.12, 115.07, 112.97, 101.03, 55.60, 48.45, 33.07, 32.28, 26.09 |
| 200 | 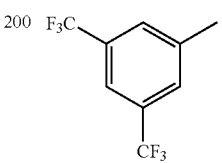 | 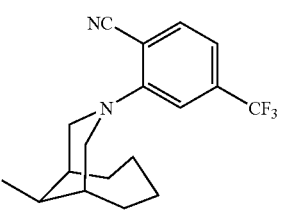 | 170.68, 155.72, 141.43, 136.12, 135.92, 133.49, 133.21, 132.93, 129.47, 127.98, 123.81, 121.63, 118.99, 118.97, 117.80, 116.45, 116.42, 109.19, 60.26, 48.41, 33.75, 32.02, 26.87 |
| 201 | 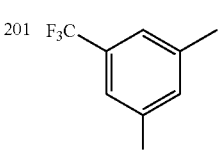 | 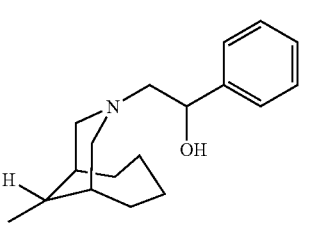 | 95-98° |
| 202 | 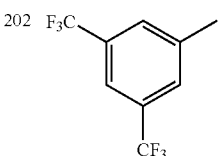 | 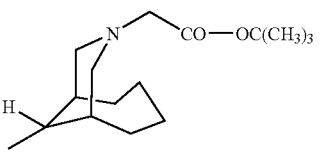 | 170.44, 132.95, 132.68, 132.41, 132.13, 127.36, 126.23, 125.66, 124.07, 121.89, 119.71, 81.09, 62.52, 61.35, 50.29, 33.16, 28.43, 27.16 |
| 203 | 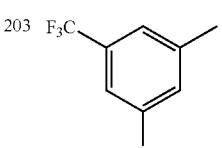 | 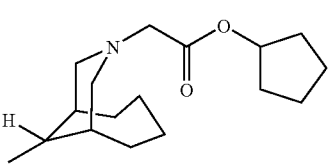 | 8.53(s, 2H), 8.11(s, 2H), 5.25 (m, 1H), 3.56(s, 2H), 3.13(bd, 2H), 2.98(bs, 1H), 2.88(bs, 1H), 2.67(bs, 2H), 2.21(s, 1H), 2.02(m, 2H), 1.83(m, 2H), 1.78-1.58(m, 10H), 1.40(m, 2H) |
| 204 | 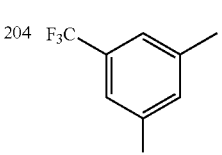 | 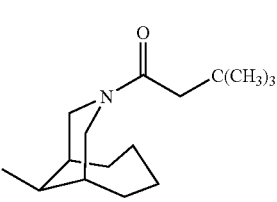 | 173.01, 171.44, 142.73, 133.31, 133.03, 132.76, 132.49, 129.07, 129.05, 127.18, 127.15, 127.12, 126.11, 123.93, 121.76, 119.59, 54.84, 49.82, 48.82, 45.09, 33.42, 32.25, 30.38, 27.01, 26.24 |

TABLE 3-continued
| EX | R₁ | R₁₆ + R₁₇ | m.p./¹HNMR/¹³C-NMR |
|---|---|---|---|
| 205 | 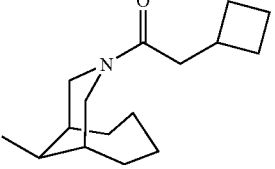 | 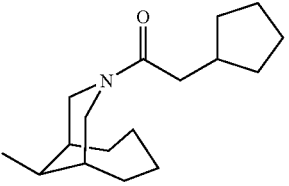 | 173.15, 142.63, 132.91, 132.56, 132.22, 128.98, 127.10, 124.14, 121.42, 53.68, 49.63, 48.88, 33.08, 32.61, 32.28, 28.89, 26.96, 26.25, 19.02 |
| 206 | 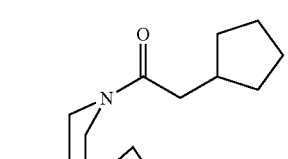 | | 172.71, 171.25, 141.71, 136.26, 134.33, 127.18, 127.11, 53.92, 49.49, 49.15, 39.74, 36.96, 33.50, 33.18, 32.72, 32.32, 32.11, 26.99, 26.20, 25.34 |
| 207 | 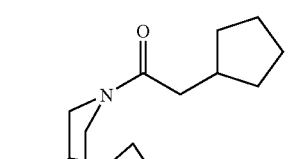 | | 172.45, 171.36, 138.44, 135.99, 135.85, 132.09, 130.50, 128.07, 53.80, 49.61, 49.18, 39.74, 36.89, 33.63, 33.24, 33.19, 32.08, 27.01, 26.32, 25.34 |
| 208 | 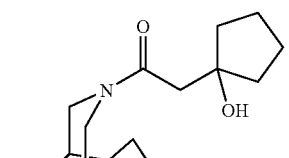 | | 173.15, 171.18, 141.69, 133.40, 133.12, 132.85, 129.35, 127.82, 123.82, 121.64, 54.00, 49.41, 49.25, 39.67, 37.02, 33.53, 33.21, 33.14, 32.26, 32.04, 26.92, 26.13, 25.29 |
| 209 | | 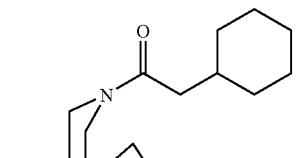 | 172.78, 172.45, 142.56, 133.41, 133.07, 132.72, 132.38, 129.10, 127.25, 124.18, 121.46, 80.19, 53.66, 49.62, 48.74, 42.62, 33.21, 33.08, 32.37, 32.26, 30.05, 27.02, 26.21, 24.28, 24.18 |
| 210 | | 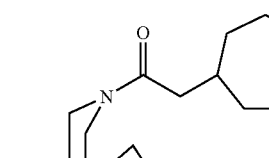 | 172.78, 171.30, 141.74, 133.38, 133.10, 129.37, 127.78, 123.83, 54.12, 49.46, 49.24, 41.21, 35.46, 33.82, 33.54, 33.23, 32.29, 32.01, 26.92, 26.54, 26.49, 26.12 |
| 211 | | 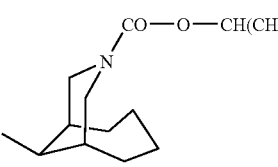 | 173.83, 171.03, 141.51, 133.77, 133.42, 133.08, 132.73, 129.39, 127.91, 126.77, 124.06, 121.34, 118.82, 54.21, 49.48, 49.22, 41.58, 37.19, 35.15, 35.08, 33.48, 33.13, 32.19, 31.93, 28.533, 26.89, 26.51, 26.44, 26.07 |
| 212 | | CO—O—CH(CH₃)₂ | 171.16, 155.61, 141.55, 133.42, 133.14, 129.39, 127.87, 123.81, 69.31, 49.48, 33.34, 32.03, 26.60, 22.61 |

TABLE 3-continued
| EX | R$_1$ | R$_{16}$ + R$_{17}$ | m.p./$^1$HNMR/$^{13}$C-NMR |
|---|---|---|---|
| 213 | 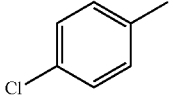 | 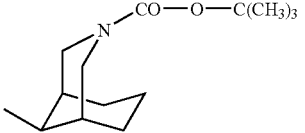 | 130.45, 130.21, 129.74, 129.65, 80.35, 49.41, 32.09, 28.86 mix |
| 214 | 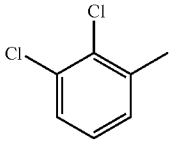 | 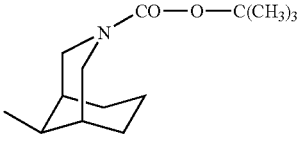 | 171.46, 155.14, 138.41, 135.99, 135.85, 132.10, 130.49, 128.07, 80.40, 49.65, 33.28, 32.01, 28.86, 26.67 |
| 215 | 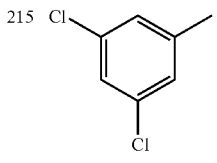 | 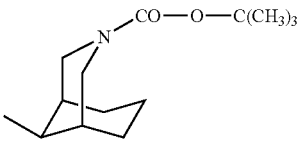 | 171.26, 155.28, 141.51, 136.30, 134.42, 127.21, 127.04, 80.69, 49.49, 33.21, 32.08, 28.86, 26.58 |
| 216 | 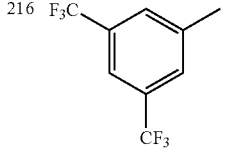  Diastereoisomeric mixture | 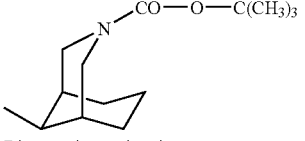 | Diastereoisomeric mixture of compounds of Example 217 and Example 218 |
| 217 | 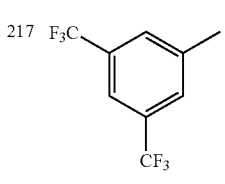  Pure isomer | 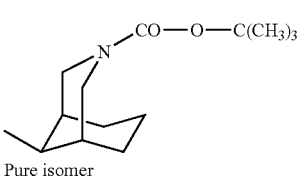 | 170.84, 154.71, 141.06, 133.27, 132.99, 132.99, 132.72, 132.44, 129.03, 129.00, 127.54, 127.52, 123.39, 121.22, 80.07, 49.04, 32.83, 31.66, 28.45, 26.15 |
| 218 | 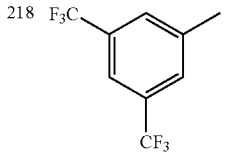  Pure isomer | 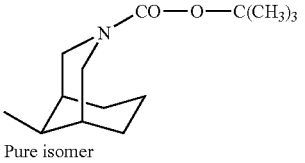 | 173.68, 155.62, 141.76, 133.75, 133.41, 133.07, 132.72, 129.26, 127.89, 124.09, 121.37, 80.23, 61.00, 44.81, 34.22, 33.21, 28.93, 28.89, 26.82 |
| 219 | 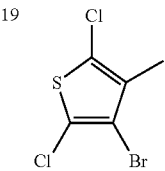 | 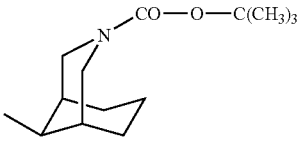 | 173.79, 155.30, 80.49, 45.50, 44.28, 37.87, 30.93, 30.63, 28.90, 28.83, 27.82, 13.83 |
| 220 | 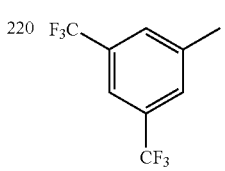 | 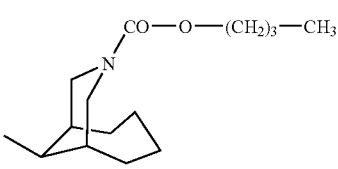 | 171.37, 156.23, 141.64, 133.68, 133.41, 133.13, 132.85, 129.34, 127.83, 123.81, 121.64, 65.96, 51.73, 49.44, 33.21, 32.11, 31.48, 26.61, 19.53, 14.03 |
| 221 | 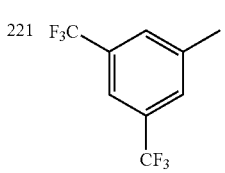 | 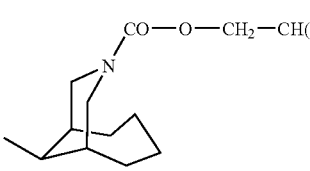 | 171.50, 156.20, 141.72, 133.68, 133.40, 133.13, 132.85, 129.33, 127.79, 123.82, 121.65, 119.47, 72.28, 49.47, 33.23, 32.12, 28.41, 26.62, 19.41 |

TABLE 3-continued
| EX | R₁ | R₁₆ + R₁₇ | m.p./¹HNMR/¹³C-NMR |
|---|---|---|---|
| 222 | 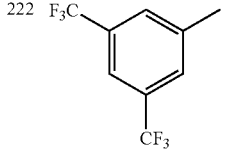 | 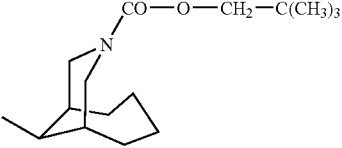 | 171.10, 156.11, 141.55, 133.71, 133.44, 133.16, 132.88, 129.41, 127.88, 123.81, 121.63, 75.56, 49.40, 33.25, 32.12, 31.88, 26.87, 26.63 |
| 223 | 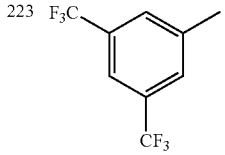 | 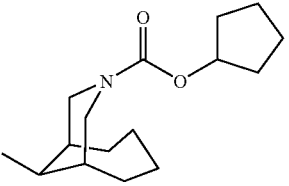 | 171.26, 155.81, 141.52, 133.76, 133.41, 133.07, 132.72, 129.40, 127.87, 124.06, 121.35, 118.63, 51.20, 49.41, 33.29, 32.08, 26.60, 23.96 |
| 224 | 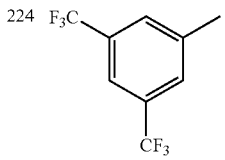 | 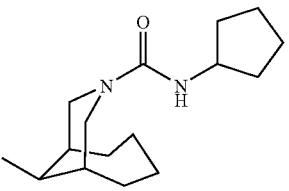 | 173.17, 157.69, 142.62, 133.03, 132.69, 129.06, 127.21, 124.20, 121.48, 53.07, 51.98, 49.66, 34.01, 33.20, 33.12, 32.49, 26.63, 24.03 |
| 225 | 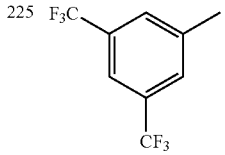 | 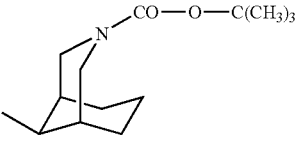<br>Diastereoisomeric mixture | 171.86, 171.29, 155.31, 155.12, 141.65, 133.43, 133.08, 129.35, 127.93, 124.07, 121.35, 80.49, 80.21, 47.63, 47.30, 28.87, 26.44, 19.90, 19.43 |
| 226 | 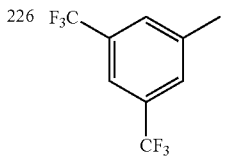 | 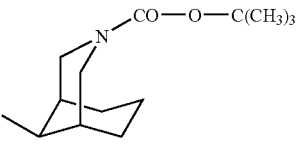<br>Pure isomer of unknown stereochemistry | 155.48, 132.98, 132.64, 132.30, 131.96, 127.76, 127.13, 125.79, 124.41, 121.70, 118.98, 79.63, 48.08, 45.69, 44.59, 40.33, 40.12, 32.82, 32.70, 30.55, 30.40, 28.88, 20.16 |
| 227 | 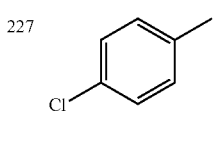 | 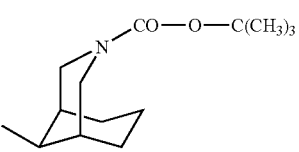 | 171.68, 171.14, 155.27, 155.10, 141.23, 137.28, 130.35, 130.26, 129.78, 129.73, 80.38, 80.10, 47.58, 47.24, 28.89, 26.44, 19.94, 19.47 mix |
| 228 | 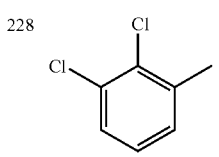 | 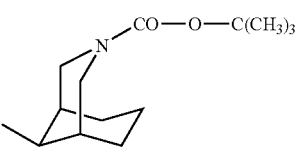 | 171.78, 171.30, 136.09, 136.04, 131.99, 131.91, 128.12, 80.34, 80.03, 47.73, 47.38, 28.89, 26.38, 19.46 |
| 229 | 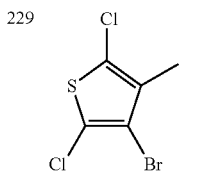 | 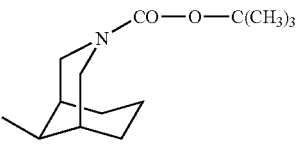 | 172.12, 171.64, 155.11, 131.24, 108.50, 80.42, 80.13, 508.94, 47.81, 47.43, 30.43, 28.90, 26.49, 19.95, 19.49 |

TABLE 3-continued

| EX | R₁ | R₁₆ + R₁₇ | m.p./¹HNMR/¹³C-NMR |
|---|---|---|---|
| 230 | 3,5-bis(CF₃)-phenyl | N-Boc bicyclic (CO—O—C(CH₃)₃) | 171.96, 153.20, 141.06, 133.03, 132.69, 128.99, 127.59, 80.04, 36.97, 28.45 |
| 231 | 2,3-dichlorophenyl (with methyl) | N-Boc bicyclic | 174.00, 153.35, 139.11, 135.50, 135.37, 131.59, 130.46, 127.77, 79.63, 40.66, 40.45, 40.24, 40.04, 36.49, 32.90, 28.81 |
| 232 | 2,5-dichloro-3-bromo-4-methylthienyl | N-Boc bicyclic | 172.19, 153.03, 137.04, 130.71, 125.99, 108.01, 79.83, 36.68, 32.67, 28.48 |
| 233 | 3,5-bis(CF₃)-phenyl | N-Boc benzo-fused bicyclic | 170.84, 155.33, 141.38, 138.52, 133.61, 133.26, 132.92, 132.57, 129.61, 129.42, 127.87, 126.98, 124.13, 121.41, 118.69, 80.37, 50.56, 49.24, 48.24, 35.17, 31.36, 31.05, 28.66 |
| 234 | 2,3-dichlorophenyl (with methyl) | N-Boc benzo-fused bicyclic | 171.09, 154.50, 138.81, 138.36, 136.07, 135.96, 132.06, 130.53, 129.88, 128.35, 128.07, 127.09, 126.94, 79.87, 50.88, 48.44, 47.60, 36.29, 31.26, 30.97, 28.61 |
| 235 | 2,5-dichloro-3-bromo-4-methylthienyl | N-Boc benzo-fused bicyclic | 171.49, 154.44, 138.78, 138.65, 137.68, 131.04, 129.90, 129.38, 127.09, 126.90, 126.33, 108.55, 79.87, 50.95, 48.37, 47.51, 36.45, 31.20, 30.82, 28.61 |
| 236 | 2,3-dichlorophenyl (with methyl) | N-Boc bicyclic (larger) | 173.58, 171.44, 155.56, 155.21, 138.38, 136.03, 136.00, 135.85, 132.09, 131.85, 130.47, 128.11, 128.08, 80.54, 80.23, 49.60, 44.82, 33.17, 32.01, 28.89, 28.86, 26.83 |
| 237 | 2,5-dichloro-3-bromo-4-methylthienyl | N-Boc bicyclic (larger) | 171.57, 155.09, 50.39, 49.69, 33.15, 32.01, 28.09 |
| 238 | 3,5-bis(CF₃)-phenyl | N-Boc decahydroisoquinoline-type | 173.55, 155.37, 142.08, 133.28, 132.94, 129.23, 127.63, 124.13, 121.42, 80.83, 45.58, 44.58, 37.76, 30.86, 30.55, 29.39, 28.87, 27.50, 13.73 |

TABLE 3-continued

| EX | R$_1$ | R$_{16}$ + R$_{17}$ | m.p./$^1$HNMR/$^{13}$C-NMR |
|---|---|---|---|
| 239 | 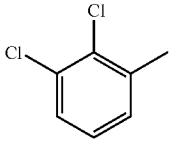 | 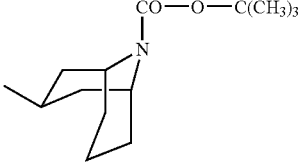 | 172.84, 154.11, 138.23, 136.07, 135.96, 131.90, 131.82, 130.46, 128.07, 80.03, 46.23, 44.69, 39.57, 31.81, 29.31, 28.88, 28.84, 20.37 |
| 240 | 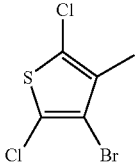 | 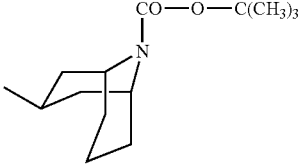 | 173.14, 154.11, 137.49, 131.08, 126.35, 108.46, 80.83, 46.20, 44.66, 39.61, 31.90, 31.74, 29.34, 28.83, 28.86, 20.41 |

Analogously to methods as described in the PROCEDURES (Examples A to Q), but using appropriate starting materials, compounds of formula

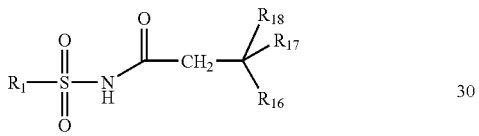

wherein R$_1$, R$_{16}$+R$_{17}$ are as defined in TABLE 4 and R$_{18}$ is hydrogen or is as defined in TABLE 4 (compounds of formula I, wherein m is 0, n is 1, and R$_1$ is a group of formula VII) are obtained. If not otherwise indicated in TABLE 4, characterisation data is $^1$HNMR data, and $^{13}$C-NMR and $^1$HNMR data are determined in CDCl$_3$.

TABLE 4

| EX | R$_1$ | R$_{16}$ + R$_{17}$/R$_{18}$ | m.p./$^1$H-NMR/$^{13}$C-NMR |
|---|---|---|---|
| 241 | 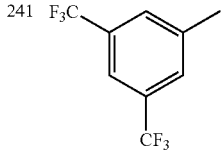 | 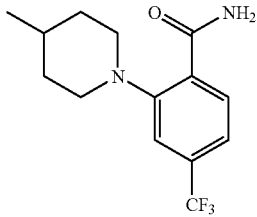 | (DMSO-d$_6$): δ = 1.25(dq, 2H); 1.59(d, 2H); 1.70(m, 1H); 1.97 (d, 2H); 2.66(t, 2H); 3.12(d, 2H); 7.30(s, 1H); 7.35(d, 1H); 7.62(s, 1H); 7.73(d, 1H); 8.19 (s, 1H); 8.27(s, 1H); 8.29(s, 2H). |
| 242 | 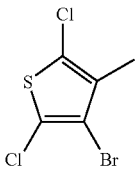 | 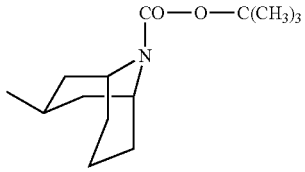 | 170.39, 170.31, 155.44, 154.43, 131.45, 126.22, 108.68, 79.91, 79.80, 47.36, 45.93, 45.86, 45.67, 44.61, 42.52, 36.84, 36.46, 32.10, 31.95, 31.25, 30.90, 30.08, 29.29, 29.17, 28.92, 27.53, 20.44, 14.02 |

TABLE 4-continued
| EX | R₁ | R₁₆ + R₁₇/R₁₈ | m.p./¹H-NMR/¹³C-NMR |
|---|---|---|---|
| 243 | 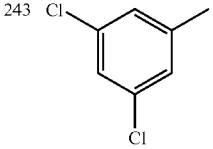 | 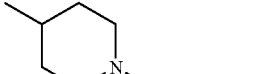 | (DMSO-d₆): 0.92(m, 2H); 1.35(s, 9H); 1.42(m, 2H); 1.74(m, 1H); 2.10(d, 2H); 2.54-2.70(m, 2H); 3.77-3.88 (d, 2H); 7.80(d, 2H); 7.97(t, 1H) |
| 244 | 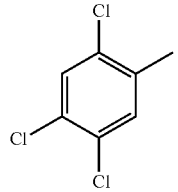 | 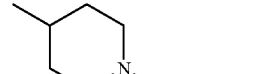 | 1.02-1.15(m, 2H); 1.44(s, 9H); 1.56-1.68(m, 2H); 1.83-1.95(m, 1H); 2.12-2.25(m, 2H); 2.57-2.73(m, 2H); 3.91-4.10(m, 2H); 7.56(s, 1H); 8.23(s, 1H) |
| 245 | 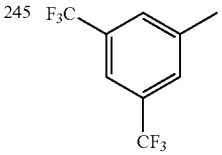 | 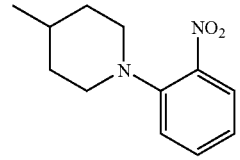 | (DMSO-d₆): 1.20(dq, 2H); 1.51(d, 2H); 1.73(m, 1H); 2.20(d, 2H); 2.70(dt, 2H); 3.06(d, 2H); 7.05(t, 1H); 7.24(d, 1H); 7.52(t, 1H); 7.74(d, 1H); 8.41(s, 2H); 8.53(s, 1H) |
| 246 | 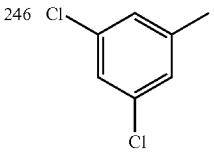 | 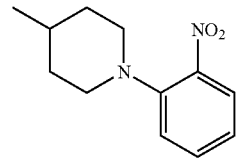 | (DMSO-d₆): 1.09(dq, 2H); 1.43(d, 2H); 1.63(m, 1H); 2.09(d, 2H); 2.51(t, 2H); 2.97(d, 2H); 6.95(t, 1H); 7.14(d, 1H); 7.42(ddd, 1H); 7.64(dd, 1H); 7.72(d, 2H); 7.90(t, 1H) |
| 247 | 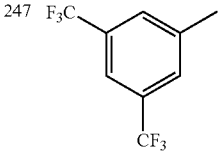 | 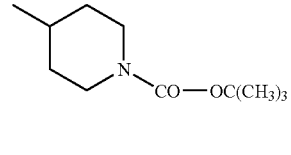 | 1.03-1.14(m, 2H), 1.44(s, 9H); 1.55-1.65(m, 2H); 1.88-1.96(m, 1H); 2.16-2.23(m, 2H); 2.61-2.77(m, 2H); 3.98-4.10(m, 2H); 8.12(s, 1H); 8.50(s, 2H) |
| 248 | 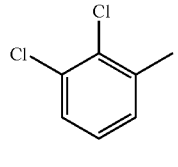 | 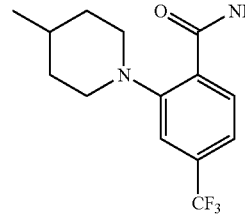 | 247-251° |
| 249 | 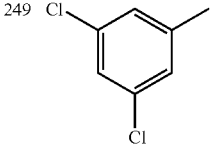 | 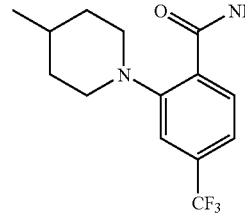 | 195-198° |
| 250 | 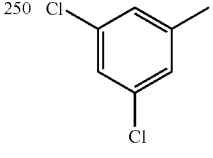 | 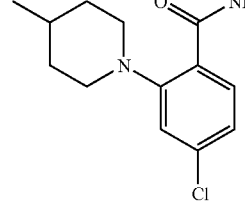 | 149-152° |

TABLE 4-continued
| EX | R₁ | R₁₆ + R₁₇/R₁₈ | m.p./¹H-NMR/¹³C-NMR |
|---|---|---|---|
| 251 | 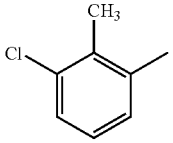 | 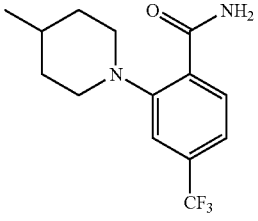 | 243-246° |
| 252 | 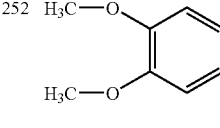 | 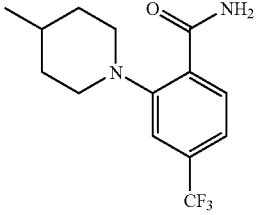 | 179-183° |
| 253 | 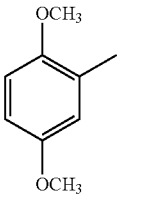 | 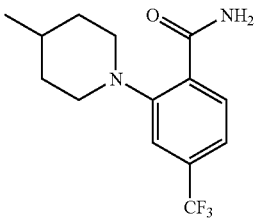 | 92-95° |
| 254 | 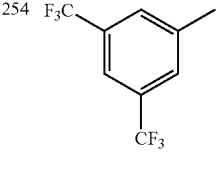 | 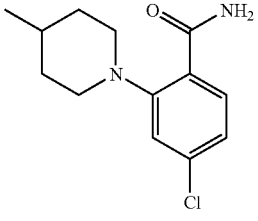 | 81-83° |
| 255 | 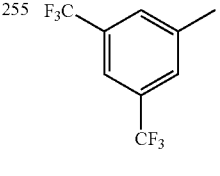 | 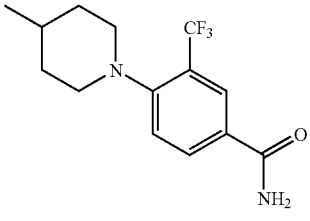 | 150-153° |
| 256 | 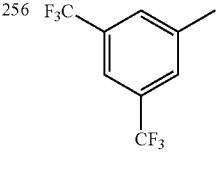 | 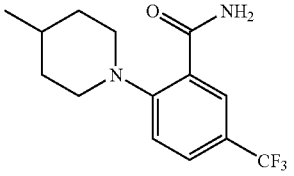 | 174-178° |

TABLE 4-continued

| EX | R₁ | R₁₆ + R₁₇/R₁₈ | m.p./¹H-NMR/¹³C-NMR |
|---|---|---|---|
| 257 | 3,5-bis(CF₃)phenyl | 4-methylpiperidinyl-2-(N,N-dimethylcarbamoyl)-4-CF₃-phenyl | 129-133° |
| 258 | 3,5-bis(CF₃)phenyl | 4-methylpiperidinyl-2-carbamoyl-4-CF₃-phenyl | 93-96° |
| 259 | 3,5-bis(CF₃)phenyl | 4-methylpiperidinyl-N-sulfonyl-2-CF₃-phenyl | 1.10(q, 2H), 1.52-1.61(m, 3H), 1.93(d, 2H), 2.25(t, 2H), 3.48(d, 2H), 7.89-7.94(m, 2H), 8.05(broad d, 1H), 8.12 (broad d, 1H), 9.29(broad s, 2H), 8.30(broad s, 1H) |
| 260 | 3,5-bis(CF₃)phenyl | 4-methylpiperidinyl-N-(cyclopentylacetyl) | 98-101° |
| 261 | 3,5-bis(CF₃)phenyl | 3,4-dimethylpiperidinyl-N-CO—OC(CH₃)₃ | 170.70, 170.43, 155.84, 155.24, 41.82, 141.76, 133.73, 133.38, 133.03, 132.69, 129.27, 127.80, 126.60, 124.08, 121.37, 80.47, 80.32, 43.61, 41.02, 39.59, 36.32, 32.34, 28.79, 16.68 |
| 262 | 2,3-dichloro-phenyl | 3,4-dimethylpiperidinyl-N-CO—OC(CH₃)₃ | 170.77, 170.45, 155.71, 155.13, 138.41, 135.99, 135.93, 131.90, 131.87, 130.57, 130.54, 128.03, 80.16, 80.03, 43.61, 40.73, 39.54, 36.03, 35.82, 32.22, 31.56, 28.82, 26.66, 16.72, 11.66 |
| 263 | 3,5-bis(CF₃)phenyl | 4-methylpiperazinyl-2-carbamoyl-4-CF₃-phenyl | 160-165° |
| 264 | 3,5-bis(CF₃)phenyl | 4-methylpiperazinyl-N-(2-nitrophenyl) | 140-150° |

TABLE 4-continued
| EX | R₁ | R₁₆ + R₁₇/R₁₈ | m.p./¹H-NMR/¹³C-NMR |
|---|---|---|---|
| 265 | 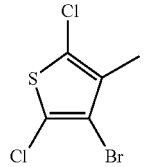 | 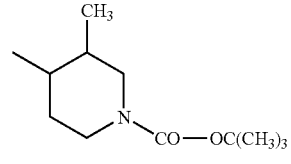 | 170.88, 170.52, 155.65, 155.07, 137.33, 137.25, 131.35, 126.34, 108.63, 108.58, 80.11, 79.96, 40.78, 39.51, 36.04, 35.73, 32.25, 31.69, 28.83, 16.78 |
| 266 | 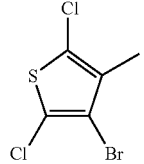 | 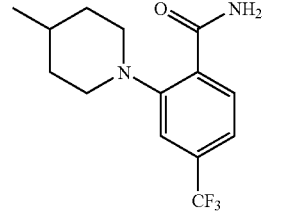 | 153-156° |
| 267 | 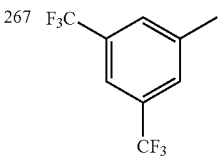 | 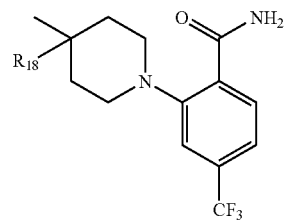<br>R₁₈ = OH | (DMSO-d₆): 1.42-1.65(m, 4H), 2.85-3.05(m, 4H), 3.55(s, 2H), 5.72(s, 1H, OH), 7.32(s, 1H), 7.34(d, 1H), 7.59 and 8.18(2s, 2H, NH), 7.72(d, 1H), 8.18(s, 1H), 8.26(s, 2H) |
| 268 | 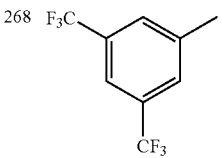 | 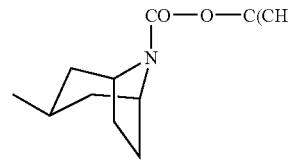 | 170.85, 170.22, 153.88, 142.03, 133.25, 132.91, 129.31, 127.60, 121.42, 80.45, 43.90, 43.58, 35.59, 28.92, 28.81, 28.18, 26.72, 25.67 |
| 269 | 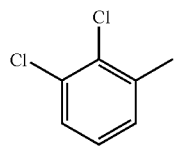 | 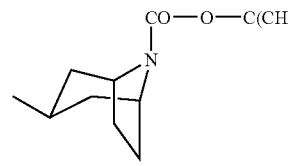 | 170.22, 153.77, 138.56, 135.99, 138.88, 131.82, 130.62, 128.03, 127.96, 80.00, 44.08, 43.57, 28.94, 28.86, 26.25, 25.44 |
| 270 | 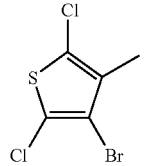 | 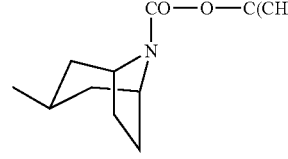 | 170.73, 170.55, 153.81, 13.00, 131.56, 108.75, 80.13, 44.04, 43.54, 28.97, 28.88, 28.26, 26.25, 25.40 |
| 271 | 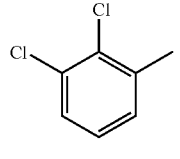 | 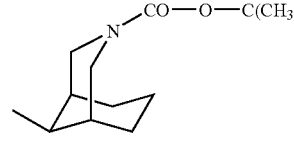 | 170.46, 155.24, 138.35, 136.06, 135.99, 131.84, 130.54, 128.07, 79.90, 40.33, 39.46, 35.56, 31.25, 28.92, 26.67 |
| 272 | 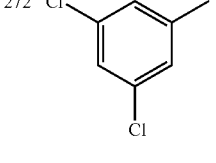 | 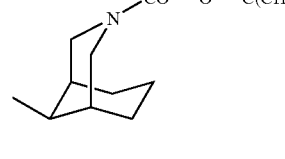 | 170.42, 155.35, 141.71, 136.36, 134.41, 127.09, 80.05, 40.34, 39.48, 35.60, 31.31, 28.92, 26.67 |

TABLE 4-continued
| EX | R₁ | R₁₆ + R₁₇/R₁₈ | m.p./¹H-NMR/¹³C-NMR |
|----|-----|----------------|----------------------|
| 273 | 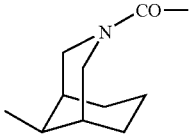 | 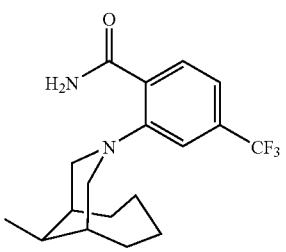 | 170.38, 155.51, 141.74, 133.47, 133.19, 129.28, 127.91, 123.81, 80.38, 46.00, 40.45, 39,53, 35.60, 31.36, 28.90, 26.60 |
| 274 | 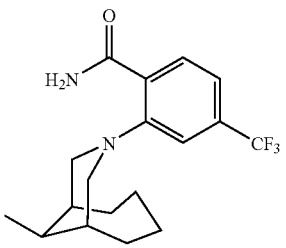 | 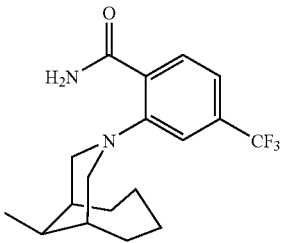 | (CDCl₃/DMSO-d₆): 171.89, 170.37, 129.15, 135.54, 135.42, 131.74, 130.82, 130.56, 127.80, 116.87, 61.83, 39.27, 38.78, 36.13, 31.29, 26.91 |
| 275 | 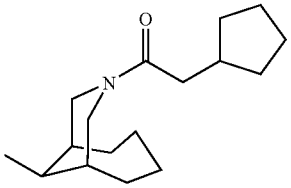 | 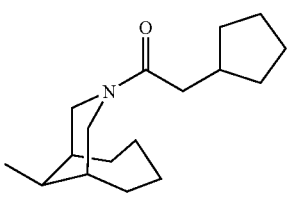 | 170.41, 141.73, 136.35, 134.40, 131.01, 127.11, 62.23, 38.98, 38.86, 35.89, 31.06, 26.83 |
| 276 | 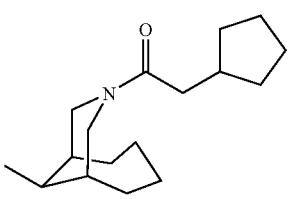 | | 170.81, 141.77, 133.41, 133.06, 130.83, 129.27, 127.88, 62.07, 39.04, 35.97, 31.11, 26.84 |
| 277 | | | 173.06, 170.82, 142.22, 136.26, 134.16, 127.05, 54.43, 49.85, 40.20, 39.81, 39.09, 37.17, 35.86, 35.64, 33.19, 31.58, 31.43, 26.97, 26.37, 25.37, 25.33 |
| 278 | | | 172.69, 170.42, 138.53, 135.97, 131.79, 130.56, 128.05, 54.27, 49.69, 40.18, 39.76, 39.14, 37.04, 35.66, 33.16, 31.44, 26.99, 26.36, 25.37, 25.33 |
| 279 | | | 173.27, 171.15, 142.24, 133.63, 133.28, 132.94, 132.59, 129.18, 127.60, 124.14, 121.42, 118.70, 54.45, 49.86, 40.19, 39.79, 39.02, 37.21, 35.89, 35.53, 33.13, 31.58, 31.33, 26.93, 26.33, 25.30, 25.25 |

TABLE 4-continued

| EX | R₁ | R₁₆ + R₁₇/R₁₈ | m.p./¹H-NMR/¹³C-NMR |
|---|---|---|---|
| 280 | 3,5-bis(CF₃)phenyl | N-CO-O-C(CH₃)₃ (benzomorphan-type bicyclic) | 171.84, 154.00, 142.66, 139.62, 139.35, 133.05, 132.71, 129.95, 129.40, 129.01, 127.27, 126.74, 126.46, 124.16, 79.03, 48.41, 7.62, 40.39, 38.63, 35.96, 33.16, 32.74, 30.00, 28.50 |
| 281 | 2,3-dichloro-6-methylphenyl | N-CO-O-C(CH₃)₃ (benzomorphan-type bicyclic) Pure isomer of unknown stereochemistry | 171.57, 154.08, 139.84, 139.53, 139.15, 135.59, 135.45, 131.75, 130.55, 129.98, 129.41, 127.84, 126.70, 126.45, 79.01, 48.47, 47.71, 40.18, 38.51, 36.04, 35.99, 33.13, 32.76, 30.04, 28.54 |
| 282 | 2,3-dichloro-6-methylphenyl | N-CO-O-C(CH₃)₃ (benzomorphan-type bicyclic) Pure isomer of unknown stereochemistry | 169.93, 155.06, 139.30, 139.00, 138.41, 136.03, 135.98, 131.83, 130.57, 129.80, 129.25, 128.09, 126.93, 79.70, 42.00, 41.11, 39.58, 32.81, 32.40, 28.64 |
| 283 | 2,5-dichloro-3-bromo-4-methylthiophene | N-CO-O-C(CH₃)₃ (benzomorphan-type bicyclic) | 171.17, 153.90, 139.116, 138.83, 136.06, 131.42, 129.54, 128.97, 126.33, 126.07, 125.43, 108.28, 79.03, 48.00, 47.22, 39.44, 38.08, 35.34, 35.32, 32.76, 32.19, 29.55, 27.99 |
| 284 | 2,5-dichloro-3-bromo-4-methylthiophene | N-CO-O-C(CH₃)₃ (benzomorphan-type bicyclic) | 170.09, 154.68, 138.96, 138.66, 136.71, 131.04, 129.42, 128.86, 126.58, 126.48, 125.87, 108.28, 79.38, 41.52, 41.09, 40.94, 40.71, 39.16, 32.38, 32.03, 28.24 |
| 285 | 3,5-bis(CF₃)phenyl | N-CO-O-CH₃ (bicyclic amine) | 170.76, 170.43, 155.94, 154.64, 142.05, 141.88, 132.96, 132.61, 129.27, 127.68, 126.83, 124.13, 121.39, 80.36, 80.29, 47.50, 46.12, 45.61, 44.94, 42.52, 36.93, 36.39, 32.14, 31.85, 31.13, 30.88, 30.08, 29.42, 29.29, 29.23, 27.81, 20.29, 13.87 mix |
| 286 | 2,3-dichloro-6-methylphenyl | tropane phenylacetate ester | 239-240° |

TABLE 4-continued

| EX | R₁ | R₁₆ + R₁₇/R₁₈ | m.p./¹H-NMR/¹³C-NMR |
|---|---|---|---|
| 287 | 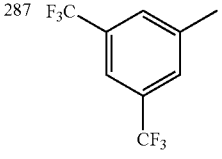 | 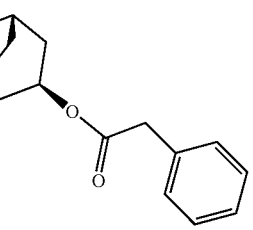 | 85-90° |

Analogously to methods as described in the PROCEDURES (Examples A to Q), but using appropriate starting materials, compounds of formula

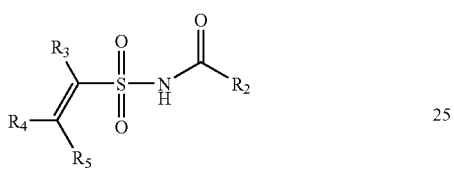

wherein $R_2$, $R_3$ and $R_4+R_5$ are as defined in TABLE 5 (compounds of formula I, wherein m is 0, n is 0, and $R_1$ is a group of formula II) are obtained.

If not otherwise indicated in TABLE 5 ¹C-NMR and ¹³C-NMR data are determined in CDCl₃.

TABLE 5

| EX | R₂ | R₄ + R₅/R₃ | m.p./¹H-NMR/¹³C-NMR |
|---|---|---|---|
| 288 | 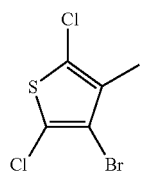 | 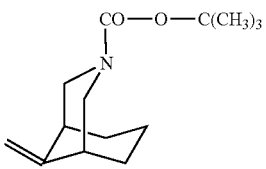<br>R₃ = F | 158.34, 157.96, 154.94, 144.81, 141.33, 137.70, 133.48, 133.13, 129.59, 128.15, 124.08, 121.36, 80.53, 50.60, 49.55, 49.33, 33.51, 32.01, 31.94, 31.39, 28.85 |
| 289 | 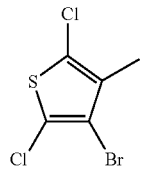 | 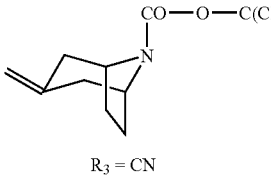<br>R₃ = CN | 153.65, 116.14, 109.03, 80.82, 28.77 |
| 290 | 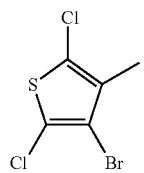 | 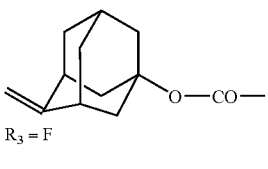<br>R₃ = F | 171.96, 158.46, 158.09, 145.82, 145.72, 139.92, 137.48, 131.21, 126.25, 108.85, 78.20, 49.55, 42.06, 41.65, 40.65, 38.38, 38.08, 33.12, 33.03, 32.36, 32.34, 31.13, 30.38, 30.02 |

TABLE 5-continued
| EX | R$_2$ | R$_4$ + R$_5$/R$_3$ | m.p./$^1$H-NMR/$^{13}$C-NMR |
|---|---|---|---|
| 291 | 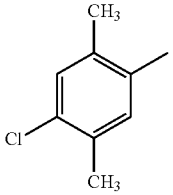 | 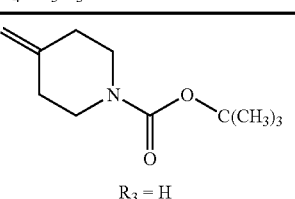<br>R$_3$ = H | 1.44(s, 9H); 2.25(t, 2H); 2.41(s, 3H); 2.58(s,3H); 2.85(t, 2H); 3.40(t, 2H); 3.48(t, 2H); 5.62(s, 1H); 7.30(s, 1H); 8.02(s, 1H); 8.06(broad, 1H) |
| 292 | 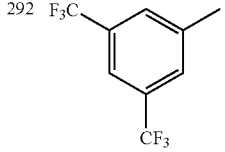 | 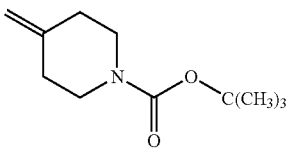<br>R$_3$ = H | (DMSO-d$_6$) 1.25(s, 9H); 2.02-2.08(m, 2H); 2.56-2.64(m, 2H); 3.38-3.20(m, 4H); 5.61(m, 1H); 8.30(s, 2H); 8.42(s, 1H) |
| 293 | 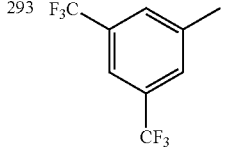 | 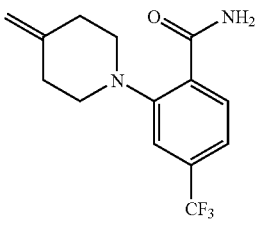<br>R$_3$ = H | (DMSO-d$_6$): 2.40(m, 2H), 2.91(m, 2H), 3.01(m, 2H), 3.08(m, 2H), 5.78(s, 1H), 7.26(s, 1H), 7.34(d, 1H), 7.62 and 8.07 (2s, 2H, NH), 7.66(d, 1H), 8.45(s, 2H), 8.58(s, 1H) |
| 294 | 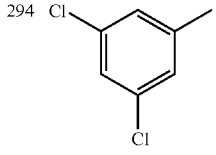 | 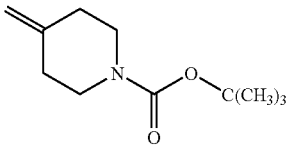<br>R$_3$ = H | 1.46(s, 9H); 2.26(t, 2H); 2.90(t, 2H); 3.41(t, 2H); 3.47(t, 2H); 5.76(s, 1H); 7.56(t, 1H); 7.90(d, 2H) |
| 295 | 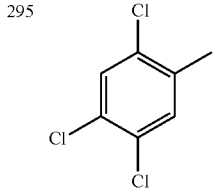 | 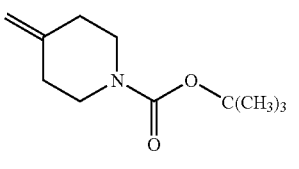<br>R$_3$ = H | 1.44(s, 9H); 2.28(m, 2H); 2.85(m, 2H); 3.42(m, 2H); 3.50(m, 2H); 5.62(s, 1H); 7.63(s, 1H); 8.18(broad, 1H); 8.35(s, 1H) |
| 296 | 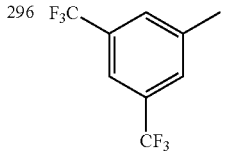 | 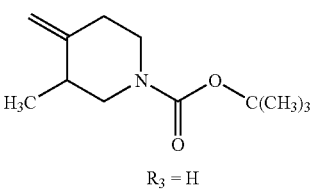<br>R$_3$ = H | 168.16, 163.00, 141.84, 133.36, 133.01, 129.40, 127.82, 121.40, 112.34, 80.55, 28.76 |
| 297 | 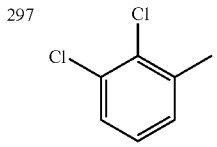 | 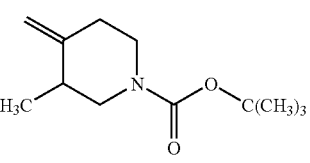<br>R$_3$ = H | 167.39, 163.23, 155.07, 138.64, 135.94, 135.88, 131.72, 130.71, 127.99, 112.60, 80.45, 28.77 |

TABLE 5-continued
| EX | R$_2$ | R$_4$ + R$_5$/R$_3$ | m.p./$^1$H-NMR/$^{13}$C-NMR |
|---|---|---|---|
| 298 | 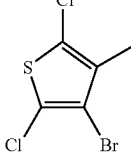 | 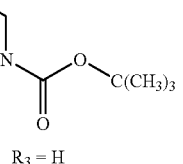<br>R$_3$ = H | 169.84, 168.85, 154.55, 154.50, 134.83, 122.96, 121.40, 79.32, 43.86, 42.49, 28.24, 28.09 |
| 299 | 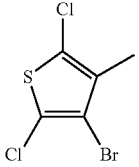 | 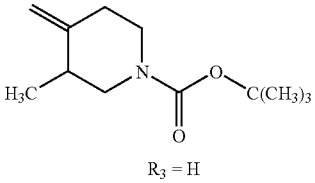<br>R$_3$ = H | 167.43, 155.08, 131.89, 126.13, 108.82, 80.45, 39.78, 28.78 |
| 300 | 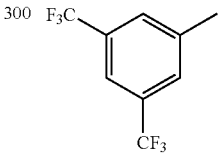 | 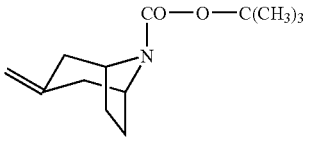<br>R$_3$ = H | 162.46, 141.87, 133.34, 133.00, 129.37, 127.83, 121.40, 118.03, 80.40, 54.13, 30.08, 28.82 |
| 301 | 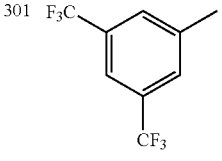 | 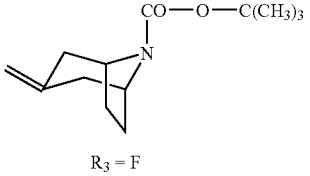<br>R$_3$ = F | 153.69, 145.66, 143.194, 141.23, 135.04, 134.92, 133.82, 133.47, 133.13, 132.78, 129.57, 128.16, 126.78, 124.06, 121.34, 80.38, 52.97, 28.80 |
| 302 | 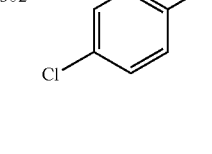 | 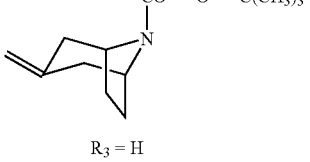<br>R$_3$ = H | 162.6, 161.2, 157.6, 141.04, 137.58, 130.31, 129.69, 118.37, 80.27, 33.4, 31.7, 29.8, 28.83 |
| 303 | 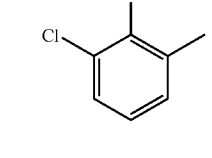 | 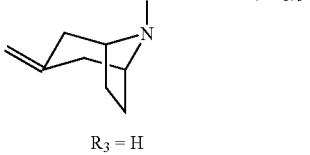<br>R$_3$ = H | 161.89, 138.63, 135.92, 131.71, 128.02, 118.17, 80.26, 30.08, 28.83 |
| 304 | 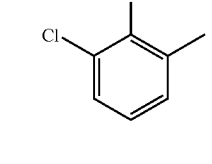 | 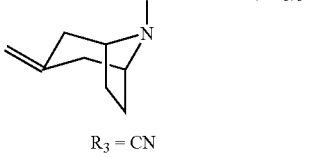<br>R$_3$ = CN | 127.89, 28.78 |
| 305 | 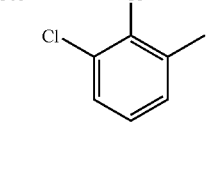 | 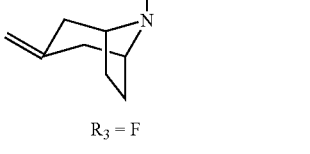<br>R$_3$ = F | 153.69, 145.69, 143.35, 138.13, 136.14, 136.01, 134.35, 134.22, 131.92, 130.82, 128.02, 80.30, 55.01, 28.81 |

TABLE 5-continued
| EX | R$_2$ | R$_4$ + R$_5$/R$_3$ | m.p./$^1$H-NMR/$^{13}$C-NMR |
|---|---|---|---|
| 306 | 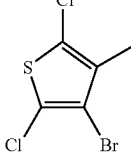 | 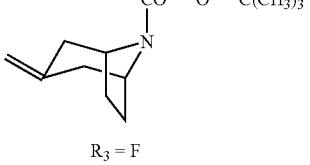<br>R$_3$ = F | 136.80, 117.99, 80.31, 54.15, 30.08, 28.85 |
| 307 | 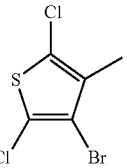 | 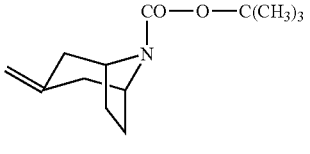<br>R$_3$ = F | 145.74, 143.27, 134.69, 126.27, 108.73, 80.33, 53.53, 53.13, 28.82 |
| 308 | 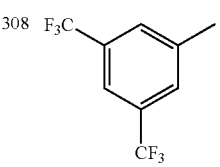 | 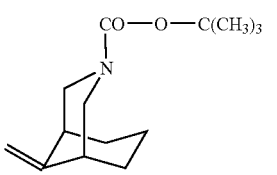<br>R$_3$ = H | 172.88, 163.03, 155.29, 141.98, 133.32, 132.98, 129.32, 127.75, 126.85, 124.14, 121.42, 118.71, 109.95, 80.75, 42.11, 28.88, 28.60 |
| 309 | 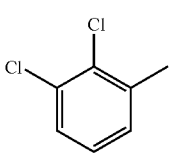 | 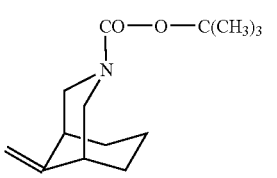<br>R$_3$ = H | 171.98, 162.62, 138.27, 135.52, 135.46, 131.28, 130.34, 127.63, 109.60, 80.19, 51.18, 50.59, 50.29, 49.56, 41.62, 34.52, 34.36, 33.65, 33.48, 33.31, 28.48, 19.76 |
| 310 | 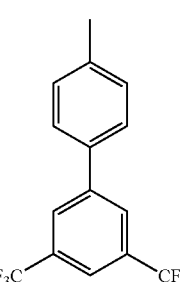 | 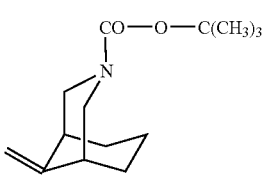<br>R$_3$ = H | (DMSO-d$_6$): 12.11(s, 1H), 8.35(s, 1H), 8.25(t, J=1.7Hz, 1H), 8.17-8.22(m, 2H), 8.02(dt, J=1.7 + 8Hz, 1H), 7.79(t, J= 8Hz, 1H), 5.77(s, 1H), 3.98-4.18(m, 2H), 3.78(br.s, 1H), 2.70-2.98(m, 2H), 2.24(br.s, 1H), 1.52-1.96(m, 6H), 1.37(s, 9H) |
| 311 | 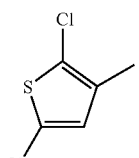 | 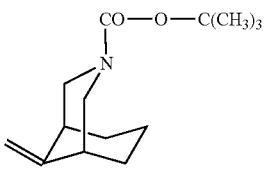<br>R$_3$ = H | 172.41, 163.25, 155.17, 134.96, 132.34, 127.84, 109.97, 80.50, 51.60, 51.08, 50.74, 50.03, 42.07, 34.80, 34.11, 33.91, 30.07, 28.89, 20.20 |
| 312 | 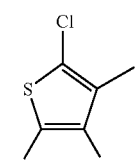 | 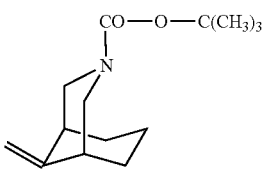<br>R$_3$ = H | 170.31, 164.59, 135.38, 132.50, 125.43, 110.85, 109.01, 80.05, 51.55, 51.00, 50.66, 49.95, 41.73, 34.64, 33.73, 33.56, 28.80, 20.16 |

TABLE 5-continued
| EX | R$_2$ | R$_4$ + R$_5$/R$_3$ | m.p./$^1$H-NMR/$^{13}$C-NMR |
|---|---|---|---|
| 313 | 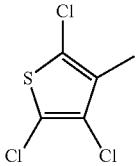 | 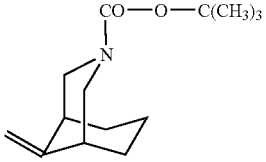<br>R$_3$ = H | 169.30, 163.66, 154.10, 133.70, 130.31, 122.51, 121.09, 109.85, 79.26, 50.61, 50.02, 49.68, 49.01, 40.74, 33.72, 32.70, 27.77, 19.17 |
| 314 | 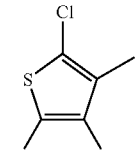 | 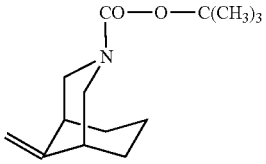<br>R$_3$ = F | αD$_{25}$ = −4.1° (optical rotation)<br>Pure(+) isomer of unknown stereochemestry |
| 315 | 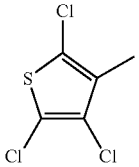 | 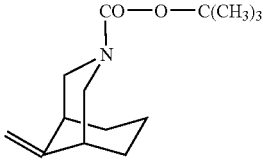<br>R$_3$ = F | αD$_{25}$ = +7.9° (optical rotation)<br>Pure(−) isomer of unknown sterochem. |
| 316 | 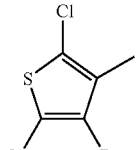 | 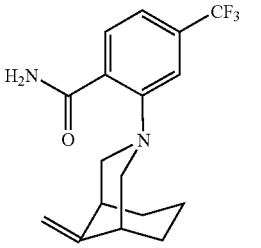<br>R$_3$ = H | 171.24, 170.90, 163.49, 150.58, 136.63, 134.44, 134.11, 131.78, 131.40, 130.94, 126.18, 125.23, 122.52, 119.73, 116.99, 111.22, 108.84, 59.63, 58.06, 42.49, 34.37, 34.28, 33.44, 19.45 |
| 317 | 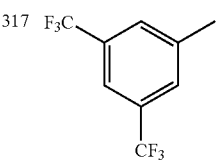 | 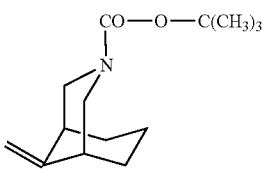<br>R$_3$ = F | 144.81, 141.33, 137.70, 133.48, 133.13, 129.59, 128.15, 124.08, 121.36, 80.53, 50.60, 49.55, 49.33, 33.51, 32.01, 31.94, 31.39, 28.85, 19.85 |
| 318 | 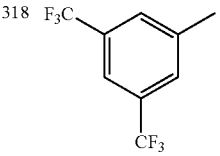 | 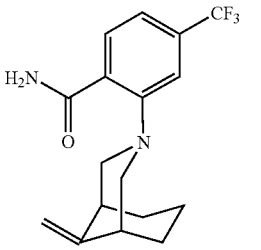<br>R$_3$ = H | 171.43, 163.10, 150.47, 142.01, 134.47, 133.36, 133.09, 131.31, 130.53, 129.32, 127.82, 123.88, 121.70, 117.16, 111.31, 59.57, 58.16, 42.39, 34.33, 34.26, 33.32, 19.39 |

TABLE 5-continued
| EX | R₂ | R₄ + R₅/R₃ | m.p./¹H-NMR/¹³C-NMR |
|---|---|---|---|
| 319 | 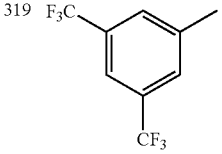 3,5-bis(CF₃)phenyl | 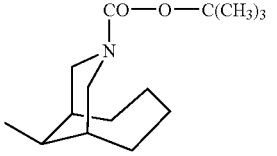 CO—O—C(CH₃)₃, R₃ = H | 169.02, 141.94, 133.36, 133.02, 130.01, 128.69, 80.42, 44.05, 36.25, 29.37, 29.37, 28.86, 28.32 |
| 320 | 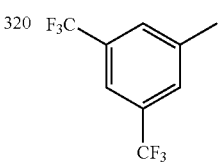 3,5-bis(CF₃)phenyl | 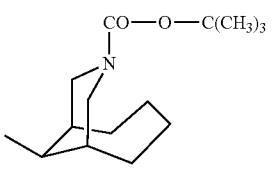 CO—O—C(CH₃)₃, R₃ = F | 157.93, 157.56, 155.27, 144.25, 141.33, 140.98, 140.88, 133.81, 133.47, 133.12, 132.78, 130.25, 130.04, 129.63, 129.51, 129.05, 128.87, 128.60, 128.30, 127.99, 126.79, 124.07, 121.36, 118.64, 80.65, 49.87, 33.80, 33.72, 33.63, 33.54, 33.20, 33.05, 29.54, 29.33, 28.83, 28.30, 28.10 |
| 321 | 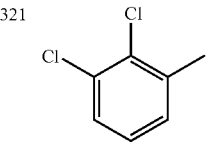 2,3-dichlorophenyl | 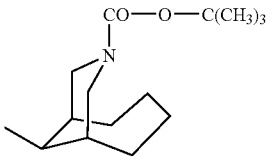 CO—O—C(CH₃)₃, R₃ = H | 167.91, 162.70, 155.31, 138.69, 135.94, 135.90, 135.77, 130.72, 128.77, 127.34, 80.39, 43.88, 36.17, 36.02, 29.57, 29.37, 28.89, 28.38, 28.16 |
| 322 | 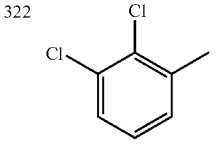 2,3-dichlorophenyl | 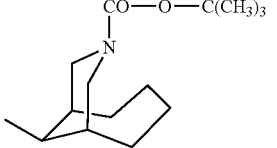 CO—O—C(CH₃)₃, R₃ = F | 155.15, 141.89, 140.47, 140.38, 138.21, 136.13, 136.02, 131.87, 130.84, 128.06, 80.40, 33.69, 33.61, 33.06, 28.84, 26.64 |
| 323 | 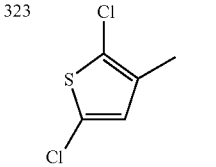 2,5-dichlorothienyl | 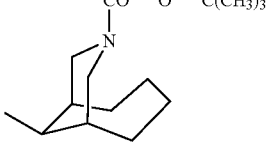 CO—O—C(CH₃)₃, R₃ = H | 168.05, 162.89, 155.36, 134.99, 132.24, 127.87, 127.83, 116.30, 80.41, 53.80, 49.57, 43.96, 36.17, 30.07, 28.87, 26.73, 26.54 |
| 324 | 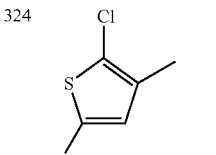 2,5-dichlorothienyl | 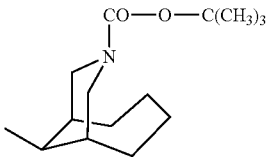 CO—O—C(CH₃)₃, R₃ = F | 155.15, 144.33, 141.86, 140.61, 140.51, 134.31, 133.1, 127.96, 127.85, 80.38, 33.71, 33.63, 33.11, 32.96, 28.86, 26.68 |

TABLE 5-continued
| EX | R₂ | R₄ + R₅/R₃ | m.p./¹H-NMR/¹³C-NMR |
|---|---|---|---|
| 325 | 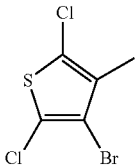 | 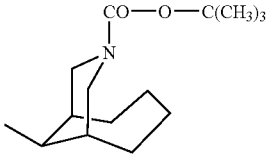<br>R₃ = H | 168.30, 162.87, 155.31, 136.66, 131.80, 126.17, 108.77, 80.40, 43.97, 36.23, 36.11, 29.60, 29.38, 28.88, 28.36, 28.14 |
| 326 | 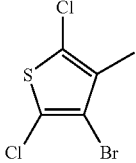 | 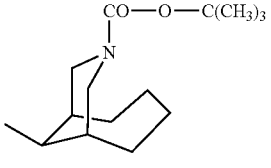<br>R₃ = F | 157.93, 157.57, 155.18, 144.29, 141.82, 140.73, 140.64, 131.16, 126.25, 108.73, 80.43, 33.82, 33.73, 33.57, 33.09, 32 |
| 327 | 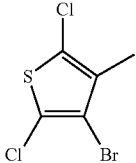 | 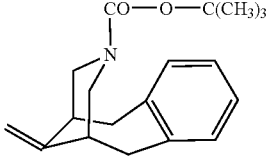<br>R₃ = H | 163.98, 129.19, 128.90, 126.74, 126.40, 114.47, 79.43, 42.71, 42.50, 38.31, 33.72, 33.50, 29.53, 28.17, 22.54 |
| 328 | 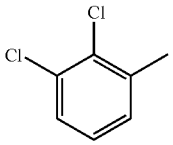 | 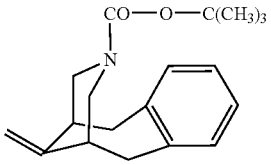<br>R₃ = H | 162.79, 138.58, 135.83, 131.66, 129.12, 127.98, 127.68, 127.37, 115.07, 80.37, 43.22, 37.65, 36.81, 28.71 |
| 329 | 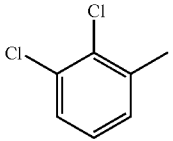 | 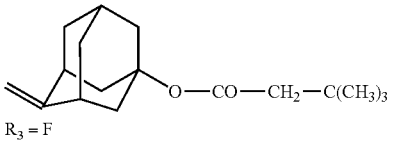<br>R₃ = F | 172.04, 158.62, 158.25, 145.09, 145.00, 140.10, 138.36, 137.65, 135.96, 135.90, 130.79, 127.27, 78.30, 49.56, 42.02, 40.52, 38.18, 37.10, 33.08, 33.02, 32.33, 32.26, 31.11, 30.66, 30.37, 29.93, 29.71 |
| 330 | 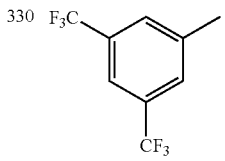 | 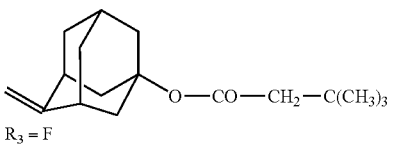<br>R₃ = F | 172.02, 158.27, 157.91, 141.29, 139.85, 137.41, 133.48, 133.14, 132.79, 130.34, 49.54, 32.25, 31.13, 30.33, 29.93 |

Analogously to methods as described in the PROCEDURES (Examples A to Q), but using appropriate starting materials, compounds of formula

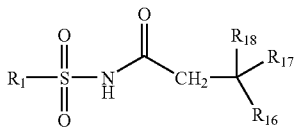

wherein $R_{18}$ is hydrogen and $R_1$ and $R_{16}+R_{17}$ are as defined in TABLE 6 (compounds of formula I, wherein m is 0, n is 1, and $R_2$ is a group of formula VII) are obtained. If not otherwise indicated $^{13}$C-NMR and $^1$HNMR data in TABLE 6 are determined in DMSO-$d_6$.

TABLE 6

| EX | $R_1$ | $R_{16}+R_{17}$ | m.p./$^1$H-NMR/$^{13}$C-NMR |
|---|---|---|---|
| 331 | 3,5-bis(CF₃)-phenyl | cyclohexyl-NH-C(O)-O-C(CH₃)₃ (Diastereoisomeric mixture) | 93-96° |
| 332 | 3,5-bis(CF₃)-phenyl | cyclohexyl-NH-C(O)-O-C(CH₃)₃ | 0.93(q, 2H); 1.03(q, 2H); 1.34 (s, 9H); 1.40-1.50(m, 3H); 1.65 (d, 2H); 2.07(d, 2H); 3.07(m, 1H); 4.50(broad, 1H); 8.12(s, 1H); 8.52(s, 2H) |
| 333 | 3,5-bis(CF₃)-phenyl | cyclohexyl-NH-C(O)-O-C(CH₃)₃ | 1.12-1.28(m, 2H); 1.45(s, 9H); 1.40-1.70(m, 6H); 1.83-1.94(m 1H); 2.21(d, 2H); 3.62-3.76(m, 1H); 4.60(broad, 1H); 5.33 (broad, 1H); 8.12(s, 1H); 8.50 (s, 2H) |
| 334 | 4-chloro-2,5-dimethylphenyl | cyclohexyl-NH-C(O)-O-C(CH₃)₃ | 0.90(q, 1H); 1.07(q, 1H); 1.20-1.52(m, 6H); 1.37/1.39(s, 9H); 1.63-1.78(m, 1H); 2.10/2.17(d, 2H); 2.38(s, 3H); 2.52(s, 3H); 3.10/3.40(m, 1H); 7.15/7.21(d, 1H); 7.52(s, 1H); 7.80(s, 1H); 12.18/12, 22(s, 1H) |
| 335 | 2-CF₃-phenyl | cyclohexyl-NH-C(O)-O-C(CH₃)₃ | 0.88(q, 2H); 1.05(q, 2H); 1.18-1.54(m, 6H); 1.36/1.37(s, 9H); 1.63-1.78(m, 1H); 2.12/2.18(d, 2H); 3.10/3.40(m, 1H); 6.63/ 6.70(d, 1H); 7.88-8.04(m, 3H); 8.30(m, 1H); 12.36(s, 1H) |
| 336 | 2,3-dichlorophenyl | cyclohexyl-NH-C(O)-O-C(CH₃)₃ | 0.88(d, 1H); 1.07(d, 1H); 1.18-1.53(m, 6H); 1.36/1.38(s, 9H); 1.64-1.79(m, 1H); 2.10/2.17(d, 2H); 3.33-3.41(m, 1H); 6.30 (broad, 1H); 7.56(dt, 1H); 7.91 (dd, 1H); 8.04(dd, 1H); 12.3 (broad, 1H) |

TABLE 6-continued

| EX | $R_1$ | $R_{16} + R_{17}$ | m.p./$^1$H-NMR/$^{13}$C-NMR |
|---|---|---|---|
| 337 | 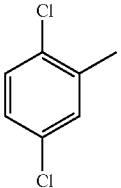 | 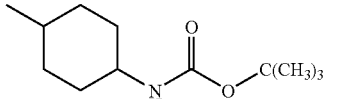 | 0.90(q, 1H); 1.08(q, 1H); 1.20-1.30(m, 2H); 1.30-1.54(m, 4H); 1.37/1.38(s, 9H); 1.65-1.81(m, 1H); 2.13/2.20(d, 2H); 3.10/3.40 (m, 1H); 6.63/6.70(d, 1H); 7.73 (d, 1H); 7.81(d, 1H); 8.03(s, 1H) |
| 338 | 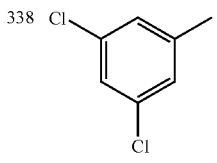 | 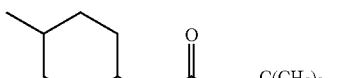 | 0.91(q, 1H); 1.08(q, 1H); 1.18-1.32(m, 2H); 1.36(s, 9H); 1.35-1.56(m, 3H); 1.65-1.80(m, 2H); 2.13/2.17(d, 2H); 3.10/3.41(m, 1H); 6.62-6.73(m, 1H); 7.85(s, 2H); 8.06(s, 1H); 12.0(broad, 1H) |
| 339 | 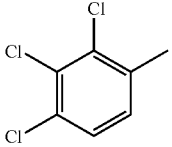 | 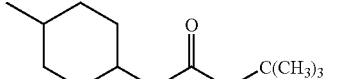 | 1.12(q, 1H); 1.27(q, 1H); 1.30-1.50(m, 2H); 1.56/1.57(s, 9H); 1.60-1.75(m, 3H); 1.84-2.02(m, 2H); 2.34/2.40(d, 2H); 3.31/3.61 (m, 1H); 6.85/6.91(d, 1H); 8.13 (d, 1H); 8.29(d, 1H); 12.4(broad, 1H) |
| 340 | 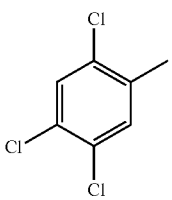 | 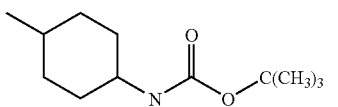 | 0.90(q, 1H); 1.08(q, 1H); 1.20-1.32(m, 2H); 1.37/1.38(s, 9H); 1.35-1.55(m, 3H); 1.66-1.80(m, 2H); 2.12/2.18(d, 2H); 3.10/3.40 (m, 1H); 6.64/6.70(d, 1H); 8.15(s, 1H); 8.16(s, 1H); 12.7(broad, 1H) |
| 341 | 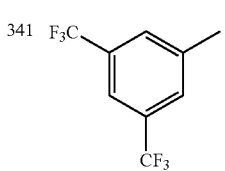 | 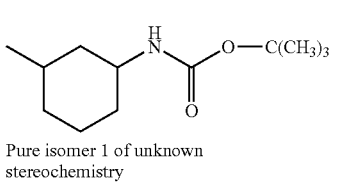<br>Pure isomer 1 of unknown stereochemistry | (CDCl$_3$): 170.84, 141.87, 133.31, 132.97, 132.62, 129.30, 127.73, 124.11, 121.39, 47.03, 44.35, 38.28, 35.32, 32.48, 30.38, 28.80 |
| 342 | 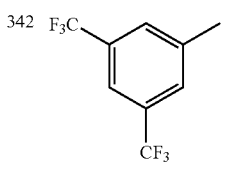 | 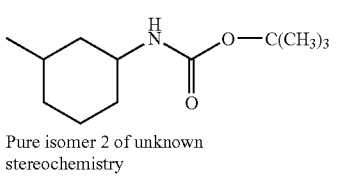<br>Pure isomer 2 of unknown stereochemistry | (CDCl$_3$): 170.90, 141.79, 133.32, 132.97, 129.31, 127.73, 124.10, 44.28, 35.90, 32.74, 28.78, 28.43, 26.43 |
| 343 | 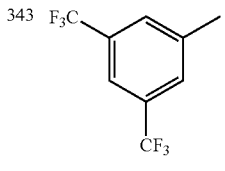 | 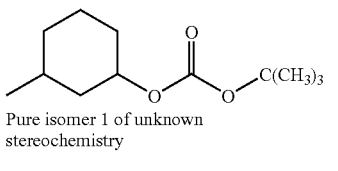<br>Pure isomer 1 of unknown stereochemistry | (CDCl$_3$): 153.06, 132.95, 132.67, 128.63, 127.31, 123.40, 121.23, 82.06, 75.40, 43.47, 33.48, 31.03, 30.50, 27.78 |
| 344 | 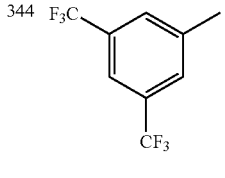 | 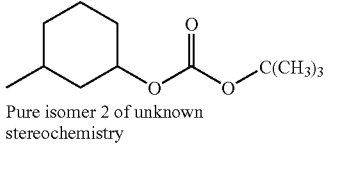<br>Pure isomer 2 of unknown stereochemistry | (CDCl$_3$): 169.97, 153.49, 141.64, 133.73, 133.45, 133.18, 132.90, 129.37, 127.94, 123.81, 121.64, 82.27, 72.32, 43.62, 33.61, 29.49, 28.24, 27.24 |

TABLE 6-continued

| EX | R₁ | R₁₆ + R₁₇ | m.p./¹H-NMR/¹³C-NMR |
|---|---|---|---|
| 345 | 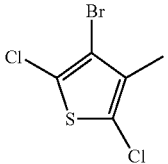 | 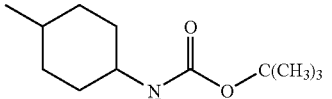<br>Diasteroisometric mixture | 0.95(q, 1H); 1.11(q, 1H); 1.22-1.36(m, 2H); 1.38(s, 9H); 1.40-1.60(m, 3H); 1.68-1.87(m, 2H); 2.15/2.21 (d, 2H); 3.13/3.44(m, 1H); 6.73/6.68(d, 1H); 12.8(broad, 1H) |
| 346 | 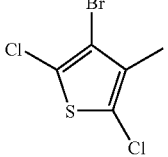 | 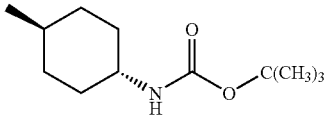<br>Pure isomer(trans) | 0.97(q, 2H), 1.15(q, 2H), 1.55-1.68(m, 3H), 1.77(d, 2H), 2.18 (d, 2H), 3.12-3.22(m, 1H), 6.71 (d, 1H, NH) |
| 347 | 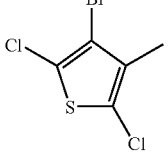 | 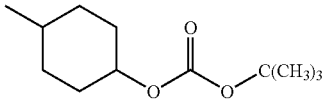<br>Pure isomer 1 of unknown stereochemistry | (CDCl₃): 170.55, 153.54, 137.42, 131.23, 126.33, 108.60, 82.22, 72.46, 72.40, 43.40, 33.39, 29.53, 28.31, 28.24, 27.28 |
| 348 | 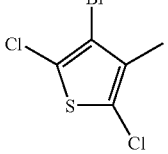 | 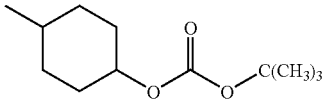<br>Pure isomer 2 of unknown stereochemistry | (CDCl₃): 169.93, 153.01, 137.07, 130.76, 129.02, 128.22, 126.01, 125.29, 108.13, 81.96, 75.37, 42.90, 33.25, 31.09, 30.53, 27.80, 21.44 |

Analogously to methods as described in the PROCEDURES (Examples A to Q), but using appropriate starting materials, compounds of formula

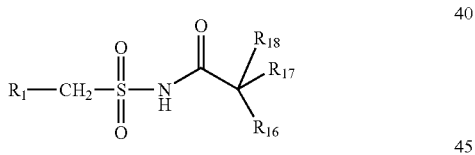

wherein $R_{18}$ is hydrogen and $R_1$ and $R_{16}+R_{17}$ are as defined in TABLE 7 (compounds of formula I, wherein m is 1, n is 0, and $R_1$ is a group of formula VII) are obtained. If not otherwise indicated in TABLE 7 ¹³C-NMR and ¹HNMR data in TABLE 7 are determined in CDCl₃.

TABLE 7

| EX | R₁ | R₁₆ + R₁₇ | m.p./¹H-NMR |
|---|---|---|---|
| 349 | 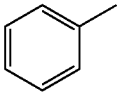 | 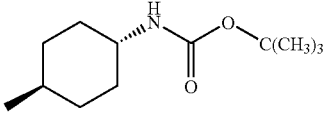 | m.p. = 212-215° |

TABLE 7-continued

| EX | R₁ | R₁₆ + R₁₇ | m.p./¹H-NMR |
|---|---|---|---|
| 350 | 3,4-diCl-phenyl | cyclohexyl-N(CH₃)-C(O)-O-C(CH₃)₃ | (DMSO-d₆): 11.52(s, 1H), 7.70 (d, J=8.4Hz, 1H), 7.50(d, J=2Hz, 1H), 7.26(dd, J=8.4 + 2Hz, 1H), 4.73(s, 2H), 3.72(br.s, 1H), 2.62(s, 3H), 2.06-2.14(m, 1H), 1.36-1.80(m, 8H), 1.37 (s, 9H) |
| 351 | 3,4-diCl-phenyl | cyclohexyl-NH-C(O)-O-C(CH₃)₃ | (DMSO-d₆): 11.33(s, 1H), 7.68 (d, J=8.3Hz, 1H); 7.51(d, J= 2Hz, 1H), 7.26(dd, J=2 + 8.3 Hz, 1H), 6.74(br.d, J=6.6Hz, 1H), 4.73(s, 2H), 3.43(br.s, 1H), 2.19-2.28(m, 1H), 1.40-1.77(m, 8H), 1.37(s, 9H) |
| 352 | 3,4-diCl-phenyl | cyclohexyl-NH-C(O)-O-C(CH₃)₃ | m.p.: 211-215° |
| 353 | 3,5-diCl-phenyl | cyclohexyl-NH-C(O)-O-C(CH₃)₃ | 8.40(s, 1H), 7.39(s, 1H), 7.24(s, 2H), 4.63(s, 2H), 3.69 (br.s, 1H), 2.30(br.s, 1H), 1.55-1.78(br.m, 8H), 1.44(s, 9H) |
| 354 | 3,5-diCl-phenyl | cyclohexyl-NH-C(O)-O-C(CH₃)₃ | (DMSO-d₆): 11.50(s, 1H), 7.66 (t, J=1.9Hz, 1H), 7.29(d, J= 1.9Hz, 2H), 6.68(d, J=7.8Hz, 1H), 4.73(s, 2H), 3.10-3.20 (br.s, 1H), 2.05(tt, J=3.3 + 11.9Hz, 1H), 1.63-1.82(m, 4H), 1.28-1.42(m, 2H), 1.35 (s, 9H), 1.00-1.14(m, 2H) |
| 355 | 3,5-diCl-phenyl | cyclohexyl-CH₂-NH-C(O)-O-C(CH₃)₃ | (DMSO-d₆): 11.49(s, 1H), 7.66 (s, 1H), 7.29(s, 2H), 6.78(t, J= 5.6Hz, 1H), 4.72(s, 2H), 2.73 (t, J=6.3Hz, 2H), 2.08(t, J= 11.8Hz, 1H), 1.63-1.73(m, 4H), 1.35(s, 9H), 1.22-1.35 (m, 2H), 0.73-0.86(m, 2H) |
| 356 | 3,5-di(CF₃)-phenyl | cyclohexyl-NH-C(O)-O-C(CH₃)₃ | (DMSO-d₆) 11.52(s, 1H), 8.18 (s, 1H), 7.95(s, 2H), 6.66(d, J= 7.3Hz, 1H), 4.97(s, 2H), 3.07-3.18(m, 1H), 2.04(tt, J= 3.2 + 8.6Hz), 1.62-1.80(m, 4H), 1.35(s, 9H), 1.26-1.35 (m, 2H), 0.98-1.11(m, 2H) |
| 357 | 3,5-di(CF₃)-phenyl | cyclohexyl-CH₂-NH-C(O)-O-C(CH₃)₃ | 204-207 |
| 358 | phenyl | cyclohexyl-CH₂-NH-C(O)-O-C(CH₃)₃ | 0.93(s, 9H); 1.42(s, 9H); 1.23-1.62(m, 3H); 1.78-2.14(m, 5H); 2.98(t, 2H); 4.58(broad, 1H); 4.64(s, 2H); 7.26-7.40(m, 5H); 7.58(s, 1H) |

TABLE 7-continued

| EX | R₁ | R₁₆ + R₁₇ | m.p./¹H-NMR |
|---|---|---|---|
| 359 | 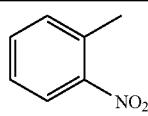 | 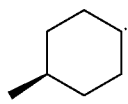 | 0.98(q, 2H); 1.42(s, 9H); 1.52-2.20(m, 8H); 2.99(t, 2H); 4.59 (broad, 1H); 5.24(s, 2H); 7.40-7.65(m, 3H); 8.01(d, 1H); 8.14 (s, 1H) |
| 360 | 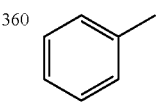 | 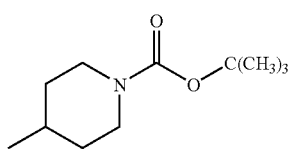 | 1.42(s, 9H); 1.40-1.78(m, 4H); 2.21(m, 1H); 2.92(t, 2H); 4.06 (d, 2H); 4.68(s, 2H); 7.30-7.40 (m, 5H); 7.75(s, 1H) |
| 361 | 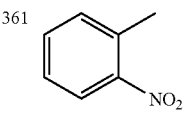 | 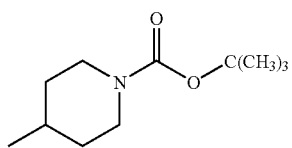 | 1.44(s, 9H); 1.45-1.90(m, 4H); 2.33(m, 1H); 2.78(t, 2H); 4.10 (d, 2H); 5.22(s, 2H); 7.42-7.70 (m, 3H); 7.92(broad, 1H); 8.03 (d, 1H) |

Analogously to methods as described in the PROCEDURES (Examples A to Q), but using appropriate starting materials, compounds of formula

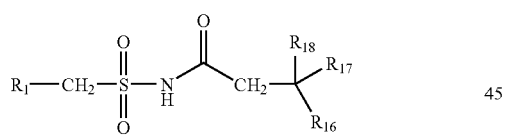

wherein $R_{18}$ is hydrogen and $R_1$ and $R_{16}+R_{17}$ are as defined In TABLE 8 (compound of formula I, wherein m is 1, n is 1, and $R_2$ is a group of formula VII) are obtained.

TABLE 8

| EX | R₁ | R₁₆ + R₁₇ | ¹HNMR |
|---|---|---|---|
| 362 | 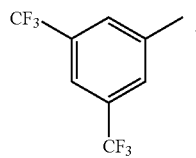 | 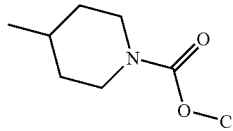 | (DMSO-d₆): 11.63(s, 1H), 8.18(s, 1H), 7.99(s, 2H), 5.00(s, 2H), 3.86 (d, J=12.7Hz, 2H), 2.67(br.s, 1H), 2.13(d, J=7Hz, 2H), 1.76-1.89 (m, 1H), 1.50-1.60(m, 2H), 1.37 (s, 9H), 0.88-1.03(m, 2H) |

Analogously to methods as described in the PROCEDURES (Examples A to Q), but using appropriate starting materials, compounds of formula

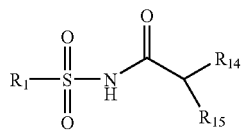

(5)

wherein $R_1$, $R_{14}$ and $R_{15}$ are as defined in TABLE 9 (compounds of formula I, wherein m is 0, n is 0, and $R_1$ is a group of formula VI) are obtained. If not otherwise indicated $^{13}$C-NMR and $^1$HNMR data in TABLE 9 are determined in DMSO-$d_6$.

TABLE 9

| EX | $R_{14}$ | $R_{15}$ | $R_1$ | mp./$^1$HNMR |
|---|---|---|---|---|
| 363 | 3,5-(CF$_3$)$_2$-C$_6$H$_3$- | -NH-(1-Boc-piperidin-4-yl) | 4-CF$_3$-C$_6$H$_4$- | 150-154° |
| 364 | 3,5-(CF$_3$)$_2$-C$_6$H$_3$- | 1-methylpiperidine-4-carboxamide-N-cyclohexyl | 4-CF$_3$-C$_6$H$_4$- | 171-175° |
| 365 | 3,5-(CF$_3$)$_2$-C$_6$H$_3$- | 1-methylpiperidine-4-carboxamide-N-cyclohexyl | 3-CH$_3$-C$_6$H$_4$- | 169-171° |
| 366 | 3,5-(CF$_3$)$_2$-C$_6$H$_3$- | 1-methylpiperidine-4-carboxamide-N-cyclohexyl | 4-F-C$_6$H$_4$- | 140-145° |
| 367 | 3,5-(CF$_3$)$_2$-C$_6$H$_3$- | 1-methylpiperidine-4-carboxamide-N-cyclohexyl | 4-Cl-C$_6$H$_4$- | 229-231° Racemate |

TABLE 9-continued

| EX | R₁₄ | R₁₅ | R₁ | mp./¹HNMR |
|---|---|---|---|---|
| 368 | 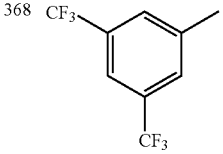 | 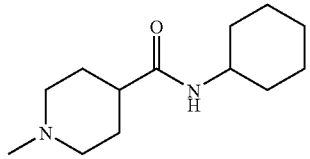<br>1-[(S)-1-(3,5-Bis-trifluoro-methylphenyl)-(4-chloro-benzenesulfonylamino)-2-oxo-ethyl]-piperidine-4-carboxylic acid cyclohexylamide | 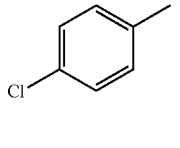 | 9.7(s br NH), 8.19(s, 1H), 8.0(s, 2H), 7.73(d, J=8Hz, NH), 7.5(d, J=8.5Hz, 2H), 7.37(d, J=8.5Hz, 2H), 4.95(s, 1H), 3.46(m, 2H), 2.85(m, 2H), 2.71(m, 1H), 2.27(m, 1H), 1.85(m, 3H), 1.67(m, 4H), 1.53(m, 1H), 1.16(m, 6H) |
| 369 | 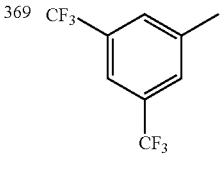 | 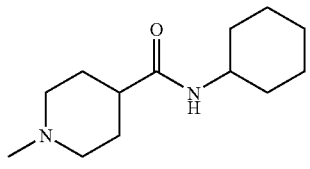<br>1-[(R)-1-(3,5-Bis-trifluoro-methylphenyl)-(4-chloro-benzenesulfonylamino)-2-oxo-ethyl]-piperidine-4-carboxylic acid cyclohexylamide | 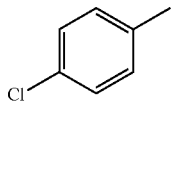 | 9.76(s, br, NH), 8.19(s, 1H), 8.08(s, 2H), 7.73(d, J=8Hz, NH), 7.54(d, J=8.5Hz, 2H), 7.37(d, J=8.5Hz, 2H), 4.95 (s, 1H), 3.46(m, 2H), 2.85 (m, 2H), 2.71(m, 1H), 2.27 (m, 1H), 1.85(m, 3H), 1.67 (m, 4H), 1.53(m, 1H), 1.16 (m, 6H) |
| 370 | 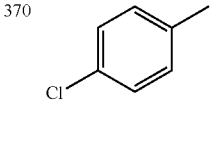 | 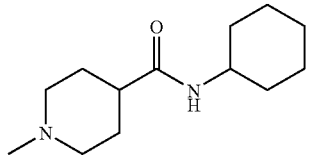 | 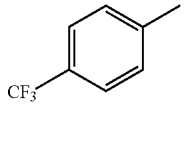 | 250-254° |
| 371 | 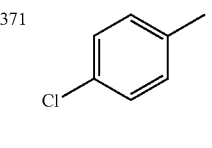 | 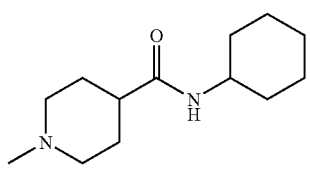 | 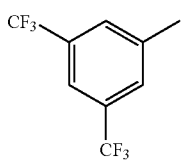 | 254-257° |
| 372 |  | 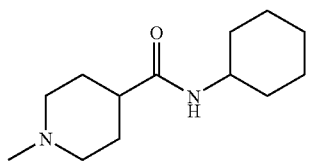 | 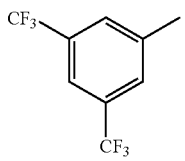 | 249-251° |

TABLE 9-continued

| EX | R14 | R15 | R1 | mp./¹HNMR |
|---|---|---|---|---|
| 373 | 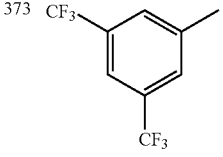 | 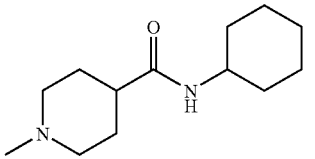 | 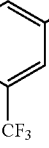 | 7.89(s, br, 3H), 7.72(d, J=8.1Hz, 2H), 7.63(d, J=8.2Hz, 2H), 7.53(s, br, 1H), 3.85(s, br, 1H), 3.47(m, 1H), 2.77(s, 1H), 2.50(s, br, 1H), 1.99(s, br, 2H), 1.88(s, br, 1H), 1.65(m, 4H), 1.52(m, 4H), 1.21(m, 3H), 1.16 (m, 3H) |

Analogously to methods as described in the PROCEDURES (Examples A to Q), but using appropriate starting materials, compounds of formula

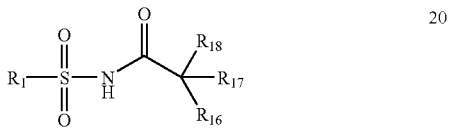

wherein $R_1$, $R_{16}+R_{17}$ and $R_{18}$ are as defined in TABLE 10 (compounds of formula I, wherein m is 0, n is 0, and $R_2$ is a group of formula VII) are obtained.

TABLE 10

| EX | R16 + R17 | R18 | R1 | ¹HNMR/¹³C-NMR |
|---|---|---|---|---|
| 374 | 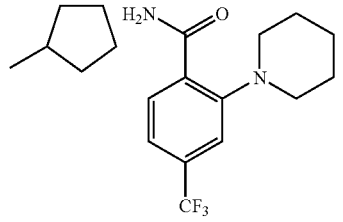 | 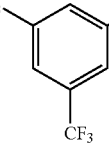 | 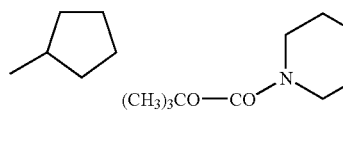 | 175.20, 168.92, 152.57, 135.26, 134.93, 133.67, 133.33, 132.98, 132.83, 132.63, 129.88, 129.27, 127.71, 126.82, 125.06, 124.10, 122.35, 121.99, 121.38, 117.92, 59.79, 54.81, 43.10, 32.94, 28.94, 25.10 |
| 375 | 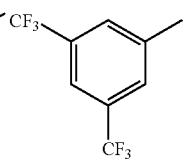 | (CH₃)₃CO—CO | 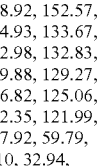 | 174.98, 155.00, 141.65, 133.42, 133.07, 129.25, 127.83, 121.33, 80.13, 59.57, 44.31, 44.10, 32.40, 28.77, 28.11, 25.45 |

Analogously to methods as described in the PROCEDURES (Examples A to Q), but using appropriate starting materials, compounds of formula

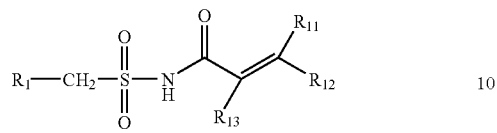

wherein $R_{13}$ is hydrogen and $R_1$ and $R_{11}+R_{12}$ are as defined in TABLE 11 (compounds of formula I, wherein m is 1, n is 0, and $R_2$ is a group of formula V) are obtained.

TABLE 11

| EX | $R_{11} + R_{12}$ | $R_1$ | $^1$HNMR |
|---|---|---|---|
| 376 | (structure with N-C(=O)-O-C(CH$_3$)$_3$ and vinyl substituent) | 3,5-bis(CF$_3$)-phenyl | (CDCl$_3$): 7.92(s, 1H), 7.83(s, 2H), 7.50 (br.s, 1H), 5.46(s, 1H), 4.81(s, 2H), 4.04-4.42(m, 2H), 2.92-3.13(m, 2H), 1.40-1.30(m 8H) 1.46(s, 9) |

Analogously to methods as described in the PROCEDURES (Examples A to Q), but using appropriate starting materials, compounds of formula

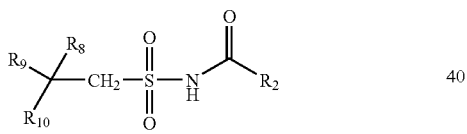

wherein $R_8$ is hydrogen or is as defined in TABLE 12 and $R_2$ and $R_9+R_{10}$ are as defined in TABLE 12 (compounds of formula I, wherein m is 0, n is 1, $R_1$ is a group of formula VII) are obtained.

TABLE 12

| EX | $R_9 + R_{10}$ | $R_2$ | m.p./$^1$HNMR |
|---|---|---|---|
| 377 | (CH$_3$)$_3$C-O-C(=O)-N-(4-methylpiperidine) | 2,3-dichlorophenyl | (DMSO-d$_6$): 1.12(dq, 2H), 1.40(s, 9H), 1.85(dd, 2H), 2.03(m, 1H), 2.65-2.71 (m, 2H), 3.07(d, 2H), 3.87(broad d, 2H), 7.29(dd, 1H), 7.32(dd, 1H), 7.51 (dd, 1H) |

TABLE 12-continued

| EX | $R_9 + R_{10}$ | $R_2$ | m.p./$^1$HNMR |
|---|---|---|---|
| 378 | (CH$_3$)$_3$C-O-C(O)-N-piperidine-4-methyl | 3,5-bis(CF$_3$)phenyl | (DMSO-d$_6$): 8.45(s, 2 H), 8.12(s, 1H), 3.80(br.d, J=12.5Hz, 2H), 2.46(d, J=6.3Hz, 2 H), 2.70(br. s, 2H), 1.90-1.98(m, 1H), 1.80(br.d, J=13.3Hz, 2H), 1.00-1.12(m, 2H) |
| 379 | 2-(4-methylpiperidin-1-yl)-4-CF$_3$-benzamide | 3,5-bis(CF$_3$)phenyl | 268-273° |
| 380 | 2-(4-methylpiperidin-1-yl)-4-CF$_3$-benzamide | 2,3-dichlorophenyl | m.p.: 173-176° |
| 381 | (CH$_3$)$_3$C-O-C(O)-N-piperidine (4-methyl, $R_8$) wherein $R_8$ is OH | 3,5-bis(CF$_3$)phenyl | m.p.: 154-159° |
| 382 | 2-(4-methyl-4-OH-piperidin-1-yl)-4-CF$_3$-benzamide ($R_8$) wherein $R_8$ is OH | 3,5-bis(CF$_3$)phenyl | (DMSO-d$_6$): 1.38(s, 9H), 1.59(d, 2H), 1.70(m, 2H), 3.05(broad, 2H), 3.35(s, 2H), 3.60(broad d, 2H), 4.91(s, 1H, OH), 8.18(s, 1H), 8.46(s, 2H) |
| 383 | 1-(4-methylpiperidin-1-yl)-2-cyclopentyl-ethanone | 3,5-bis(CF$_3$)phenyl | (CDCl$_3$): 2 rotamers, selected signals: 11.30(br.s, 1H), 8.62(s, 2H), 8.08(s, 1H), 4.60 + 3.95(2 x br.d, J=13Hz, 2 x 1H), 3.16 + 3.13(2 x d, J=12Hz, 2H), 2.63(t, J=12Hz, 1H) |
| 384 | camphor-type bicyclic ketone (H$_3$C, CH$_3$) | 3,5-bis(CF$_3$)phenyl | (DMSO-d$_6$): 0.78(s, 3H), 1.04(s, 3H), 1.32(m, 1H), 1.40(m, 1H), 1.84-1.92 (m, 2H), 1.97 m, 1H), 2.29(m, 1H), 2.62 (m, 1H), 3.26 and 3.47(AB, 2H), 8.15 (broad, 1H), 8.48(broad, 2H) |

Analogously to methods as described in the PROCEDURES (Examples A to Q), but using appropriate starting materials, compounds of formula

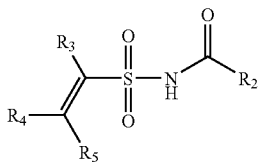

wherein $R_3$ is hydrogen, and $R_2$ and $R_4+R_5$ are as defined in TABLE 13 (compounds of formula I, wherein m is 0, n is 0, $R_1$ is a group of formula II, and $R_2$ is $(C_{6-18})$aryl), are obtained.

halogen, nitro, di$(C_{1-4})$alkylamino, cyano, $(C_{1-6})$alkyl, $(C_{1-4})$haloalkyl, $(C_{1-4})$alkoxy, $(C_{1-4})$haloalkoxy, aminocarbonyl, di$(C_{1-4})$alkylaminocarbonyl, $(C_{1-4})$alkylcarbonyl, $(C_{1-4})$alkoxycarbonyl and carboxyl;

$R_2$ is a group of formula

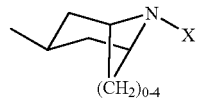

X is selected from $(C_{1-8})$alkoxycarbonyl and phenyl, which phenyl group is substituted with 0 to 5 substitu-

TABLE 13

| EX | $R_4 + R_5$ | $R_2$ | $^1$H-NMR |
|---|---|---|---|
| 385 | | 3,5-bis(CF$_3$)phenyl | (DMSO-d$_6$): 1.42(s, 9H), 2.33(t, 2H), 2.82(t, 2H), 3.44(broad, 4H), 6.61(s, 1H), 8.41(s, 1H), 8.57(s, 2H) |
| 386 | 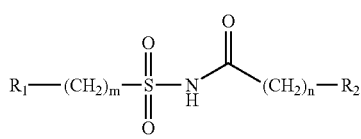 | CF$_3$-phenyl-CF$_3$ | (DMSO-d$_6$): 2.40(m, 2H), 2.93-3.10(m, 6H), 6.44(s, 1H), 7.27(s, 1H), 7.36(d, 1H), 7.66(s, 1H), 7.70(s, 1H), 8.15(d, 2H, NH), 8.48(s, 2H) |

The invention claimed is:

1. A compound of formula $$R_1-(CH_2)_m-\underset{\underset{O}{\overset{O}{\|}}}{\overset{O}{\|}}{S}-\underset{H}{N}-\overset{O}{\overset{\|}{C}}-(CH_2)_n-R_2 \qquad I$$

wherein
$R_1$ is phenyl or naphthyl, which is unsubstituted or substituted with 1 to 5 substituents selected from the group consisting of
halogen, nitro, di$(C_{1-4})$alkylamino, cyano, $(C_{1-6})$alkyl, $(C_{1-4})$haloalkyl, unsubstituted phenylcarbonylamino $(C_{1-4})$alkyl, $(C_{1-4})$alkoxy, $(C_{1-4})$haloalkoxy, aminocarbonyl, di$(C_{1-4})$alkylaminocarbonyl, $(C_{1-4})$alkylcarbonyl, $(C_{1-4})$alkoxycarbonyl, unsubstituted phenyl, carboxyl, and phenyl-substituted phenylcarbonylamino$(C_{1-4})$alkyl or substituted phenyl, wherein the phenyl-substituents are selected from the group consisting of
halogen, nitro, di$(C_{1-4})$alkylamino, cyano, $(C_{1-6})$alkyl, $(C_{1-4})$haloalkyl, $(C_{1-4})$alkoxy, $(C_{1-4})$haloalkoxy, aminocarbonyl, di$(C_{1-4})$alkylaminocarbonyl, $(C_{1-4})$alkylcarbonyl, $(C_{1-4})$alkoxycarbonyl and carboxyl; and
m and n are 0.

2. A compound of claim 1 which is a compound of formula

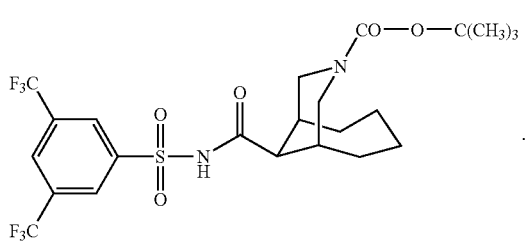

3. A compound of claim 1 in the form of a salt.

4. A pharmaceutical composition comprising at least one compound of claim 1 in association with at least one pharmaceutically acceptable excipient.

* * * * *